United States Patent
Ruediger et al.

(10) Patent No.: US 10,238,638 B2
(45) Date of Patent: Mar. 26, 2019

(54) BENZOTHIAZOLE AND BENZOTHIOPHENE COMPOUNDS

(71) Applicants: Bristol-Myers Squibb Company, Princeton, NJ (US); Universite de Montreal, Montreal (CA)

(72) Inventors: Edward H. Ruediger, Montreal (CA); Daniel H. Deon, Denver, CO (US); Marc Gagnon, Montreal (CA); Shoshana L. Posy, Princeton, NJ (US)

(73) Assignees: Universite De Montreal, Montreal, QC (CA); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/549,307

(22) PCT Filed: Feb. 25, 2016

(86) PCT No.: PCT/US2016/019453
§ 371 (c)(1),
(2) Date: Aug. 7, 2017

(87) PCT Pub. No.: WO2016/138199
PCT Pub. Date: Sep. 1, 2016

(65) Prior Publication Data
US 2018/0036287 A1 Feb. 8, 2018

Related U.S. Application Data

(60) Provisional application No. 62/120,988, filed on Feb. 26, 2015.

(51) Int. Cl.
C07D 513/04 (2006.01)
A61K 31/426 (2006.01)
A61K 31/495 (2006.01)

(52) U.S. Cl.
CPC .......... A61K 31/426 (2013.01); A61K 31/495 (2013.01); C07D 513/04 (2013.01)

(58) Field of Classification Search
CPC .................................................... A61K 31/426
See application file for complete search history.

(56) References Cited

U.S. PATENT DOCUMENTS

| 2015/0094297 A1 | 4/2015 | Banville et al. |
| 2015/0119390 A1 | 4/2015 | Martel et al. |
| 2015/0133446 A1 | 5/2015 | Lawrence et al. |

FOREIGN PATENT DOCUMENTS

| WO | 2013163241 A1 | 10/2013 |
| WO | 2013163244 A1 | 10/2013 |
| WO | 2013163279 A1 | 10/2013 |

OTHER PUBLICATIONS

Vippagunta et al. (2001).*
Wolff et al. (1997).*
Banker et al. (1997).*
International Search Report issued in PCT/US2016/019453 dated May 31, 2016 (3 pages).
International Written Opinion issued in PCT/US2016/019453 dated May 31, 2016 (5 pages).

* cited by examiner

Primary Examiner — Paul V Ward
(74) Attorney, Agent, or Firm — Hoffmann & Baron, LLP

(57) ABSTRACT

The present invention provides benzothiazole compounds or benzothiophene compounds of Formula I having the structure: wherein $X^1$, $X^2$, $X^3$, $X^4$, $X^5$, Y, $WR^2$, $R^3$, $R^4$, $R^5$, $R^6$, $R^7$ and AA and other moieties are as defined herein, or a stereoisomer, tautomer, pharmaceutically acceptable salt, prodrug ester or solvate form thereof. These compounds are inhibitors of platelet aggregation and thus can be used as medicaments for treating or preventing thromboembolic disorders.

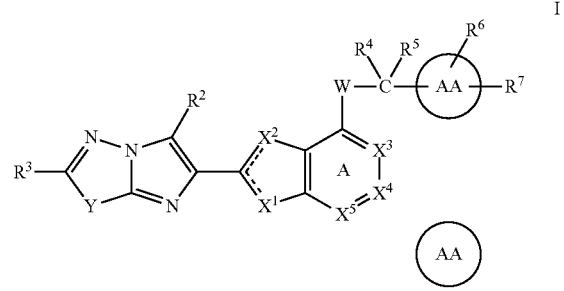

21 Claims, No Drawings

BENZOTHIAZOLE AND BENZOTHIOPHENE COMPOUNDS

CROSS-REFERENCE TO RELATED APPLICATIONS

This application is the National Stage of International Application No. PCT/US2016/019453, filed on Feb. 25, 2016, which claims the benefit of priority from U.S. Provisional Patent Application No. 62/120,988, filed on Feb. 26, 2015, the contents of which are incorporated by reference herein in their entirety.

FIELD OF THE INVENTION

The present invention provides novel benzothiazole and benzothiophene inhibitors of platelet aggregation which are useful in preventing or treating thromboembolic disorders. This invention also relates to pharmaceutical compositions containing these compounds and methods of using the same.

BACKGROUND OF THE INVENTION

Thromboembolic diseases remain the leading cause of death in developed countries despite the availability of anticoagulants such as warfarin (COUMADIN®), heparin, low molecular weight heparins (LMWH), synthetic pentasaccharides, and antiplatelet agents such as aspirin and clopidogrel (PLAVIX®).

Current anti-platelet therapies have limitations including increased risk of bleeding as well as partial efficacy (relative cardiovascular risk reduction in the 20 to 30% range). Thus, discovering and developing safe and efficacious oral or parenteral antithrombotics for the prevention and treatment of a wide range of thromboembolic disorders remains an important goal.

Alpha-thrombin is the most potent known activator of platelet aggregation and degranulation. Activation of platelets is causally involved in atherothrombotic vascular occlusions. Thrombin activates platelets by cleaving G-protein coupled receptors termed protease activated receptors (PARs). PARs provide their own cryptic ligand present in the N-terminal extracellular domain that is unmasked by proteolytic cleavage, with subsequent intramolecular binding to the receptor to induce signaling (tethered ligand mechanism; Coughlin, S. R., *Nature*, 407:258-264 (2000)). Synthetic peptides that mimic the sequence of the newly formed N-terminus upon proteolytic activation can induce signaling independent of receptor cleavage. Platelets are a key player in atherothrombotic events. Human platelets express at least two thrombin receptors, commonly referred to as PAR1 and PAR4. Inhibitors of PAR1 have been investigated extensively, and several compounds, including vorapaxar and atopaxar have advanced into late stage clinical trials. Recently, in the TRACER phase III trial in ACS patients, vorapaxar did not significantly reduce cardiovascular events, but significantly increased the risk of major bleeding (Tricoci, P. et al., *N. Eng. J. Med.*, 366(1):20-33 (2012). Vorapaxar is currently being marketed as Zontivity® by Merck. Thus, there remains a need to discover new antiplatelet agents with increased efficacy and reduced bleeding side effects.

There are several early reports of preclinical studies of PAR4 inhibitors. Lee, F-Y. et al., "Synthesis of 1-Benzyl-3-(5'-hydroxymethyl-2'-furyl)indazole Analogues as Novel Antiplatelet Agents", *J. Med. Chem.*, 44(22):3746-3749 (2001) discloses in the abstract that the compound

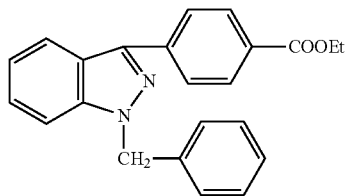

58

"was found to be a selective and potent inhibitor of protease-activated receptor type 4 (PAR4)-dependent platelet activation."

Compound 58 is also referred to as YD-3 in Wu, C-C. et al., "Selective Inhibition of Protease-activated Receptor 4-Dependent Platelet Activation by YD-3", *Thromb. Haemost.*, 87:1026-1033 (2002). Also, see Chen, H. S. et al., "Synthesis and antiplatelet activity of ethyl 4-(1-benzyl-1H-indazol-3-yl)benzoate (YD-3) derivatives"", *Bioorg. Med. Chem.*, 16:1262-1278 (2008).

EP1166785 A1 and EP0667345 disclose various pyrazole derivatives which are useful as inhibitors of platelet aggregation.

The PCT publications WO2013/163279, WO2013/163244 and WO2013/163241 disclose various PAR4 antagonists which are useful as inhibitors of platelet aggregation.

SUMMARY OF THE INVENTION

It has been found that compounds of Formula (I) in accordance with the present invention are PAR4 antagonists which inhibit platelet aggregation in gamma-thrombin induced platelet aggregation assays.

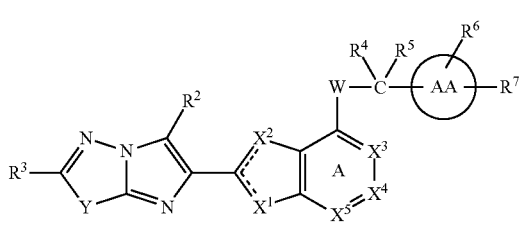

I wherein the various moieties are as defined herein.

Accordingly, the present invention provides novel benzothiazole and benzothiophene analogues which are PAR4 antagonists and are useful as selective inhibitors of platelet aggregation, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of thromboembolic disorders comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a thromboembolic disorder.

Other features and advantages of the invention will be apparent from the following detailed description and claims.

DETAILED DESCRIPTION

In one embodiment, the present invention provides benzothiazole or benzothiophene compounds, stereoisomers, tautomers, salts, solvates or prodrugs thereof, of Formula I having the structure:

I or a stereoisomer, tautomer, pharmaceutically acceptable salt, solvate or prodrug thereof, wherein:
the dashed lines represent double-bonds with the proviso that only one of the two dashed line double bonds exists at the same time;
$X^2$ is S and $X^1$ is N or $CR^{1a}$; or $X^2$ is O and $X^1$ is N; or $X^2$ is $NR^{1b}$ and $X^1$ is N or $CR^{1a}$; or $X^2$ is N and $X^1$ is $NR^{1b}$; or $X^2$ is $CR^{1a}$ and $X^1$ is $NR^{1b}$;
$X^3$, $X^4$, and $X^5$ are independently selected from $CR^{1d}$ and N;
$R^{1a}$ is selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;
$R^{1b}$ is selected from the group consisting of H, $C_1$-$C_3$ alkyl, and halo-$C_1$-$C_2$alkyl;
$R^{1d}$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo $C_1$-$C_3$ alkyl, halo-$C_{1-2}$-alkoxy, halo-$C_{1-2}$-alkylthio, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;
Y is S or $CR^{1e}$=$CR^{1f}$—;
$R^{1e}$ is independently at each occurrence selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;
$R^{1f}$ is independently at each occurrence selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;
$R^2$ is H, halo, $C_1$-$C_4$ alkyl, halo-$C_1$-$C_2$alkyl, $C_1$-$C_4$ alkoxy, CN or $C_3$-$C_5$ cycloalkyl;
$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl, $C_{1-4}$ alkylamino, alkylamino—($C_{1-2}$ alkoxy) $C_{1-2}$ alkyl, $C_{2-3}$ alkenyl, $C_{2-3}$ alkynyl, tetrahydrofuran-2-yl, and halo;
W is O or S;
$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

AA is selected from the group consisting of a phenyl ring, a 5-membered heteroaryl ring containing at least one O, N or S atom, or a 6-membered heteroaryl ring containing at least one nitrogen atom; wherein
(i) when ring

AA is a 5-membered heteroaryl ring, then either (a) $R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or (b) $R^6$ is B—D—, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a linker selected from a single bond, —O—, —S—, $C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-

$C_4$-alkylene, —NHC(=O), —C(=O)NH—, —SO$_2$—NH—, —NH—SO$_2$—, and $C_2$-$C_6$ alkenylene; and
(ii) when ring (AA)

is phenyl or 6-membered heteroaryl, then $R^6$ is B—D, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a single bond;
each of $R^b$, $R^c$, $R^d$ and $R^e$, at each occurrence, is independently selected from the group consisting of halo, halo-$C_1$-$C_4$ alkoxy, OH, CN, NO$_2$, =O, NR$^{11}$R$^{12}$, COOH, $C_1$-$C_4$ alkoxy, $C_1$-$C_4$ alkylthio, $C_1$-$C_4$ alkoxycarbonyl, (C=O)NR$^{11}$R$^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2$NR$^{11}$R$^{12}$, N(R$^{13}$)(C=O)NR$^{11}$R$^{12}$, N(R$^{13}$)(C=O)OR$^{14}$, SO$_2$R$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, $C_3$-$C_6$ cycloalkyl, a 4- to 10-membered heterocyclyloxy; a $C_1$-$C_5$ alkyl substituted by 0 to 7 groups independently selected from halo, CF$_3$, OCF$_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; hydroxy-$C_1$-$C_4$-alkyl, halo-$C_1$-$C_4$ alkoxy, di-$C_1$-$C_4$-alkylamino-$C_1$-$C_4$-alkyl, halo-$C_4$-$C_4$ alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)NR$^{11}$R$^{12}$, CF$_3$, OCF$_3$, and CF$_2$CH$_3$;
$R^{11}$ and $R^{12}$ are independently, at each occurrence, selected from the group consisting of H; $C_1$-$C_4$ alkyl; halo-$C_1$-$C_4$-alkyl; hydroxy-$C_1$-$C_4$-haloalkyl; $C_1$-$C_4$ alkyleneoxy-$C_1$-$C_4$-alkylene; $C_2$-$C_4$ alkenyl; $C_2$-$C_4$ alkynyl; di-$C_1$-$C_4$-alkylamino-$C_1$-$C_4$-alkyl; $C_1$-$C_4$-alkylcarbonylamino-$C_1$-$C_4$-alkyl; di-$C_1$-$C_4$-alkoxy-$C_1$-$C_4$-alkyl; di-$C_1$-$C_4$-alkylaminophenyl; hydroxy-$C_1$-$C_4$-alkyl; cyano-$C_1$-$C_4$-alkyl; $C_1$-$C_4$-alkoxy-$C_1$-$C_4$-alkyl; $C_1$-$C_4$-alkoxycarbonyl-$C_1$-$C_4$-alkyl; $C_1$-$C_4$-alkoxycarbonyl; $C_1$-$C_4$-alkylcarbonyl; phenylcarbonyl; $C_1$-$C_4$-alkoxycarbonylamino-$C_1$-$C_4$-alkylcarbonyl; di-$C_1$-$C_4$-alkylamino-$C_1$-$C_4$-alkylcarbonyl; amino-$C_1$-$C_4$-alkylcarbonyl; 4- to 10-membered-heterocyclylcarbonyl; —(CR$^{14}$R$^{14}$)$_n$-phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-$C_1$-$C_4$-alkylamino, and cyano; —(CHR$^{13}$)$_n$—$C_3$-$C_6$-cycloalkyl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl; —(CHR$^{13}$)$_n$-4- to 10-membered-heterocyclyl substituted by 0 to 3 groups independently selected from the group consisting of halo, CF$_3$, OCF$_3$, 5- or 6-membered heteroaryl, OH, oxo, hydroxy-$C_1$-$C_4$-alkyl, and $C_1$-$C_4$ alkyl; and —(CHR$^{13}$)$_n$-5- to 10-membered-heteroaryl substituted by 0 to 3 groups independently selected from the group consisting of halo, CF$_3$, OCF$_3$, 5- or 6-membered heteroaryl, OH, hydroxy-$C_1$-$C_4$-alkyl, and $C_1$-$C_4$ alkyl; or
alternatively, $R^{11}$ and $R^{12}$, when attached to the same nitrogen, can be combined to form a 4- to 10-membered mono- or bicyclic heterocyclic ring containing carbon atoms substituted by 0 to 3 groups independently selected from the group consisting of halo, cyano, CF$_3$, CHF$_2$, OCF$_3$, OCHF$_2$, OCH$_2$F, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, NR$^{13}$, O and S(O)$_p$;
$R^{13}$ is independently, at each occurrence, selected from the group consisting of H, $C_1$-$C_6$ alkyl and —(CH$_2$) phenyl;
$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —(CH$_2$)$_n$phenyl substituted by 0 to 3 groups independently selected from the group consisting of halo, $C_1$-$C_4$ alkoxy, $C_1$-$C_4$ alkyl, cyclopropyl, CF$_3$, OCF$_3$, 5- or 6-membered heteroaryl, OH, OCHF$_2$, di-$C_1$-$C_4$-alkylamino, and cyano;
$R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_3$-$C_6$-cycloalkyl, halo-$C_3$-$C_6$-cycloalkyl, $C_1$-$C_4$-alkoxy, and halo-$C_1$-$C_4$-alkoxy;
or $R^6$ and $R^7$ can be taken together with the carbons to which they attach to form a 5-7 membered heterocyclyl, heteroaryl, or aryl ring;
n, at each occurrence, is independently selected from 0, 1, 2, 3, 4 or 5; and p, at each occurrence, is selected from 0, 1 and 2.

In an embodiment, $X^2$ is S and $X^1$ is N or CR$^{1a}$.
In an embodiment, $X^2$ is O and $X^1$ is N
In an embodiment $R^{1a}$ is H.
In an embodiment $R^{1b}$ is H.
In an embodiment, $X^2$ is S and $X^1$ is N.
In an embodiment, $X^3$, $X^4$, and $X^5$ are all CR$^{1d}$.
In an embodiment, $X^3$ and $X^5$ are CH, $X^4$ is CR$^{1d}$.
In an embodiment, $X^3$ and $X^5$ are CH and $X^4$ is alkoxy.
In an embodiment, $X^3$ and $X^5$ are CH and $X^4$ is C(OMe).
In an embodiment, Y is S.
In an embodiment, Y is —(CH=CH)—.
In an embodiment, W is O.
In an embodiment, $R^2$ is H.
In an embodiment, $R^3$ is alkyl, alkoxy or haloalkyl.
In an embodiment, $R^3$ is methyl, ethyl, methoxy, 1-fluoroethyl or 1,1-difluoroethyl.

In an embodiment, $R^4$ is H or methyl.
In an embodiment, $R^5$ is H or methyl.
In an embodiment, both $R^4$ and $R^5$ are H.
In an embodiment, ring

is phenyl or a 6-membered heteroaryl ring, wherein

is further substituted with $R^6$ and $R^7$.
In an embodiment, ring

is a 5-membered heteroaryl ring, wherein

is further substituted with $R^6$ and $R^7$.
In an embodiment, Y is S, W is O, $R^2$ is H, $R^3$ is methyl, ethyl, methoxy, 1-fluoroethyl or 1,1-difluoroethyl, $R^4$ and $R^5$ are both H, and ring

is phenyl, a 5-membered heteroaryl ring or a 6-membered heteroaryl ring, wherein

is further substituted with $R^6$ and $R^7$.
In an embodiment, Y is —(CH=CH)—, W is O, $R^2$ is H, $R^3$ is methyl, ethyl, methoxy, 1-fluoroethyl or 1,1-difluoroethyl, $R^4$ and $R^5$ are both H, and ring

is phenyl, a 5-membered heteroaryl ring or a 6-membered heteroaryl ring, wherein

is further substituted with $R^6$ and $R^7$.

In an embodiment,

is a thiazole, wherein

is further substituted with $R^6$ and $R^7$.
In an embodiment,

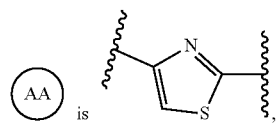 [SMILES: "AA" ; *c1csc(*)n1]

wherein

is further substituted with $R^6$ and $R^7$.
In an embodiment,

is a phenyl substituted thiazole, wherein

is further substituted with $R^7$, and wherein the phenyl is substituted with one or more of $R^b$, $R^c$, $R^d$, and $R^e$.
In an embodiment,

is a morpholino substituted thiazole, wherein

is further substituted with $R^7$, and wherein the morpholino group is substituted with one or more of $R^b$, $R^c$, $R^d$, and $R^e$.

In an embodiment,

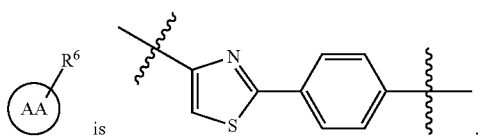 is

In an embodiment,

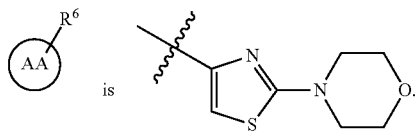 is

In an embodiment,

is a phenyl substituted thiazole, Y is S, $R^2$ is H, $R^3$ is methyl, ethyl, methoxy, 1-fluoroethyl or 1,1-difluoroethyl, W is O, $X^2$ is S, $X^1$ is N, and $X^3$, $X^4$ and $X^5$ are carbon.

In an embodiment,

is a morpholino substituted thiazole, Y is S, $R^2$ is H, $R^3$ is methyl, ethyl, methoxy, 1-fluoroethyl or 1,1-difluoroethyl, W is O, $X^2$ is S, $X^1$ is N, and $X^3$, $X^4$ and $X^5$ are carbon.

In an embodiment,

is a phenyl substituted thiazole, wherein

is further substituted with $R^7$, and wherein the phenyl is substituted with one or more of $R^b$, $R^c$, $R^d$, and $R^e$, Y is —(CH=CH)—, $R^2$ is H, $R^3$ is methyl, ethyl, methoxy, 1-fluoroethyl or 1,1-difluoroethyl, W is O, $X^2$ is S, $X^1$ is N, and $X^3$, $X^4$ and $X^5$ are carbon.

In an embodiment, $R^7$ is H and $R^b$, $R^c$, $R^d$, and $R^e$ are selected from the group consisting of H, COOH, $C_1$-$C_4$ alkoxycarbonyl, (C=O)$NR^{11}R^{12}$, $C_1$-$C_4$ alkylsulfonyl and $S(=O)_2NR^{11}R^{12}$, where $R^{11}$ and $R^{12}$ are as defined under Formula I.

In an embodiment, $R^7$ is H and $R^b$, $R^c$, $R^d$, and $R^e$ are (C=O)$NR^{11}R^{12}$, where $R^{11}$ and $R^{12}$ are as defined under Formula I.

In an embodiment, the compound of Formula I is the compound of Formula IA:

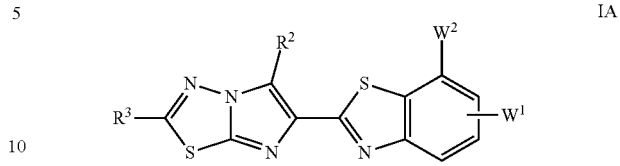

wherein $R^3$ is alkyl, fluoroalkyl, or alkoxy, $R^2$ is H, $W^1$ is methoxy and $W^2$ is the moiety:

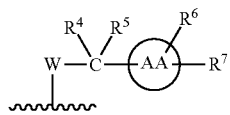

where W is O, $R^4=R^5=H$,

is thiazole, $R^6$ is phenyl or morpholino, $R^7$ is H or methyl, and $R^b$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, $S(=O)_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio.

In an embodiment, the compound of Formula I is the compound of Formula IB:

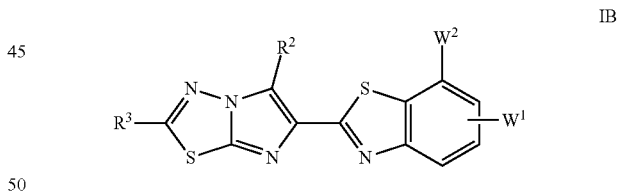

wherein $R^3$ is alkyl, $R^2$ is H, $W^1$ is methoxy and $W^2$ is the moiety:

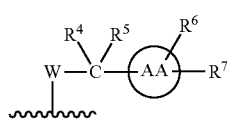

where W is O, $R^4=R^5=H$,

is thiazole, $R^7$ is H or methyl, $R^6$ is B—D—, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_5$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a linker selected from a single

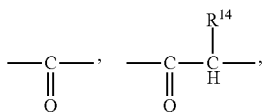

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O), —C(=O)NH—, —SO$_2$—NH—, —NH—SO$_2$—, and $C_2$-$C_6$ alkenylene.

In an embodiment, the compound of Formula I is the compound of Formula IC:

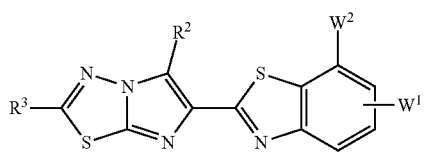

wherein $R^3$ is alkyl, $R^2$ is H, $W^1$ is methoxy and $W^2$ is the moiety:

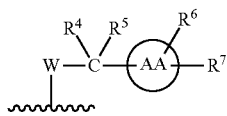

where W is O, $R^4$=$R^5$=H,

is thiazole, $R^7$ is H or methyl, and $R^6$ is a phenyl which may be optionally substituted with one or more $R^b$, $R^c$, $R^d$ and $R^e$, wherein each of $R^b$, $R^c$, $R^d$ and $R^e$ is independently selected from the group consisting of halo, halo-$C_1$-$C_4$ alkoxy, OH, CN, NO$_2$, =O, NR$^{11}$R$^{12}$, COOH, $C_1$-$C_4$ alkoxy, $C_1$-$C_4$ alkylthio, $C_1$-$C_4$ alkoxycarbonyl, (C=O)NR$^{11}$R$^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2$NR$^{11}$R$^{12}$, N(R$^{13}$)(C=O)NR$^{11}$R$^{12}$, N(R$^{13}$)(C=O)OR$^{14}$, SO$_2$R$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, $C_3$-$C_6$ cycloalkyl, a 4- to 10-membered heterocyclyloxy; a $C_1$-$C_5$ alkyl substituted by 0 to 7 groups independently selected from halo, CF$_3$, OCF$_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; hydroxy-$C_1$-$C_4$-alkyl, halo-$C_1$-$C_4$ alkoxy, di-$C_1$-$C_4$-alkylamino-$C_1$-$C_4$-alkyl, halo-$C_1$-$C_4$ alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)NR$^{11}$R$^{12}$, CF$_3$, OCF$_3$, and CF$_2$CH$_3$.

In an embodiment, the compound of Formula I is the compound of Formula ID:

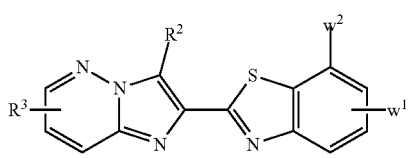

wherein $R^3$ is alkyl, $R^2$ is H, $W^1$ is methoxy and $W^2$ is the moiety:

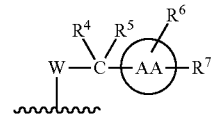

where W is O, $R^4$=$R^5$=H,

is thiazole, $R^6$ is phenyl or morpholino, $R^7$ is H or methyl, and $R^b$ is selected from the group consisting of H, halo, OCF$_3$, OCHF$_2$, OH, CN, NO$_2$, NR$^{11}$R$^{12}$, COOH, $C_1$-$C_4$ alkoxycarbonyl, (C=O)NR$^{11}$R$^{12}$, $C_1$-$C_4$ alkylsulfonyl, S(=O)$_2$NR$^{11}$R$^{12}$, and $C_1$-$C_5$ alkyl substituted by 0 to 7 groups independently selected from halo, CF$_3$, OCF$_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio.

In an embodiment, the compound of Formula I is the compound of Formula IE:

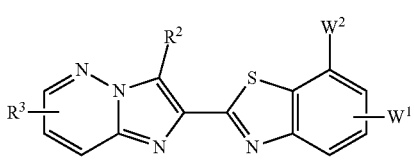

wherein $R^3$ is alkyl, $R^2$ is H, $W^1$ is methoxy and $W^2$ is the moiety:

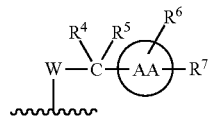

where W is O, $R^4=R^5=H$

is thiazole, $R^7$ is H or methyl, $R^6$ is B—D—, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a linker selected from a single bond, —O—, —S—,

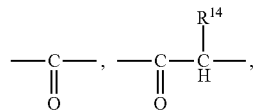

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O), —C(=O)NH—, —SO$_2$—NH—, —NH—SO$_2$—, and $C_2$-$C_6$ alkenylene.

In an embodiment, the compound of Formula I is the compound of Formula IF:

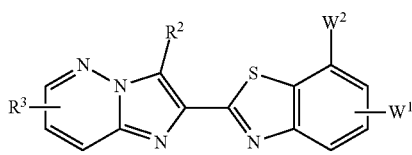

IF wherein $R^3$ is alkyl, $R^2$ is H, $W^1$ is methoxy and $W^2$ is the moiety:

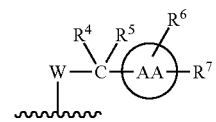

where W is O, $R^4=R^5=H$,

is thiazole, $R^7$ is H or methyl, and $R^6$ is a phenyl which may be optionally substituted with one or more $R^b$, $R^c$, $R^d$ and $R^e$, wherein each of $R^b$, $R^c$, $R^d$ and $R^e$ is independently selected from the group consisting of halo, halo-$C_1$-$C_4$ alkoxy, OH, CN, NO$_2$, =O, NR$^{11}$R$^{12}$, COOH, $C_1$-$C_4$ alkoxy, $C_1$-$C_4$ alkylthio, $C_1$-$C_4$ alkoxycarbonyl, (C=O)NR$^{11}$R$^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2$NR$^{11}$R$^{12}$, N(R$^{13}$)(C=O)NR$^{11}$R$^{12}$, N(R$^{13}$)(C=O)OR$^{14}$, SO$_2$R$^{14}$, N(R$^{13}$)(C=O)R$^{14}$, NR$^{13}$S(O)R$^{14}$, NR$^{13}$SO$_2$R$^{14}$, O(C=O)NR$^{11}$R$^{12}$, O(C=O)OR$^{14}$, O(C=O)R$^{14}$, (C=O)OR$^{14}$, $C_3$-$C_6$ cycloalkyl, a 4- to 10-membered heterocyclyloxy; a $C_1$-$C_5$ alkyl substituted by 0 to 7 groups independently selected from halo, CF$_3$, OCF$_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkyl, 4- to 10-membered heterocyclyloxy, $C_1$-$C_4$-alkylcarbonyloxy and $C_1$-$C_4$ alkylthio; —(CHR$^{13}$)$_n$-5- or 6-membered heteroaryl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; —(CHR$^{13}$)$_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, CF$_3$, OCF$_3$, and CF$_2$CH$_3$; hydroxy-$C_1$-$C_4$-alkyl, halo-$C_1$-$C_4$ alkoxy, di-$C_1$-$C_4$-alkylamino-$C_1$-$C_4$-alkyl, halo-$C_1$-$C_4$ alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)NR$^{11}$R$^{12}$, CF$_3$, OCF$_3$, and CF$_2$CH$_3$;

In yet another embodiment, this invention discloses the compounds listed below:

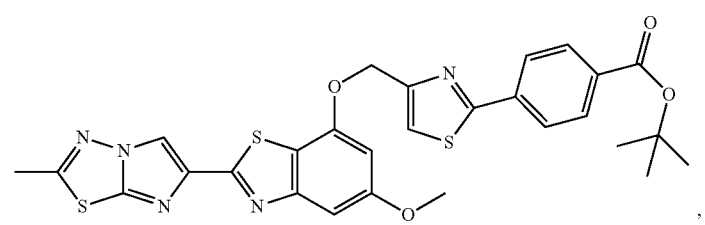

,

-continued
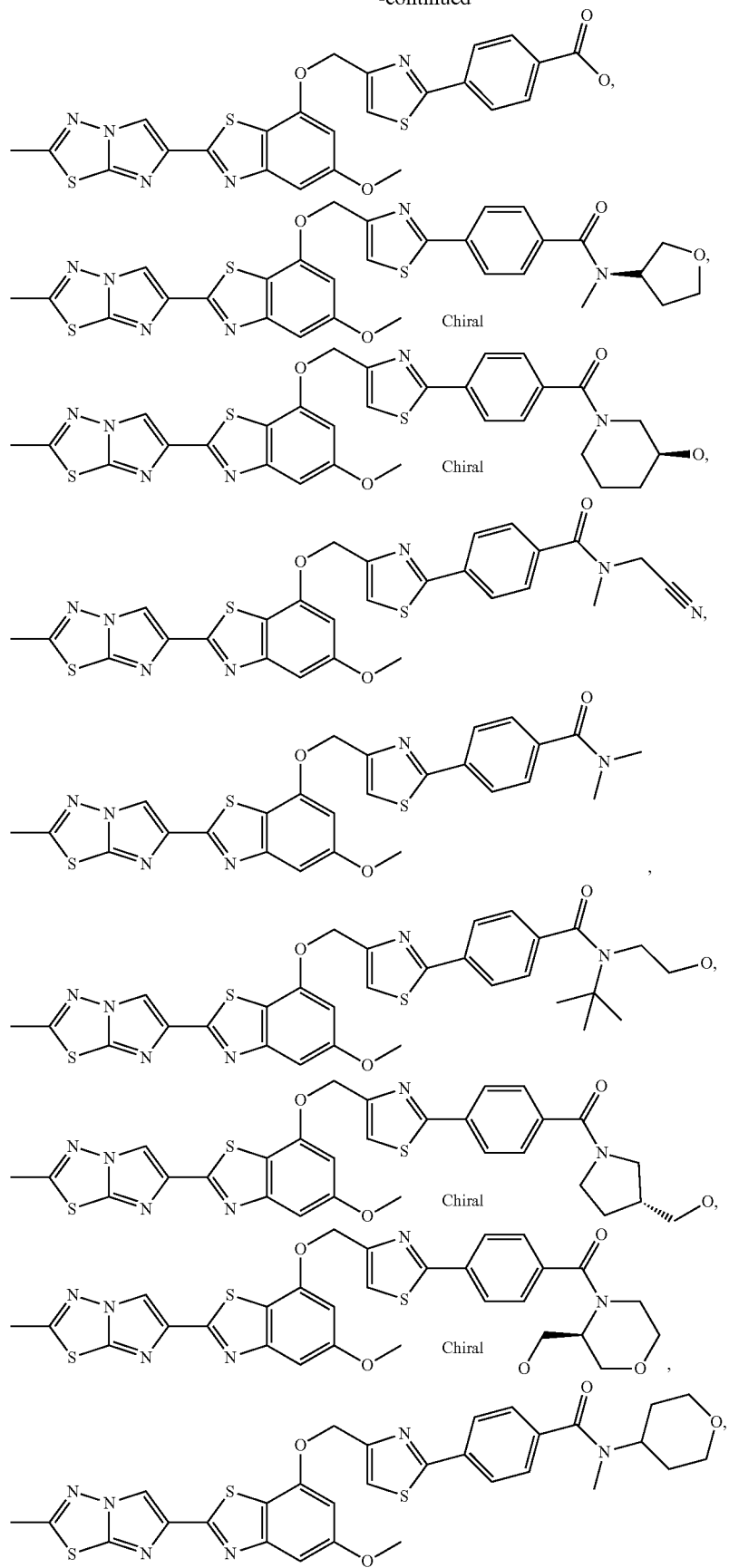

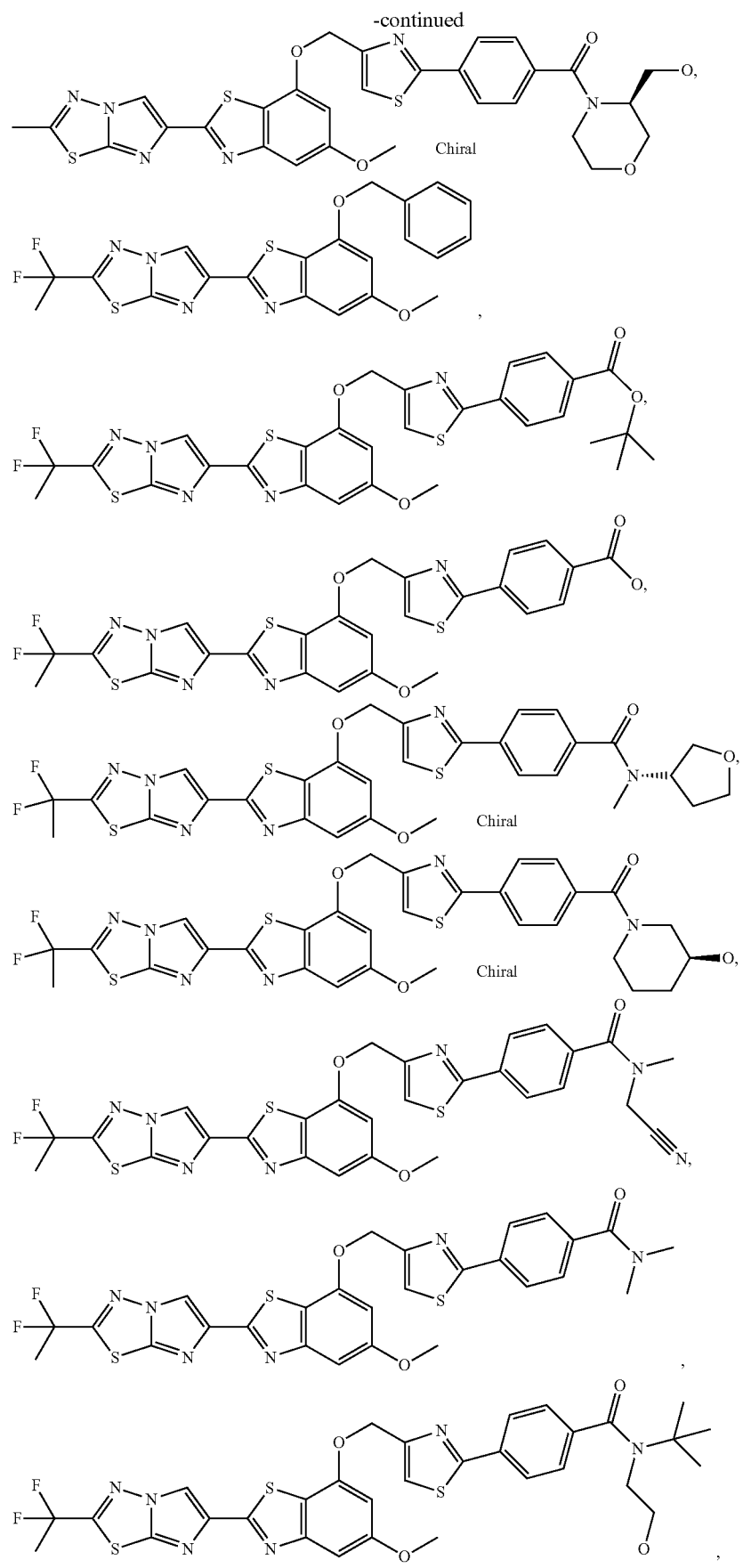

-continued
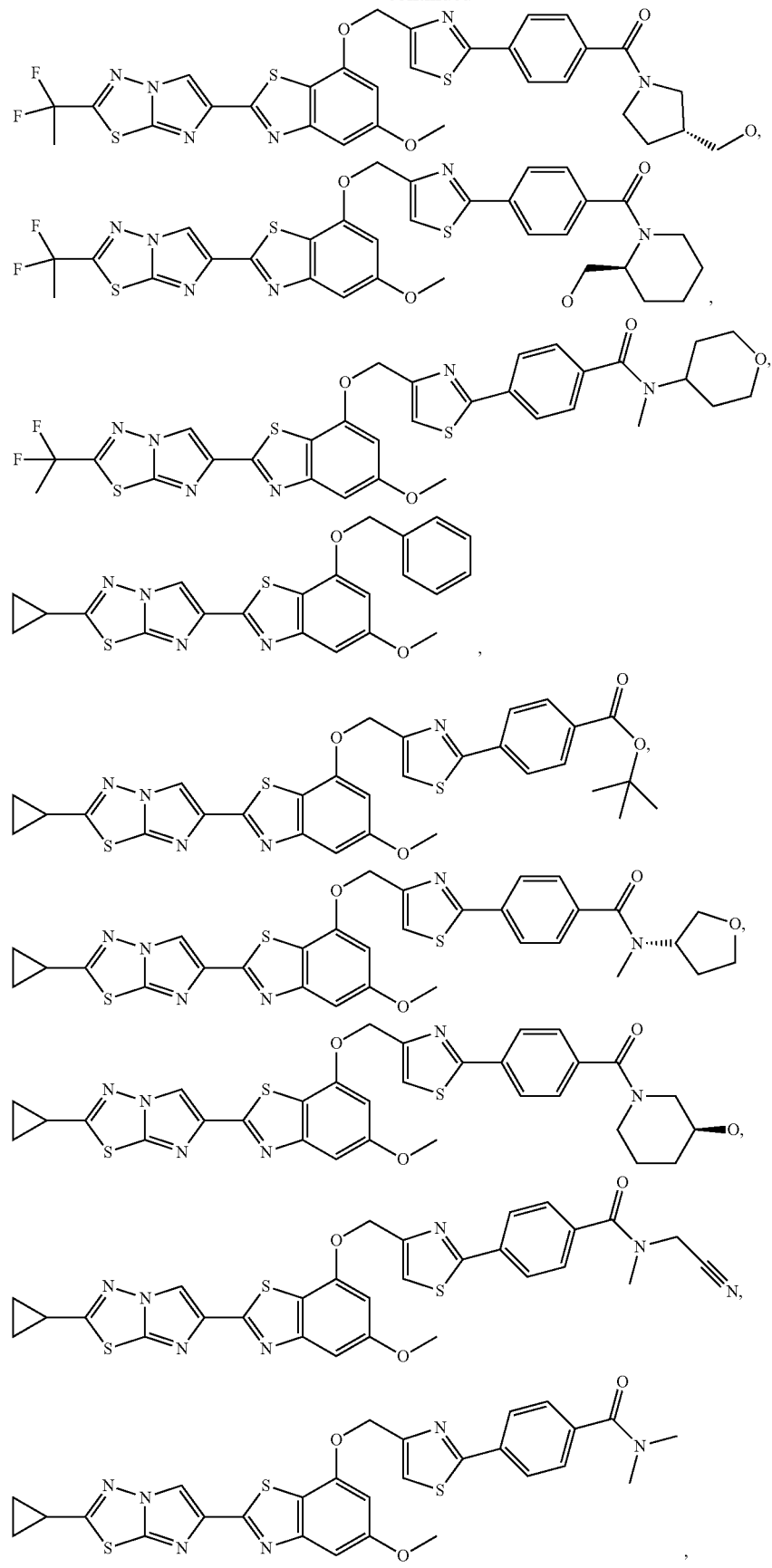

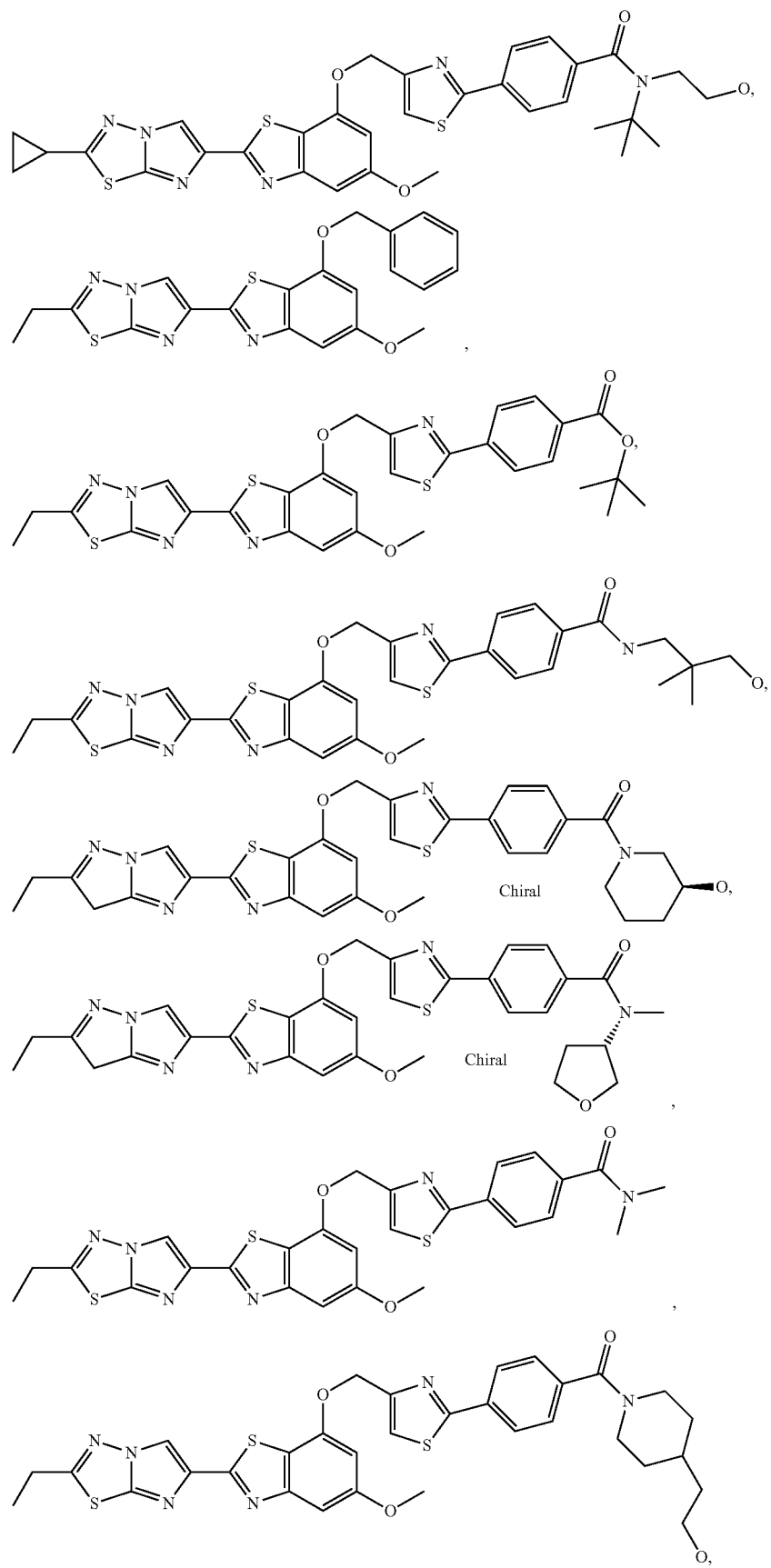

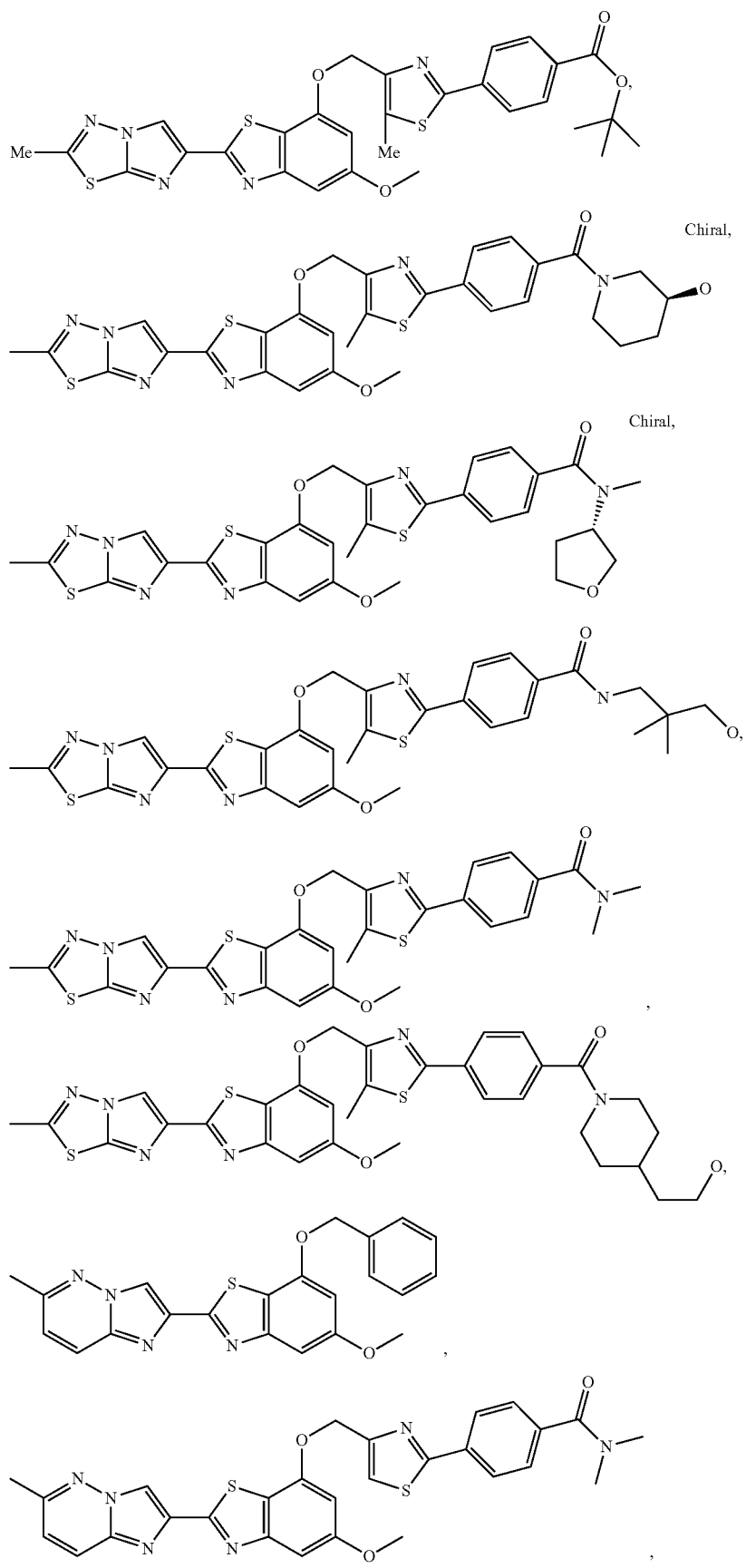

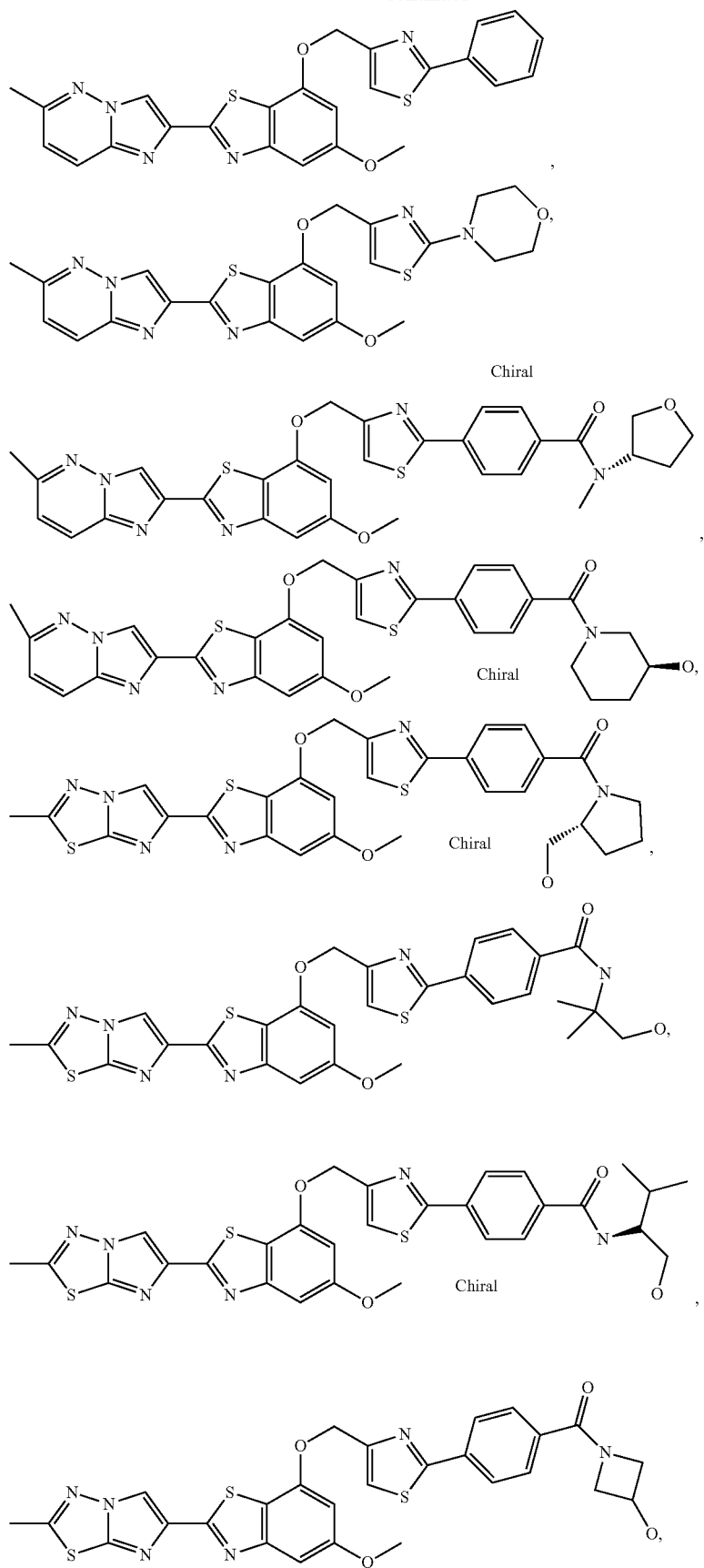

-continued
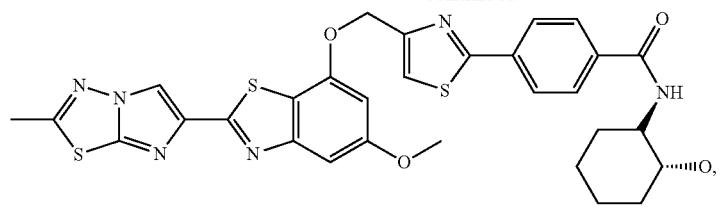
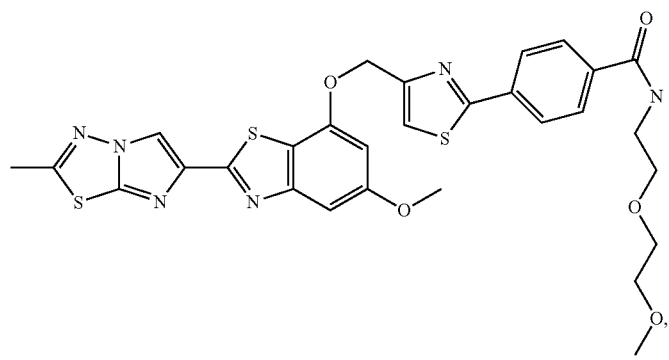
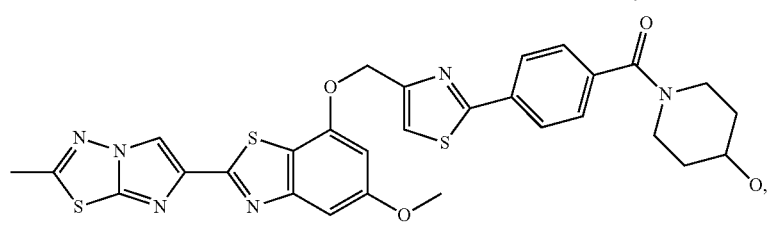
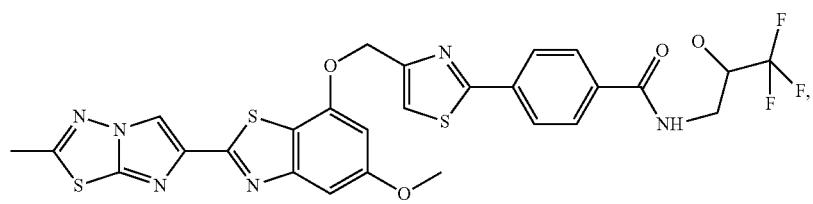
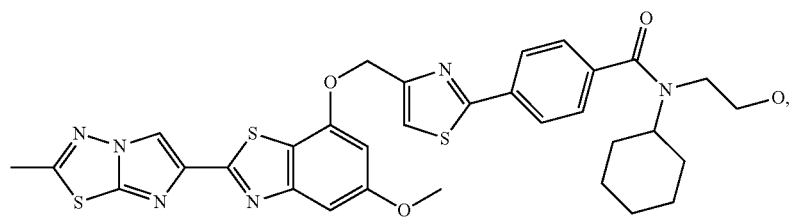
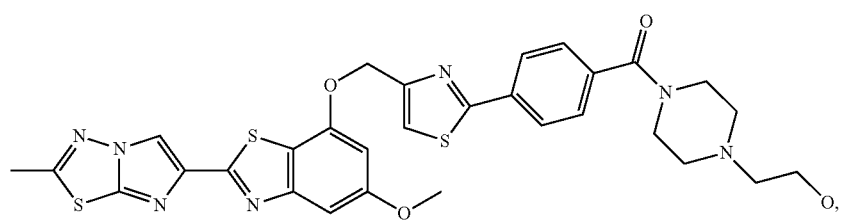
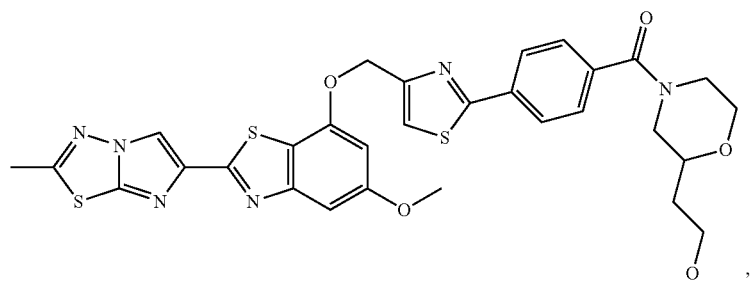

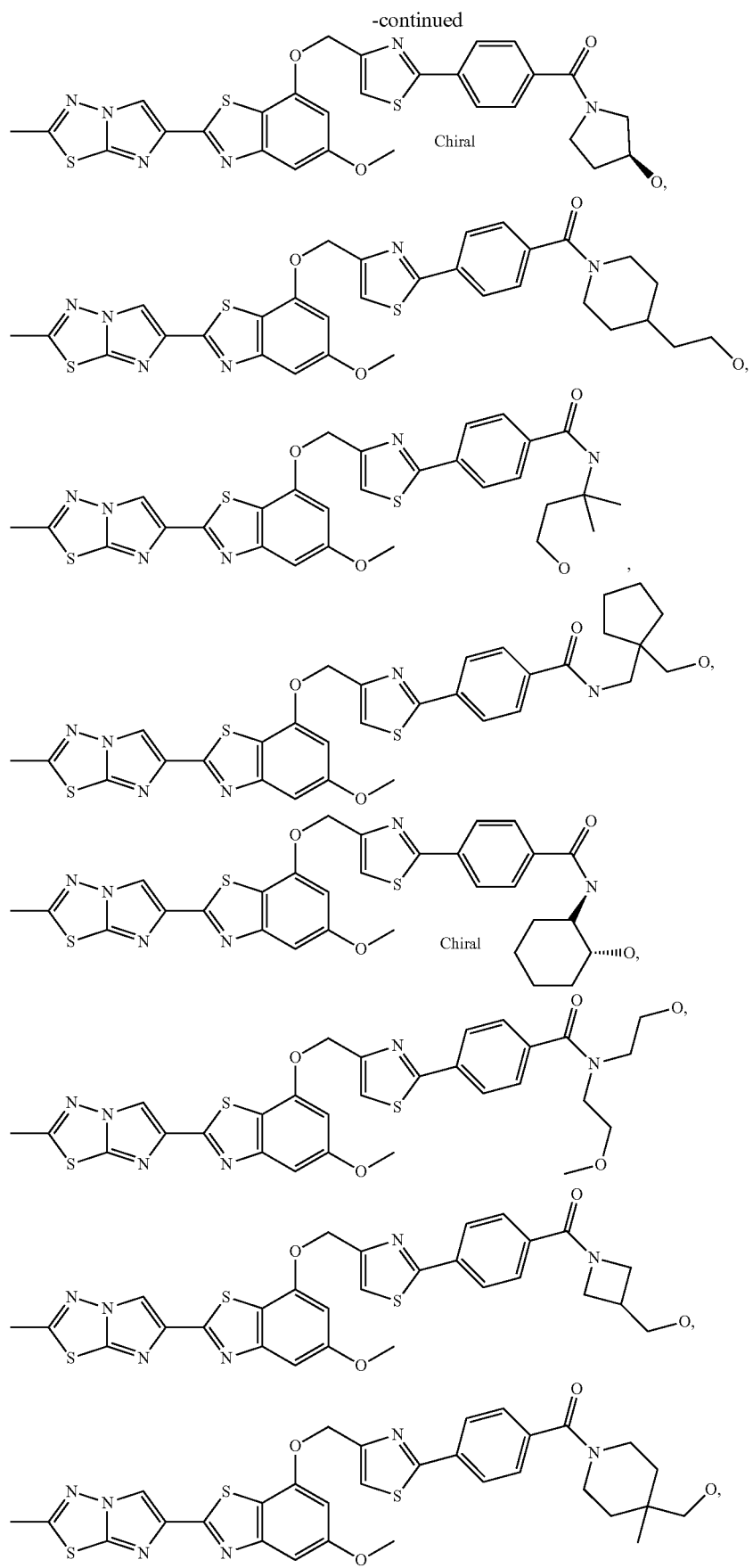

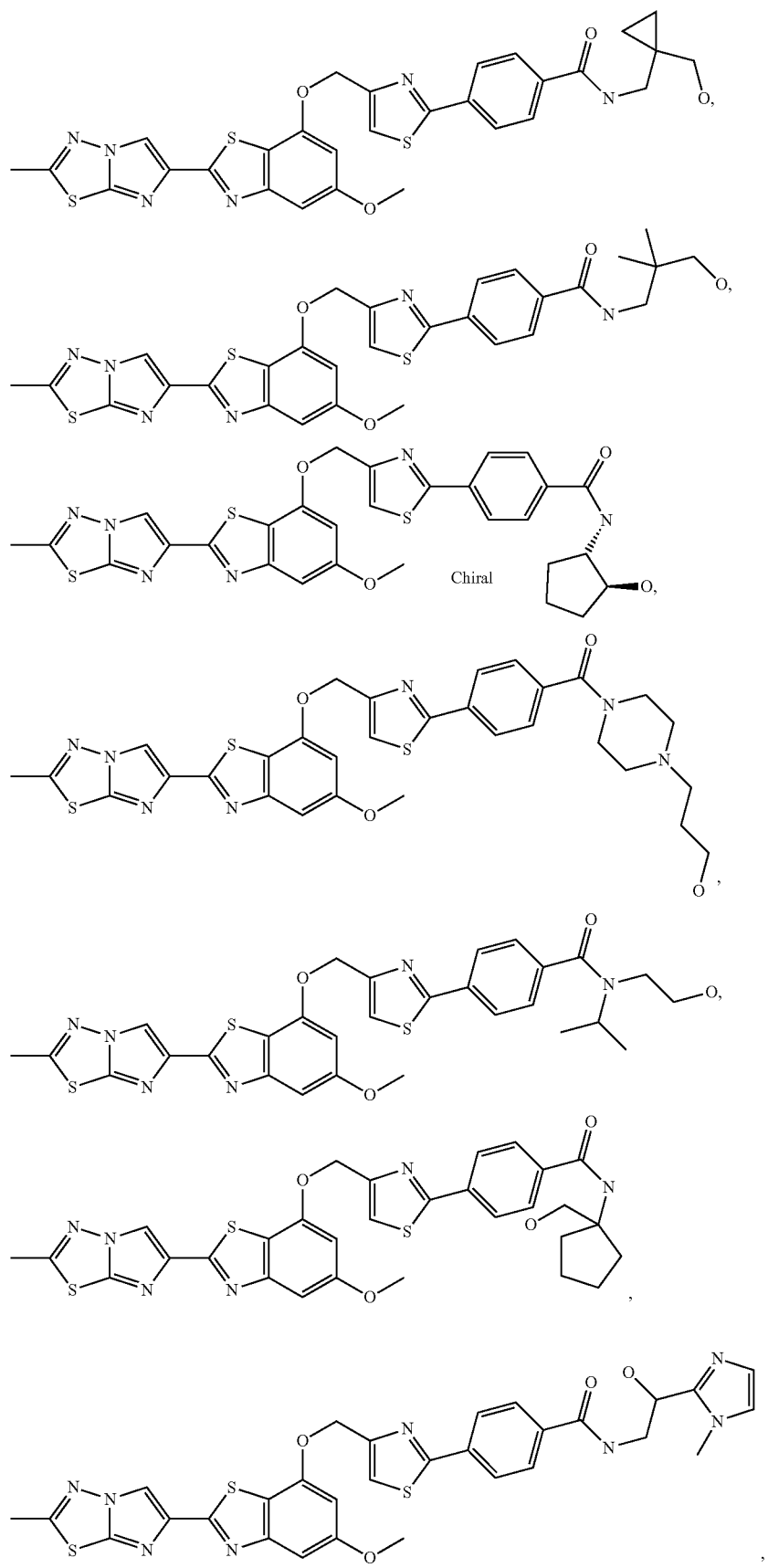

-continued
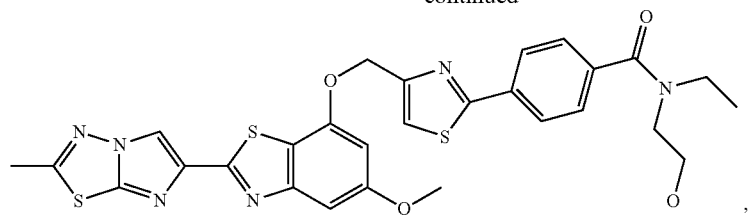
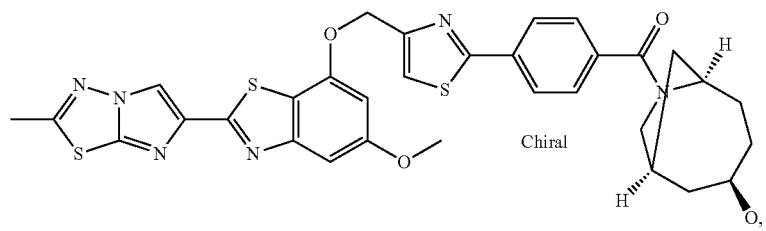
Chiral
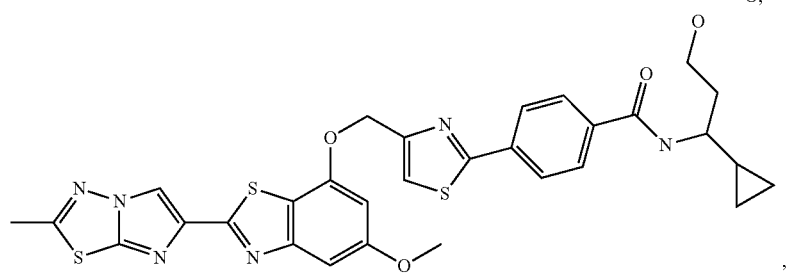
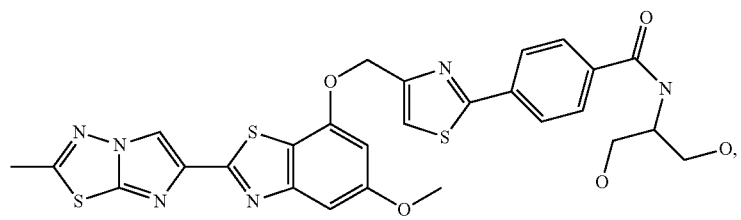
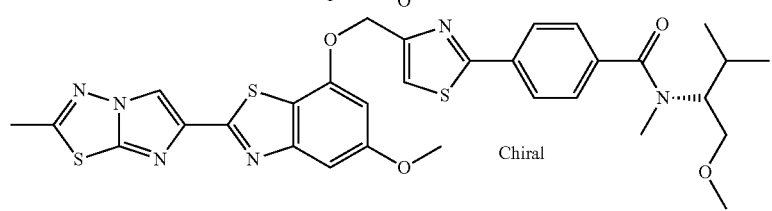
Chiral
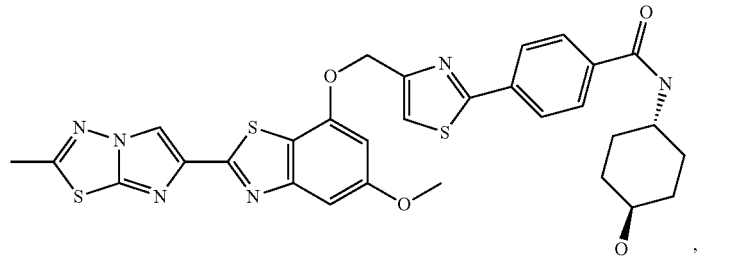
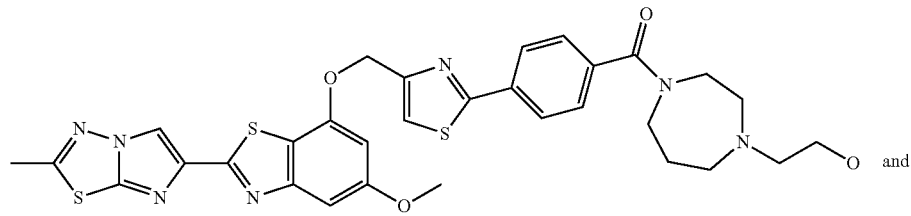
and -continued

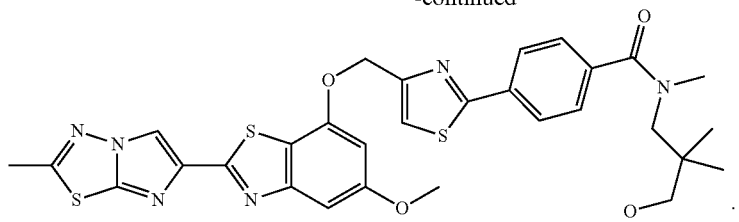

In one embodiment, the present invention provides compounds, stereoisomers, tautomers, salts, solvates or prodrugs thereof, wherein the compounds are compounds of Formula I.

In one embodiment, the present invention provides compounds, stereoisomers, tautomers, salts, solvates or prodrugs thereof, wherein the compounds are compounds of Formula IA.

In one embodiment, the present invention provides compounds, stereoisomers, tautomers, salts, solvates or prodrugs thereof, wherein the compounds are compounds of Formula IB.

In one embodiment, the present invention provides compounds, stereoisomers, tautomers, salts, solvates or prodrugs thereof, wherein the compounds are compounds of Formula IC.

In one embodiment, the present invention provides compounds, stereoisomers, tautomers, salts, solvates or prodrugs thereof, wherein the compounds are compounds of Formula ID.

In one embodiment, the present invention provides compounds, stereoisomers, tautomers, salts, solvates or prodrugs thereof, wherein the compounds are compounds of Formula IE.

In one embodiment, the present invention provides compounds, stereoisomers, tautomers, salts, solvates or prodrugs thereof, wherein the compounds are compounds of Formula IF.

PAR4 compounds of the invention have $IC_{50}$s in the FLIPR Assay (described hereinafter) of about 10 μM, or 5 μM or less, or 500 nM or less, or 10 nM or less. Activity data for selected Example compounds are presented in Table 2 under Example E.

In some embodiments, the present invention provides at least one compound of the present invention or a stereoisomer, tautomer, pharmaceutically acceptable salt, solvate, or prodrug ester thereof.

In some embodiments, the present invention provides one or more compounds of the present invention or a stereoisomer, tautomer, pharmaceutically acceptable salt, solvate, or prodrug ester thereof.

In some embodiments, the present invention provides one or more compounds of compound of Formula I, or Formula IA, or Formula IB, or Formula IC, or Formula ID, or Formula IE, or Formula IF, or, preferably, a compound selected from one of the examples herein, or a stereoisomer, tautomer, pharmaceutically acceptable salt, solvate, or prodrug ester thereof.

In some embodiments, the present invention provides a pharmaceutical composition, which includes a pharmaceutically acceptable carrier and a therapeutically effective amount of at least one compound of Formula I, or Formula IA, or Formula IB, or Formula IC, or Formula ID, or Formula IE, or Formula IF, or, preferably, a compound selected from one of the examples herein, or stereoisomers, tautomers, pharmaceutically acceptable salts, prodrug esters, or solvates thereof, alone or in combination with another therapeutic agent.

In some embodiments, the present invention provides a pharmaceutical composition which includes a therapeutically effective amount of at least one compound of Formula I, or Formula IA, or Formula IB, or Formula IC, or Formula ID, or Formula IE, or Formula IF, and one or more additional therapeutic agent(s). In a preferred embodiment, the present invention provides a pharmaceutical composition, wherein the additional therapeutic agent(s) are an anti-platelet agent or a combination thereof. Preferably, the anti-platelet agent(s) are P2Y12 antagonists and/or aspirin. Preferably, the P2Y12 antagonists are clopidogrel, ticagrelor, or prasugrel. In another preferred embodiment, the present invention provides a pharmaceutical composition, wherein the additional therapeutic agent(s) are an anticoagulant or a combination thereof. Preferably, the anticoagulant agent(s) are FXa inhibitors or thrombin inhibitors. Preferably, the FXa inhibitors are apixaban or rivaroxaban. Preferably, the thrombin inhibitor is dabigatran.

In some embodiments, the present invention provides a method for the treatment or prophylaxis of a thromboembolic disorder which includes the step of administering to a subject (for example, a human) in need of such treatment or prophylaxis a therapeutically effective amount of at least one compound of Formula I, or Formula IA, or Formula IB, or Formula IC, or Formula ID, or Formula IE, or Formula IF, or one of the Examples herein or stereoisomers, tautomers, pharmaceutically acceptable salts, solvates, or prodrug esters thereof.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or a compound selected from one of the Examples herein, or stereoisomers, tautomers, pharmaceutically acceptable salts, prodrug esters, or solvates thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or a compound selected from one of the Examples herein, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, non-ST-elevated myocardial infarction, atrial fibrillation, myocardial infarction, transient ischemic attack, stroke, atherosclerosis, peripheral arterial disease, venous thrombosis, deep vein thrombosis, thrombophlebitis, arterial embolism, coronary arterial thrombosis, cerebral arterial thrombosis, cerebral embolism, kidney embolism, pulmonary embolism, cancer-related thrombosis, and thrombosis resulting from medical implants, devices, and procedures in which blood is exposed to an artificial surface that promotes thrombosis.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or a compound selected from one of the Examples herein, or stereoisomers, tautomers, pharmaceutically acceptable salts, prodrug esters, or solvates thereof, wherein the thromboembolic disorder is selected from the group consisting of acute coronary syndrome, unstable angina, stable angina, ST-elevated myocardial infarction, and non-ST-elevated myocardial infarction.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or a compound selected from one of the Examples herein, or stereoisomers, tautomers, pharmaceutically acceptable salts, prodrug esters, or solvates thereof, wherein the thromboembolic disorder is selected from the group consisting of transient ischemic attack and stroke.

In some embodiments, the present invention provides methods for the treatment of a thromboembolic disorder or the primary or secondary prophylaxis of a thromboembolic disorder, which includes the steps of administering to a patient (for example, a human) in need thereof a therapeutically effective amount of one compound of Formula I, or Formula IA, or Formula IB, or Formula IC, or Formula ID, or Formula IE, or Formula IF, or a compound selected from one of the Examples herein, or stereoisomers, tautomers, pharmaceutically acceptable salts, prodrug esters, or solvates thereof, wherein the thromboembolic disorder is peripheral arterial disease.

In some embodiments, the present invention includes a method as described above wherein the thromboembolic disorder is selected from unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In some embodiments, the present invention includes a method of inhibiting or preventing platelet aggregation, which includes the step of administering to a subject (such as a human) in need thereof a therapeutically effective amount of a PAR4 antagonist, which is a compound of Formula I, or a compound of Formula IA, or a compound of Formula IB, or a compound of Formula IC, or a compound of Formula ID, or a compound of Formula IE, or a compound of Formula IF, or a compound selected from one of the Examples herein, of the invention.

Other Embodiments of the Invention

In some embodiments, the present invention provides a process for making the compounds of the present invention or a stereoisomer, tautomer, pharmaceutically acceptable salt, solvate or prodrug ester thereof.

In some embodiments, the present invention provides an intermediate for making the compounds of the present invention or a stereoisomer, tautomer, pharmaceutically acceptable salt, solvate or prodrug ester thereof.

In some embodiments, the invention provides a method of treatment or prophylaxis of a thromboembolic disorder involving administering to a subject in need thereof (e.g., a human) a therapeutically effective amount of at least one compound that binds to PAR4 (such as a compound of Formula I of the invention) and inhibits PAR4 cleavage and/or signaling, wherein said subject has a dual PAR1/PAR4 platelet receptor repertoire.

In some embodiments, the present invention provides a compound of the present invention or stereoisomers, tautomers, pharmaceutically acceptable salts, solvates, or prodrug esters thereof, for use in therapy for the treatment or prophylaxis of a thromboembolic disorder.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like. "Alkenyl" or "alkenylene", alone or as part of another group, is intended to include hydrocarbon chains of either straight or branched configuration and having one or more carbon-carbon double bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy", alone or as part of another group, refers to an —O-alkyl group, where alkyl is as defined above. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Haloalkyl" is intended to include both branched and straight-chain saturated aliphatic hydrocarbon groups having the specified number of carbon atoms, substituted with at least 1 halogen up to fully substituted with halogens (perhaloalkyl), alternatively 1 to 7 halogens, or 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-$C_1$-$C_2$-alkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring ($C_3$-$C_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, norbornyl,

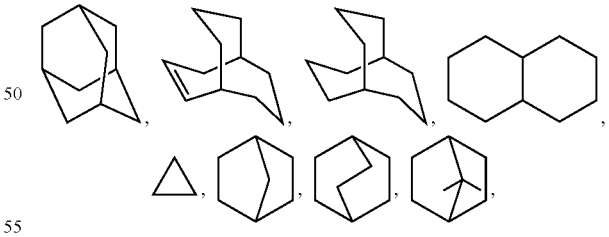

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_{6-10}$ aryl" refers to phenyl and naphthyl. Unless otherwise specified, "aryl", "$C_{6-10}$ aryl" or "aromatic residue" may be unsubstituted or substituted with 1 to 3 groups selected from OH, $C_1$-$C_3$ alkoxy, heterocyclyl, Cl, F, Br, I, CN, $NO_2$, $NH_2$, $N(CH_3)H$, $N(CH_3)_2$, $CF_3$, $OCF_3$, $OCHF_2$, $C(=O)CH_3$, $SCH_3$, $S(=O)CH_3$, $S(=O)_2CH_3$, $S(=O)_2NH_2$, $C_1$-$C_3$ alkyl, $CO_2H$, and $CO_2CH_3$.

As used herein, the term "heterocycle", "heterocyclo" "heterocyclic" or "heterocyclyl" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, $OC_1$-$C_3$ alkoxy, Cl, F, Br, I, CN, $NO_2$, $NH_2$, $N(CH_3)H$, $N(CH_3)_2$, $CF_3$, $OCF_3$, $OCHF_2$, $=O$, $C(=O)CH_3$, $SCH_3$, $S(=O)CH_3$, $S(=O)_2CH_3$, $S(=O)_2NH_2$, $C_1$-$C_3$ alkyl, $CO_2H$ and $CO_2CH_3$. A nitrogen in the heterocycle may optionally be quaternized. The heterocycle may optionally contain a $=O$. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include

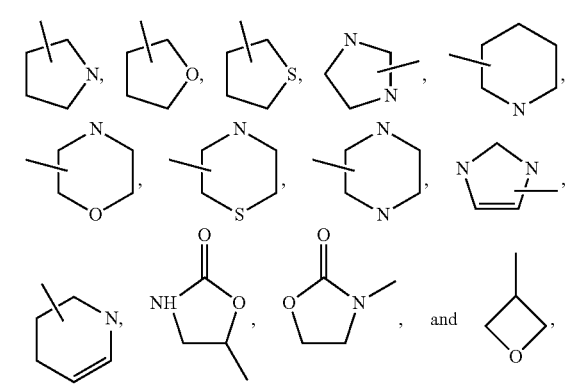

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Heteroaryl groups include, but are not limited to,

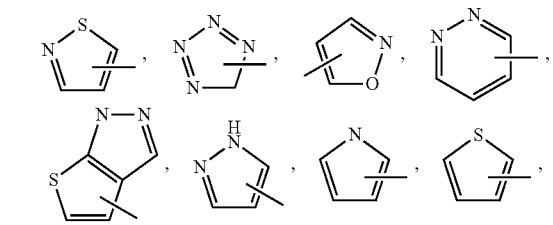

-continued

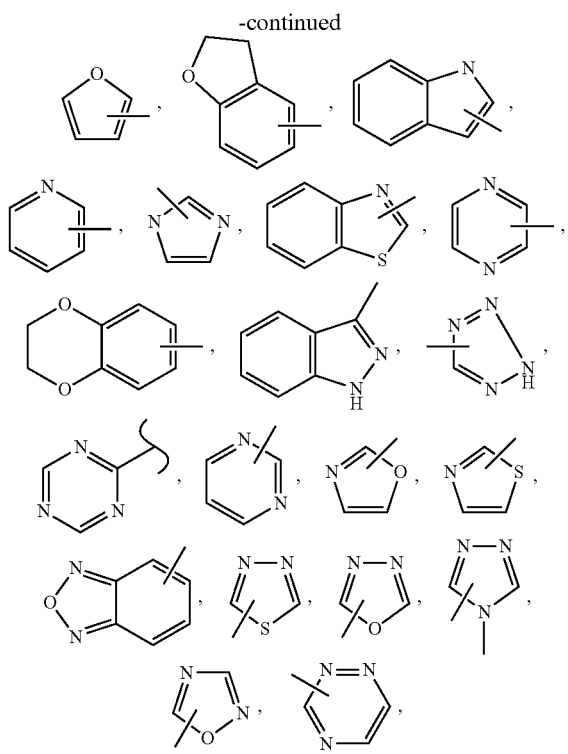

and the like.

When the term "unsaturated" is used herein to refer to a ring or group, which group may be fully unsaturated or partially unsaturated.

The term "acyl" alone or as part of another group refers to a carbonyl group linked to an organic radical, more particularly, the group C(=O)$R_e$, as well as the bivalent groups —C(=O) or C(=O)$R_e$—, which are linked to organic radicals. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, and the like.

The designation

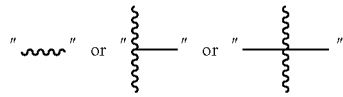

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "counterion" is used to represent a negatively charged species such as chloride, bromide, hydroxide, acetate, and sulfate.

The term "at least one" or "one or more" is used to represent one, or suitable multiples thereof such as, for example, two, three, four, five, six and the like.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When a group or moiety in a structure appears to be short on valence, the remaining valences are understood to be filled with hydrogen atoms unless otherwise stated, e.g. (e.g., —N should be considered —NH$_2$ and —O should be considered —OH, unless otherwise stated).

In cases wherein there are nitrogen atoms (e g, amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{3a}$, then said group may optionally be substituted with up to three $R^{3a}$ groups, and at each occurrence $R^{3a}$ is selected independently from the definition of $R^{3a}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy*, 22nd Edition, Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2nd Edition, reproduced (2006)); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3rd Edition, Academic Press, San Diego, Calif. (2008).

Isotopically labeled compounds of the present invention, i.e., wherein one or more of the atoms described are replaced by an isotope of that atom (e.g., $^{12}C$ replaced by $^{13}C$ or by $^{14}C$; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" for thin layer chromatography, "SM" for starting material, "NMR" for nuclear magnetic resonance spectroscopy, "$^1H$" for proton, "δ" for delta, "s" for singlet, "d" for doublet, "t" for triplet, "q" for quartet, "m" for multiplet, "br" for broad, "Hz" for hertz, and "tlc" for thin layer chromatography. "α", "β", "R", "S", "E", and "Z" are stereochemical designations familiar to one skilled in the art.

| | |
|---|---|
| Me | methyl |
| Et | ethyl |
| Pr | propyl |
| i-Pr | isopropyl |
| Bu | butyl |
| i-Bu | isobutyl |
| t-Bu | tert-butyl |
| Ph | phenyl |
| Bn | benzyl |
| AcOH | acetic acid |
| MeOH | methanol |
| EtOH | ethanol |
| EtOAc | ethyl acetate |
| Et$_2$O | diethyl ether |
| i-PrOH or IPA | isopropanol |
| HOAc | acetic acid |
| BOP reagent | benzotriazol-1-yloxytris(dimethylamino)phosphonium hexafluorophosphate |
| BBr$_3$ | boron tribromide |
| Boc | tert-butyloxycarbonyl |
| cDNA | complimentary DNA |
| CDCl$_3$ | deuterated chloroform |
| CH$_2$Cl$_2$ | dichloromethane |
| CH$_3$CN | acetonitrile |
| ACN | acetonitrile |
| DABCO | 1,4-diazabicyclo[2.2.2]octane |
| DCE | 1,2 dichloroethane |
| DCM | dichloromethane |
| DCC | dicyclohexylcarbodiimide |
| DIAD | diisopropyl azodicarboxylate |
| DIEA or DIPEA | N,N-diisopropylethylamine |
| DME | 1,2-dimethoxyethane |
| DMF | dimethyl formamide |
| DMAP | N,N-dimethylaminopyridine |
| DMSO | dimethyl sulfoxide |
| DPPA | diphenyl phosphoryl azide |
| EDC (or EDC•HCl) or | 3-ethyl-3'-(dimethylamino)propyl-carbodiimide hydrochloride or 1-(3- |

| | |
|---|---|
| EDCI (or EDCI•HCl) or EDAC | dimethylaminopropyl)-3-ethylcarbodiimide hydrochloride |
| EDTA | ethylenediaminetetraacetic acid |
| HATU | O-(7-azabenzotriazol-1-yl)-N,N,N',N'-tetramethyluronium hexafluorophosphate |
| HCl | hydrochloric acid |
| HEPES | 4-(2-hydroxyethyl)piperaxine-1-ethanesulfonic acid |
| Hex | hexane |
| HOBt or HOBT | 1-hydroxybenzotriazole monohydrate |
| Hunig's base | N,N-diisopropylethyl amine |
| LAH | lithium aluminum hydride |
| LDA | Lithium diisopropylamide |
| LiHMDS | Lithium bis(trimethylsilyl) amide |
| mCPBA or m-CPBA | meta-chloroperbenzoic acid |
| NMM | N-methylmorpholine |
| Pd/C | palladium on carbon |
| PPA | polyphosphoric acid |
| PS | polystyrene |
| PXPd2 | bis[di-tert-butyl phosphinous chloride-kP]di-m-chlorodichloro dipalladium |
| PyBOP | (benzotriazol-1-yloxy)tripyrrolidinophosphonium hexafluorophosphate |
| TEA | triethylamine |
| TFA | trifluoroacetic acid |
| THF | tetrahydrofuran |
| TRIS | tris(hydroxymethyl)aminomethane |
| KOAc | potassium acetate |
| $K_3PO_4$ | potassium phosphate |
| $MgSO_4$ | magnesium sulfate |
| NaCl | sodium chloride |
| NaH | sodium hydride |
| $NaHCO_3$ | sodium bicarbonate |
| NaOH | sodium hydroxide |
| $Na_2SO_3$ | sodium sulfite |
| $Na_2SO_4$ | sodium sulfate |
| $NH_3$ | ammonia |
| $NH_4Cl$ | ammonium chloride |
| $NH_4OH$ | ammonium hydroxide |
| OTs | tosylate, para-toluenesulfonate |
| $PBr_3$ | phosphorous tribromide |
| $Pd(PPh_3)_4$ | tetrakis(triphenylphosphine) palladium (0) |
| (S,S)-EtDuPhosRh(I) | (+)-1,2-bis((2S,5S)-2,5-diethylphospholano)benzene (cyclooctadiene)rhodium (I) trifluoromethanesulfonate |

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Wuts et al. (*Greene's Protective Groups In Organic Synthesis*, 4th Edition, Wiley-Interscience (2006)).

Synthesis

Analytical HPLC Method:
Method B
Injection Details: 10 μL of a solution of target compound in methanol
Column: Zorbax XDB-C18, 4.6×30 mm, 3.5 μM
Mobile Phase: Solvent A: 5% MeOH, 95% Water+0.05% TFA, Solvent B: 95% MeOH, 5% Water+0.05% TFA
Mobile Phase: 2 minutes gradient from 0 to 100% solvent B. Last 2 minutes 100% solvent B.
Flow: 3 mL/min, room temperature.
Detector wavelength=220 nM & 254 nM
Preparative HPLC Methods:
Method A
Injection Details: 900 μL of 25 mg/mL in DMF
Column: Zorbax SB-C18 PrepHT, 21.2×100 mm, 5 μM
Mobile Phase: Solvent A: 5% MeOH, 95% Water+0.05% TFA, Solvent B: 95% MeOH, 5% Water+0.05% TFA
Mobile Phase: From 0 to 2 min: isocratic 25% solvent B, followed by a 8 minutes gradient to 100% solvent B. Last 5 minutes 100% solvent B.
Flow: 20 mL/min, room temperature.
Collection wavelength=220 nM.
Method B
Injection Details: 900 μL of 25 mg/mL in DMF
Column: Phenomenex C18, 21.2×150 mm, 5 μM
Mobile Phase: Solvent A: 5% MeOH, 95% Water+0.05% TFA, Solvent B: 95% MeOH, 5% Water+0.05% TFA
Mobile Phase: From 0 to 3 min: isocratic 20% solvent B, followed by a 15 minutes gradient to 100% solvent B. Last 7 minutes 100% solvent B.
Flow: 15 mL/min, room temperature.
Collection wavelength=220 nM.

Scheme 1

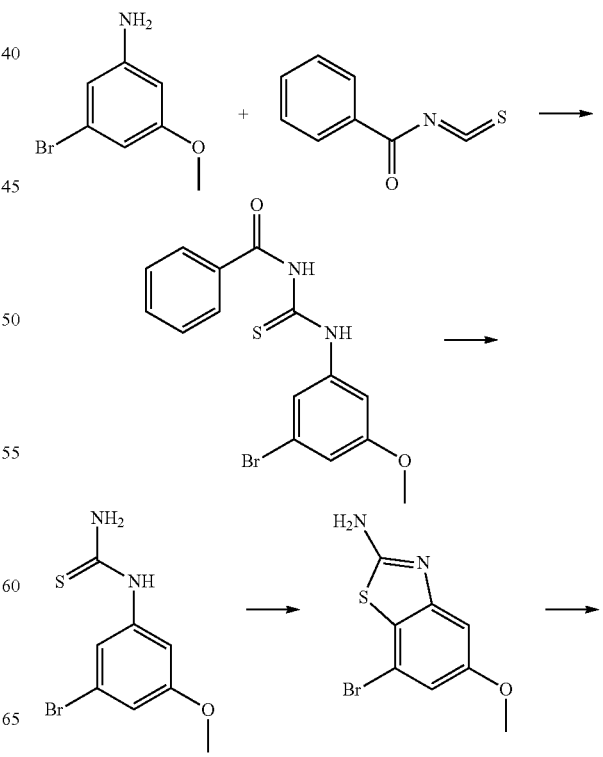

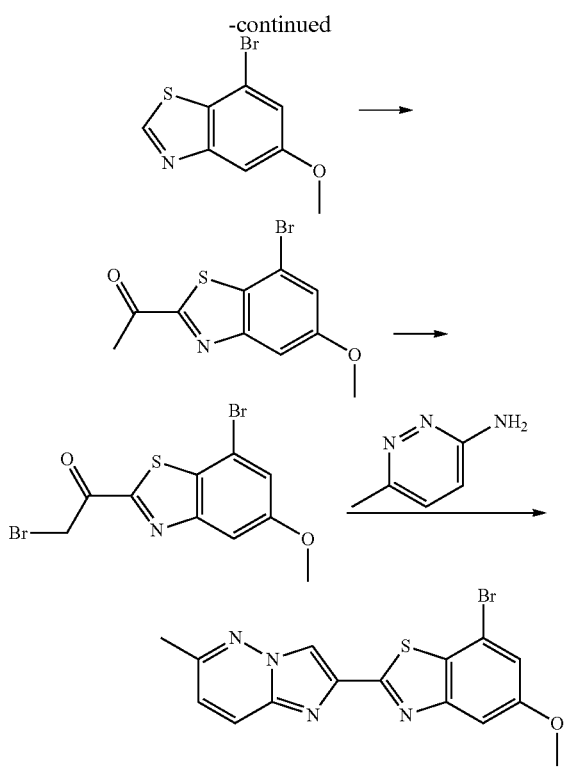

Intermediate A 7-bromo-5-methoxy-2-(6-methylimidazo[1,2-b]pyridazin-2-yl)benzo[d]thiazole

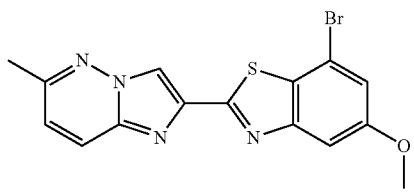

Intermediate AA. N-((3-Bromo-5-methoxyphenyl)carbamothioyl)benzamide

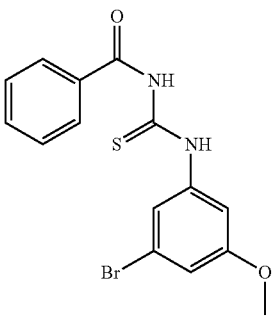 [SMILES: COc1cc(Br)cc(NC(=S)NC(=O)c2ccccc2)c1]

To a solution of 3-bromo-5-methoxyaniline (5.0 g, 25 mmol) stirred in acetone (100 mL) at room temperature, benzoyl isothiocyanate (3.95 mL, 27.2 mmol) was added. The reaction mixture was stirred for 1 hour before the acetone was removed by evaporation. The crude residue obtained was washed with hexanes and collected by filtration to give N-((3-bromo-5-ethoxyphenyl)carbamothioyl)benzamide as a yellow solid (8.0 g, 89%). LC (Method B): 2.351 min MS (APCI): calcd for $C_{15}H_{14}BrN_2O_2S$ [M+H]$^+$ m/z 365.0, 367.0, found 365.0, 367.0. $^1$H NMR (DMSO-d$_6$, 400 MHz) δ ppm 12.57 (br s, 1H), 11.64 (br s, 1H), 7.98 (d, J=7.4 Hz, 2H), 7.67 (t, J=7.4 Hz, 1H), 7.60 (br s, 1H), 7.55 (t, J=7.8 Hz, 2H), 7.34 (br s, 1H), 7.08 (t, J=2.0 Hz, 1H), 3.79 (s, 3H).

Intermediate AB.
1-(3-Bromo-5-methoxyphenyl)thiourea

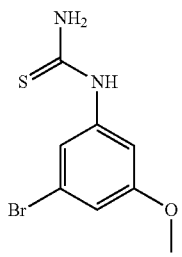

A 350 mL sealed tube was charged with N-((3-bromo-5-methoxyphenyl)carbamothioyl)-benzamide (8.0 g, 21.9 mmol) and THF (150 mL). A solution of sodium hydroxide (4.38 g, 110 mmol) in water (10 mL) was then added and the resulting reaction mixture was stirred at 85° C. for 5 hours. After the mixture had cooled to room temperature, water was added and the product was extracted with ethyl acetate (3×300 mL). The combined organic extracts were washed with brine, dried over MgSO$_4$, filtered and concentrated. The residue obtained was triturated in ethyl acetate and 1-(3-bromo-5-methoxyphenyl)thiourea was collected by filtration and dried in vacuo to give a white solid (2.6 g, 45%). LC (Method B): 1.618 min. MS (APCI): calcd for $C_8H_{10}BrN_2OS$ [M+H]$^+$ m/z 261.0, 263.0, found 261.0, 263.0 $^1$H NMR (DMSO-d$_6$, 400 MHz) δ ppm 9.95 (br s, 1H), 7.70 (br s, 2H), 7.33 (s, 1H), 7.10 (s, 1H), 6.87 (t, J=2.0 Hz, 1H), 3.75 (s, 3H).

Intermediate AC.
7-Bromo-5-methoxybenzo[d]thiazol-2-amine

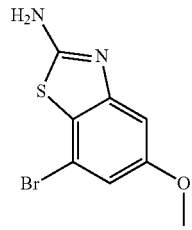

To a solution of 1-(3-bromo-5-methoxyphenyl)thiourea (1.4 g, 5.4 mmol), stirred in chloroform (40 mL) and cooled at −60° C., was added a solution of bromine (0.28 mL, 5.4 mmol) in chloroform (10 mL). The resulting reaction mixture was stirred at room temperature for 15 minutes and then it was heated for 1 h at 70° C. After cooling, the reaction mixture was basified with a saturated aqueous ammonium hydroxide solution and the product was extracted with ethyl acetate (×3). The combined organic extracts were washed with brine, dried over MgSO$_4$, filtered and concentrated to give 7-bromo-5-methoxybenzo[d]thiazol-2-amine as an off white solid (1.27 g, 91%). The product obtained was used as such for the next step. LC (Method B): 1.686 min. MS (APCI): calcd for C$_8$H$_8$BrN$_2$OS [M+H]$^+$ m/z 259.0, 261.0, found 259.0, 261.0 $^1$H NMR (DMSO-d$_6$, 400 MHz) δ ppm 7.69 (br s, 2H), 6.90 (d, J=2.0 Hz, 1H), 6.84 (d, J=2.4 Hz, 1H), 3.76 (s, 3H).

Intermediate AD.
7-bromo-5-methoxybenzo[d]thiazole

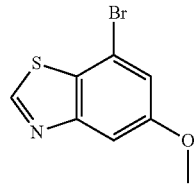

To a suspension of 7-bromo-5-methoxybenzo[d]thiazol-2-amine (500 mg, 1.930 mmol) in dioxane (20 mL) under nitrogen, was added isopentyl nitrite (0.52 mL, 3.9 mmol). The resulting mixture was heated at 85° C. for 1.5 hour. After cooling, the crude mixture was concentrated under reduced pressure and the crude residue obtained was purified by column chromatography (40 g cartridge). Elution with a gradient of ethyl acetate in dichloromethane (from 0 to 50%) afforded 7-bromo-5-methoxybenzo[d]thiazole as a white solid (297 mg, 63%). LC (Method B): 2.074 min MS (APCI): calcd for C$_8$H$_7$BrNOS [M+H]$^+$ m/z 244.0, 246.0, found 244.0, 246.0 $^1$H NMR (DMSO-d$_6$, 400 MHz) δ ppm 9.46 (s, 1H), 7.67 (d, J=2.0 Hz, 1H), 7.41 (d, J=2.3 Hz, 1H), 3.87 (s, 3H).

Intermediate AE. 1-(7-Bromo-5-methoxybenzo[d]thiazol-2-yl)ethanone

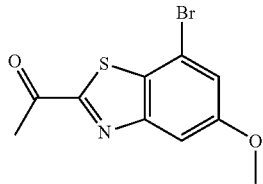

To a solution of 7-bromo-5-methoxybenzo[d]thiazole (297 mg, 1.22 mmol), stirred at −78° C. in THF (10 mL), was added a 1.0M THF solution of LiHMDS (3.0 mL, 3.0 mmol). The resulting reaction mixture was for stirred 5 min before N-methoxy-N-methylacetamide (0.14 mL, 1.3 mmol) was added. After the addition, the reaction mixture was stirred for another 25 min and then it was quenched with a saturated aqueous solution of ammonium chloride and allowed to warm to room temperature. The resulting mixture was extracted with ethyl acetate (×3) and the combined organic extracts were washed with brine, dried over MgSO$_4$, filtered and concentrated to give 1-(7-bromo-5-methoxy-benzo[d]thiazol-2-yl)ethanone as a yellow solid (242 mg, 69%). The product obtained was used as such for the next step. LC (Method B): 2.282 min. MS (APCI): calcd for C$_{10}$H$_9$BrNO$_2$S [M+H]$^+$ m/z 286.0, 288.0, found 286.0, 288.0. $^1$H NMR (DMSO-d$_6$, 400 MHz) δ ppm 7.83 (d, J=2.0 Hz, 1H), 7.57 (d, J=2.3 Hz, 1H), 3.90 (s, 3H), 2.73 (s, 3H).

Intermediate AF. 2-Bromo-1-(7-bromo-5-methoxy-benzo[d]thiazol-2-yl)ethanone

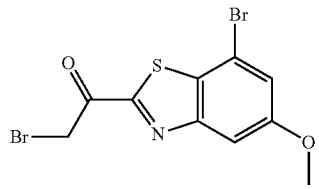 [SMILES: COc1cc(Br)c2sc(C(=O)CBr)nc2c1]

In a sealed tube, phenyltrimethylammonium tribromide (477 mg, 1.27 mmol) was added to a solution of 1-(7-bromo-5-methoxybenzo[d]thiazol-2-yl)ethanone (242 mg, 0.850 mmol) stirred in dry THF (10 mL). The resulting reaction mixture was heated at 65° C. for 12 h, allowed to cool and then filtered. The filter-cake was washed with ether and the filtrate was concentrated to give a crude residue. Purification by column chromatography (25 g cartridge), eluting with a gradient of dichloromethane in hexanes (from 0 to 40%), gave 2-bromo-1-(7-bromo-5-methoxybenzo[d]thiazol-2-yl)ethanone as a yellow solid (222 mg, 72%). LC (Method B): 2.341 min. MS (APCI): calcd for C$_{10}$H$_8$Br$_2$NO$_2$S [M+H]$^+$ m/z 365.9, found 365.9. $^1$H NMR (DMSO-d$_6$, 400 MHz) δ ppm 7.84 (d, J=2.0 Hz, 1H), 7.60 (d, J=2.3 Hz, 1H), 5.04 (s, 2H), 3.91 (s, H).

Intermediate A. 7-Bromo-5-methoxy-2-(6-methyl-imidazo[1,2-b]pyridazin-2-yl)benzo[d]thiazole

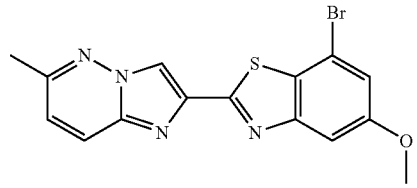

A sealed tube was charged with 6-methylpyridazin-3-amine (80 mg, 0.73 mmol), 2-bromo-1-(7-bromo-5-methoxybenzo[d]thiazol-2-yl)ethanone (222 mg, 0.610 mmol) and ethanol (7.5 mL). The resulting suspension was heated overnight at 85° C. in an oil bath. After cooling, the crude reaction mixture was concentrated under reduced pressure. The crude residue obtained was dissolved in dichloromethane and washed with a saturated sodium bicarbonate solution and brine, dried over MgSO$_4$, filtered and concentrated. The crude residue obtained was purified by column chromatography (25 g cartridge) eluting with a gradient of ethyl acetate in dichloromethane (from 0 to 50%) to give 7-bromo-5-methoxy-2-(6-methylimidazo[1,2-b]pyridazin-2-yl)benzo[d]thiazole as a white solid (108 mg, 47%). LC (Method B): 2.339 min. MS (APCI): calcd for C$_{15}$H$_{12}$BrN$_4$OS [M+H]$^E$ m/z 375.0, 377.0, found 375.0, 377.0. $^1$H NMR (DMSO-d$_6$, 400 MHz) δ ppm 8.86 (s, 1H), 8.14 (d, J=9.4 Hz, 1H), 7.62 (d, J=2.3 Hz, 1H), 7.37 (d, J=2.3 Hz, 1H), 7.29 (d, J=9.4 Hz, 1H), 3.88 (s, 3H), 2.57 (s, 3H).

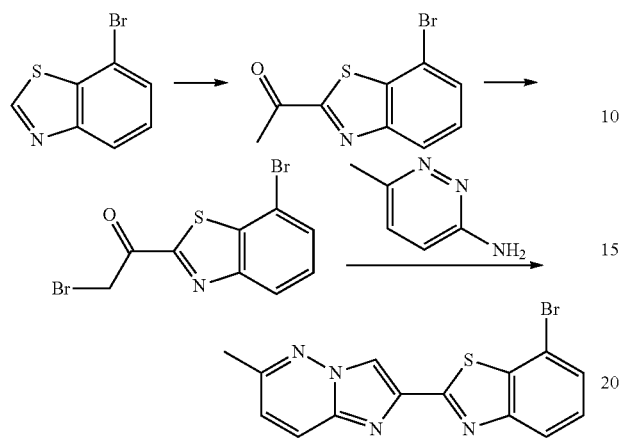

Intermediate B 7-bromo-2-(6-methylimidazo[1,2-b]pyridazin-2-yl)benzo[d]thiazole

Intermediate BA.
1-(7-Bromobenzo[d]thiazol-2-yl)ethanone

To a solution of 7-bromobenzo[d]thiazole (250 mg, 1.17 mmol) stirred at −78° C. in THF (10 mL) was added a 1.0M THF solution of LiHMDS (2.9 mL, 2.9 mmol). The resulting reaction mixture was stirred for 5 min before N-methoxy-N-methylacetamide (0.14 ml, 1.3 mmol) was added. After addition, the reaction was stirred for another 35 min and then it was quenched with a saturated aqueous solution of ammonium chloride and warmed to room temperature. The mixture was extracted with ethyl acetate (×3) and the combined organic extracts were washed with brine, dried over MgSO$_4$, filtered and concentrated. The crude residue obtained was purified by column chromatography (25 g cartridge), eluting with a gradient of dichloromethane in hexanes (from 0 to 100%), to give 1-(7-bromobenzo[d]thiazol-2-yl)ethanone as a white solid (257 mg, 86%). LC (Method B): 2.148 min. MS (APCI): calcd for C$_9$H$_7$BrNOS [M+H]$^+$ m/z 255.9, 257.9, found 256.0, 258.0. $^1$H NMR (DMSO-d$_6$, 400 MHz) δ ppm 8.30 (d, J=8.2 Hz, 1H), 7.89 (d, J=7.8 Hz, 1H), 7.64 (t, J=8.2 Hz, 1H), 2.76 (s, 3H).

Intermediate BB. 2-Bromo-1-(7-bromobenzo[d]thiazol-2-yl)ethanone

Phenyltrimethylammonium tribromide (446 mg, 1.19 mmol) was added to a solution of 1-(7-bromobenzo[d]thiazol-2-yl)ethanone (253 mg, 0.99 mmol) stirred in dry THF (10 mL) in a sealed tube and the resulting mixture was heated at 65° C. for 16 h. After cooling, the solid was removed by filtration, the filtrate was concentrated and the crude residue was purified by column chromatography (25 g cartridge). Elution with a gradient of dichloromethane in hexanes (from 0 to 100%) gave 2-bromo-1-(7-bromobenzo[d]thiazol-2-yl)ethanone as an off-white solid (184 mg, 80%). LC (Method B): 2.240 min. MS (APCI): calcd for C$_9$H$_6$Br$_2$NOS [M+H]$^+$ m/z 335.9, found: 335.9. $^1$H NMR (DMSO-d$_6$, 400 MHz) δ ppm 8.32 (d, J=8.2 Hz, 1H), 7.93 (dd, J=0.8, 7.8 Hz, 1H), 7.66 (t, J=8.2 Hz, 1H), 5.09 (s, 2H).

Intermediate B. 7-Bromo-2-(6-methylimidazo[1,2-b]pyridazin-2-yl)benzo[d]thiazole A sealed tube was charged with 6-methylpyridazin-3-amine (115 mg, 1.06 mmol), 2-bromo-1-(7-bromobenzo[d]thiazol-2-yl)ethanone (363 mg, 0.85 mmol) and ethanol (20 mL) and the resulting suspension was heated at 80° C. overnight. After cooling, the crude reaction mixture was concentrated under reduced pressure and the residue was dissolved in dichloromethane and washed with saturated aqueous sodium bicarbonate and brine, dried over MgSO$_4$, filtered and concentrated. The crude residue obtained was triturated with ethanol and the solid was collected by filtration and dried in vacuo to give 7-bromo-2-(6-methylimidazo[1,2-b]pyridazin-2-yl)benzo[d]thiazole as a red solid (217 mg, 74%). LC (Method B): 2.299 min MS (APCI): calcd for C$_{14}$H$_{10}$BrN$_4$S [M+H]$^+$ m/z 347.0, 345.0, found: 347.0, 345.0. $^1$H NMR (DMSO-d$_6$, 400 MHz) δ ppm 8.93 (s, 1H), 8.15 (d, J=9.4 Hz, 1H), 8.06 (d, J=8.2 Hz, 1H), 7.70 (d, J=7.8 Hz, 1H), 7.52 (t, J=7.8 Hz, 1H), 7.30 (d, J=9.4 Hz, 1H), 2.57 (s, 3H).

Scheme 3
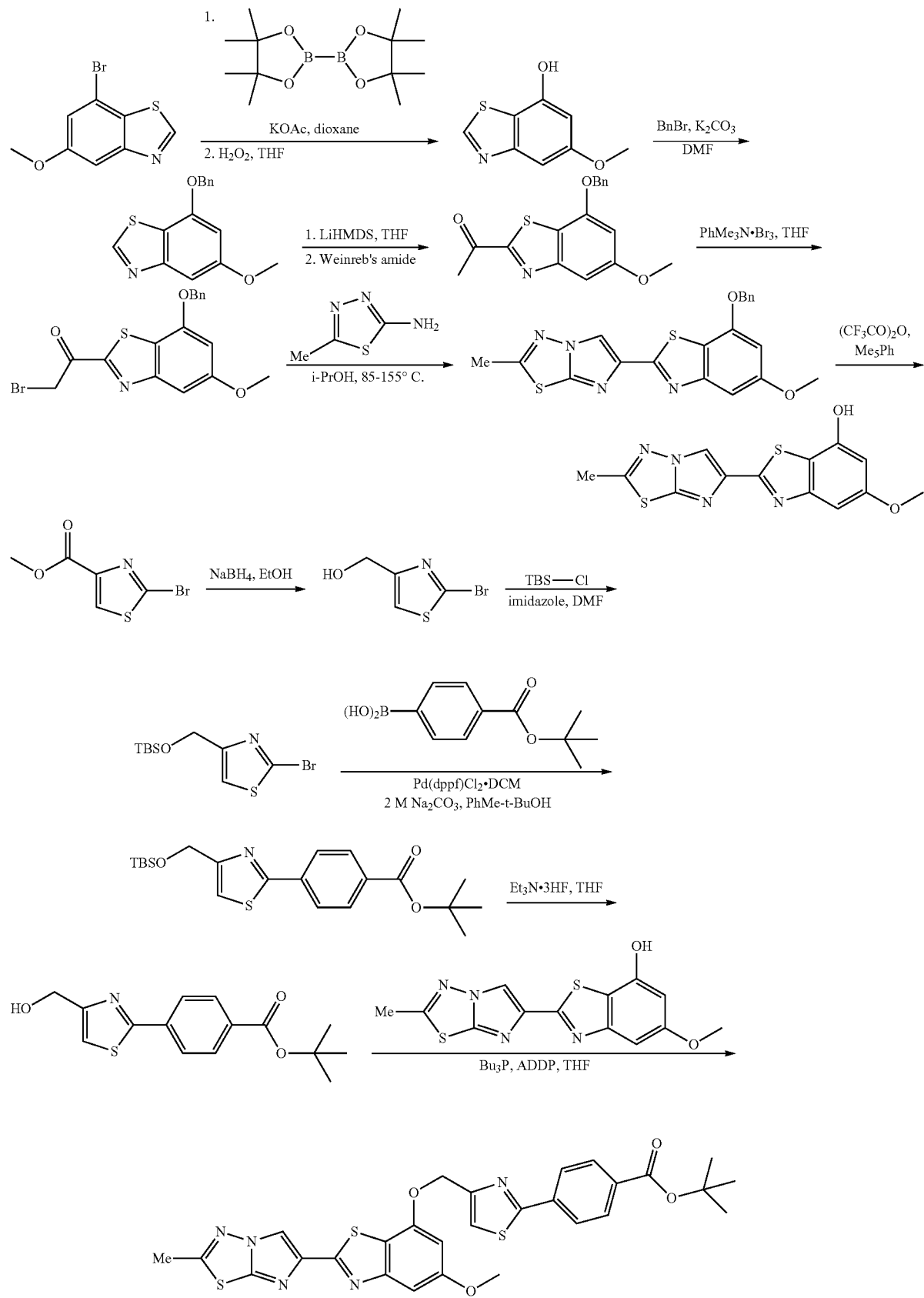

Example 1 tert-Butyl 4-(4-(((5-methoxy-2-(2-methylimidazo[2,1-b][1,3,4]thiadiazol-6-yl)benzo[d]thiazol-7-yl)oxy)methyl)thiazol-2-yl)benzoate

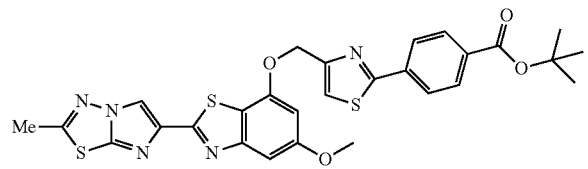 [SMILES: COc1cc(OCc2csc(-c3ccc(C(=O)OC(C)(C)C)cc3)n2)c2sc(-c3cn4nc(C)sc4n3)nc2c1]

Intermediate 1A. 5-Methoxybenzo[d]thiazol-7-ol

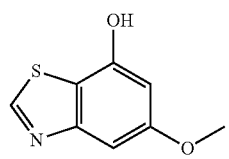

To a stirred solution of 7-bromo-5-methoxybenzo[d]thiazole (Intermediate AD, 1.34 g, 5.49 mmol) in anhydrous 1,4-dioxane (25 mL) was added potassium acetate (1.62 g, 16.5 mmol) and bis(pinacolato)diboron (3.48 g, 13.7 mmol) and PdCl$_2$(dppf) (0.402 g, 0.549 mmol). The reaction mixture was degassed with nitrogen then heated at 80° C. for 16 h. The reaction mixture was filtered over Celite to remove the solids and the filtrate was concentrated to dryness to give a black oil. The oil was dissolved in THF (25 mL), cooled to 0° C. (ice water bath) and charged with 30% H$_2$O$_2$ (10 mL). The reaction mixture was stirred for 1.5 h before being concentrated to dryness. The residue was purified on ISCO using a REDISEP® 80 g column (DCM/EtOAc). to give an impure brown oil. This material was repurified using a REDISEP® 80 g column (hexanes/EtOAc) to give 5-methoxybenzo[d]thiazol-7-ol (0.900 g, 4.97 mmol, 90%) as a white solid. LC (Method B): 1.388 min. MS (APCI): calcd for C$_8$H$_8$NO$_2$S [M+H]$^+$ m/z 182.0, found 182.1. $^1$HNMR (400 MHz, DMSO-d$_6$) δ ppm 10.59 (s, 1H), 9.27 (s, 1H), 7.12 (d, J=2.3 Hz, 1H), 6.50 (d, J=2.0 Hz, 1H), 3.80 (s, 3H).

Intermediate 1B. 7-(Benzyloxy)-5-methoxybenzo[d]thiazole

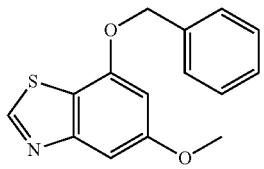 [SMILES: COc1cc(OCc2ccccc2)c2scnc2c1]

To a stirred solution of 5-methoxybenzo[d]thiazol-7-ol (900 mg, 4.97 mmol) and K$_2$CO$_3$ (755 mg, 5.46 mmol) in DMF (10 mL) was added benzyl bromide (0.591 mL, 4.97 mmol) dropwise over a period of 10 min. The reaction mixture was stirred at room temperature for 1 h and then it was filtered to remove the solid material. The filtrate was partitioned between EtOAc-water and the organic phase was separated, dried (MgSO$_4$), filtered and concentrated to dryness. The residue was purified on ISCO using a REDISEP® 40 g column (hexanes/EtOAc) to give 7-(benzyloxy)-5-methoxybenzo[d]thiazole (552 mg, 2.03 mmol, 41%) as a clear, pale yellow oil. LC (Method B): 2.168 min. MS (APCI): calcd for C$_{15}$N$_{14}$NO$_2$S [M+H]$^+$ m/z 272.1, found 272.1. $^1$HNMR (400 MHz, DMSO-d$_6$) δ ppm 9.33 (s, 1H), 7.48 (m, 2H), 7.42 (m, 2H), 7.35 (m, 1H), 7.25 (d, J=2.3 Hz, 1H), 6.80 (d, J=2.0 Hz, 1H), 5.31 (s, 2H), 3.84 (s, 3H).

Intermediate 1C. 1-(7-(Benzyloxy)-5-methoxybenzo[d]thiazol-2-yl)ethanone

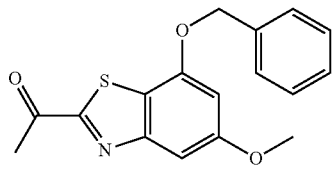 [SMILES: COc1cc(OCc2ccccc2)c2sc(C(C)=O)nc2c1]

To a stirred solution of 7-(benzyloxy)-5-methoxybenzo[d]thiazole (2.73 g, 10.1 mmol) in dry THF (75 mL), at −78° C. under nitrogen, was added LiHMDS (1 M in THF, 25.2 mL, 25.2 mmol). The reaction mixture was stirred for 5 minutes after which N-methoxy-N-methylacetamide (1.28 mL, 12.1 mmol) was added. The reaction mixture was stirred for 25 minutes, quenched with saturated aqueous NH$_4$Cl then extracted with ethyl acetate (100 mL). The organic phase was washed with brine, dried (MgSO$_4$), filtered and concentrated to dryness. The residue was purified on ISCO using a REDISEP® 80 g column (hexanes/EtOAc) to give 1-(7-(benzyloxy)-5-methoxybenzo[d]thiazol-2-yl)ethanone (2.27 g, 7.24 mmol, 72%). LC (Method B): 2.331 min. MS (APCI): calcd for C$_{17}$H$_{16}$NO$_3$S [M+H]$^+$ m/z 314.1, found 314.1. $^1$HNMR (400 MHz, DMSO-d$_6$) δ ppm 7.49 (m, 2H), 7.42 (m, 2H), 7.40 (d, J=2.0 Hz, 1H), 7.35 (m, 1H), 6.94 (d, J=2.0 Hz, 1H), 5.35 (s, 2H), 3.86 (s, 3H), 2.73 (s, 3H).

Intermediate 1D. 1-(7-(Benzyloxy)-5-methoxybenzo[d]thiazol-2-yl)-2-bromoethanone

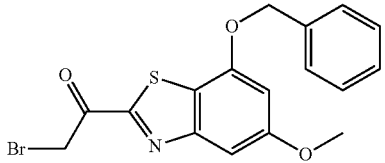 [SMILES: COc1cc(OCc2ccccc2)c2sc(C(=O)CBr)nc2c1]

Phenyltrimethylammonium tribromide (2.72 g, 7.24 mmol) was added to a solution of 1-(7-(benzyloxy)-5-methoxybenzo[d]thiazol-2-yl)ethanone (2.27 g, 7.24 mmol) stirred in THF (25 mL) in a sealed tube. The resulting reaction mixture was stirred at ambient temperature for 1 h and then it was filtered and the solid material was rinsed with ethyl acetate. The filtrate was concentrated to dryness to give 1-(7-(benzyloxy)-5-methoxybenzo[d]thiazol-2-yl)-2-bromoethanone (2.84 g, 7.24 mmol, 100%) as a yellow solid which was used as such without further purification.

Intermediate 1E. 7-(Benzyloxy)-5-methoxy-2-(2-methylimidazo[2,1-b][1,3,4]thiadiazol-6-yl)benzo[d]thiazole

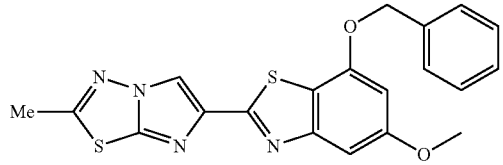 [SMILES: COc1cc(OCc2ccccc2)c2sc(-c3cn4nc(C)sc4n3)nc2c1]

A sealable vessel was charged with 5-methyl-1,3,4-thiadiazol-2-amine (0.121 g, 1.050 mmol), 1-(7-(benzyloxy)-5-methoxybenzo[d]thiazol-2-yl)-2-bromoethanone (0.412 g, 1.05 mmol) and isopropanol (5 mL). The reaction mixture was heated at 85° C. for 4 hours after which some of the bromoethanone remained. More 5-methyl-1,3,4-thiadiazol-2-amine (0.100 g, 0.868 mmol) was added and the mixture was again heated at 85° C. for 2 h. The reaction mixture was then transferred to a microwaveable vessel and heated at 155° C. for 45 min before being concentrated to near dryness. The reside was triturated with acetonitrile and the resulting suspension was filtered and the residue dried in vacuo to give 7-(benzyloxy)-5-methoxy-2-(2-methylimidazo[2,1-b][1,3,4]thiadiazol-6-yl)benzo[d]thiazole (0.218 g, 0.534 mmol, 50%) as a brown solid. LC (Method B): 2.306 min. HRMS (ESI): calcd for $C_{20}H_{17}N_4O_2S_2$ [M+H]$^+$ m/z, 409.0787, found 409.0956. $^1$HNMR (400 MHz, DMSO-$d_6$) δ ppm 8.82 (s, 1H), 7.50 (m, 2H), 7.42 (m, 2H), 7.35 (m, 1H), 7.15 (d, J=1.6 Hz, 1H), 6.75 (d, J=1.6 Hz, 1H), 5.33 (s, 2H), 3.84 (s, 3H), 2.77 (s, 3H).

Intermediate 1F. 5-Methoxy-2-(2-methylimidazo[2,1-b][1,3,4]thiadiazol-6-yl)benzo[d]thiazol-7-ol

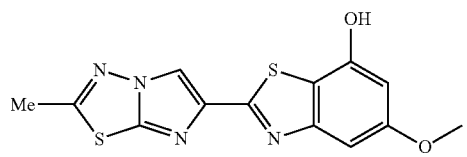 [SMILES: COc1cc(O)c2sc(-c3cn4nc(C)sc4n3)nc2c1]

A solution of 1,2,3,4,5-pentamethylbenzene (2.06 g, 13.9 mmol) in TFA (36 mL) was charged with a solution of 7-(benzyloxy)-5-methoxy-2-(2-methylimidazo[2,1-b][1,3,4]thiadiazol-6-yl)benzo[d]thiazole (1.62 g, 3.97 mmol) in TFA (10 mL). The reaction mixture was heated at 60° C. for 6 h, after which it was cooled to ambient temperature and concentrated to dryness. The residue was purified by ISCO using a RESDISEP® 40 g column (DCM/EtOAc) to give 5-methoxy-2-(2-methylimidazo[2,1-b][1,3,4]thiadiazol-6-yl)benzo[d]thiazol-7-ol (0.758 g, 2.379 mmol, 60%) as a beige solid:). LC (Method B): 1.875 min. HRMS (ESI): calcd for $C_{13}H_{11}N_4O_2S_2$ [M+H]$^+$ m/z, 319.0318, found 319.0337. $^1$HNMR (400 MHz, DMSO-$d_6$) δ ppm 10.57 (s, 1H), 8.79 (s, 1H), 7.03 (d, J=2.3 Hz, 1H), 6.47 (d, J=2.3 Hz, 1H), 3.80 (s, 3H), 2.76 (s, 3H).

Intermediate 1G. (2-Bromothiazol-4-yl)methanol

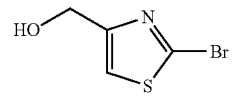

A solution of methyl 2-bromothiazole-4-carboxylate (500 mg, 2.25 mmol) in EtOH (10 mL) was cooled at 0° C. under nitrogen and NaBH$_4$ (170 mg, 4.50 mmol) was added portion-wise over 5 min. The mixture was stirred at the same temperature for 15 min and then it was heated at 90° C. for 1 h. The cooled mixture was quenched with saturated aqueous NH$_4$Cl (15 mL) and stirring was continued for 20 min. Ethyl acetate (50 mL) was then added and the organic phase was separated, washed with brine, dried over MgSO$_4$ and concentrated to dryness to give the title compound (0.212 g, 49%) which was used as such in the next step. $^1$HNMR (400 MHz, CDCl$_3$) δ ppm 7.18 (s, 1H), 4.76 (s, 2H), 2.21 (br s, 1H).

Intermediate 1H. 2-Bromo-4-(((tert-butyldimethylsilyl)oxy)methyl)thiazole

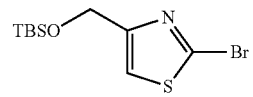 [SMILES: CC(C)(C)[Si](C)(C)OCc1csc(Br)n1]

To an ice-cold solution of (2-bromothiazol-4-yl)methanol (212 mg, 1.09 mmol) in DMF (10 mL) was added TBS-Cl (329 mg, 2.19 mmol), followed by imidazole (171 mg, 2.51 mmol). The mixture was allowed to warm to room temperature over 10 min and stirring was continued for 18 h. The reaction was quenched by the addition of EtOH at 0° C. and then the mixture was stirred at room temperature for 10 min before being partitioned with EtOAc-saturated aqueous NaHCO$_3$. The organic layer was separated, washed with brine, dried over MgSO$_4$ and concentrated to dryness. The residue was purified on the ISCO using a REDISEP® 12 g column (0-5% EtOAc-DCM) to give the title compound (333 mg, 99%) as a yellow oil. MS (APCI): calcd for $C_{10}H_{19}BrNOSSi$ [M+H]$^+$ m/z, 308.0, found 308.0. $^1$HNMR (400 MHz, CDCl$_3$) δ ppm 7.14 (t, J=1.5 Hz, 1H), 4.83 (d, J=1.6 Hz, 2H), 0.92 (s, 9H), 0.12 (s, 6H).

Intermediate 1I. tert-Butyl 4-(4-(((tert-butyldimethylsilyl)oxy)methyl)thiazol-2-yl)benzoate

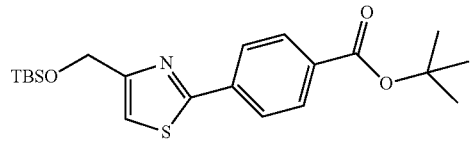 [SMILES: CC(C)(C)OC(=O)c1ccc(-c2nc(CO[Si](C)(C)C(C)(C)C)cs2)cc1]

A mixture of 2-bromo-4-(((tert-butyldimethylsilyl)oxy)methyl)thiazole (1.542 g, 5.000 mmol) and (4-(tert-butoxycarbonyl)phenyl)boronic acid (1.388 g, 6.25 mmol) in toluene:tert-butanol (3:1, 60 mL) was purged with a stream of nitrogen bubbles in a sealable flask for 15 min. To this mixture was added Pd(dppf)Cl₂·DCM (204 mg, 0.250 mmol) and 2 M Na₂CO₃ (3.13 mL, 6.25 mmol), the flask was sealed and the mixture was stirred at 95° C. (oil bath temperature) for 4 h. Another 0.25 equiv of the boronic acid and 2 M Na₂CO₃ was then added, together with an arbitrary but small amount of the catalyst. The mixture was stirred at 95° C. for another 2 h and then the cooled mixture was partitioned with EtOAc-water. The organic phase was separated, washed with brine, dried over Na₂SO₄ and evaporated to give a dark brown gum. Flash chromatography on the ISCO (0-10% EtOAc-hexane) afforded the title compound (1.065 g, 53%) as a colorless gum. LC (Method B): 3.407 min MS (APCI): calcd for $C_{21}H_{32}NO_3SSi$ [M+H]⁺ m/z, 406.19, found 406.2. ¹HNMR (400 MHz, CDCl₃) δ ppm 8.04 (d, J=8.6 Hz, 2H), 7.98 (d, J=8.6 Hz, 2H), 7.26 (s, 1H), 4.79 (s, 2H), 1.47 (s, 9H), 0.82 (s, 9H), 0.10 (s, 6H).

Intermediate 1J. tert-Butyl 4-(4-(hydroxymethyl)thiazol-2-yl)benzoate

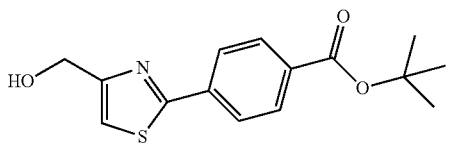 [SMILES: CC(C)(C)OC(=O)c1ccc(-c2nc(CO)cs2)cc1]

To a solution of tert-butyl 4-(4-(((tert-butyldimethylsilyl)oxy)methyl)thiazol-2-yl)benzoate (1.058 g, 2.61 mmol) in dry THF (25 mL) under nitrogen was added triethylamine trihydrofluoride (1.274 mL, 7.82 mmol) dropwise and the mixture was then stirred at room temperature for 18 h. The resulting mixture was partitioned with EtOAc-saturated aqueous NaHCO₃ and the organic phase was separated, dried (Na₂SO₄) and evaporated to give the title compound (760 mg, 100%) as a colorless gum which crystallized on standing in vacuo. This material was essentially pure and was used as such in the next step. LC (Method B): 2.239 min MS (APCI): calcd for $C_{15}H_{18}NO_3S$ [M+H]⁺ m/z, 292.10, found 292.2. ¹HNMR (400 MHz, CDCl₃) δ ppm 8.18-7.92 (m, 4H), 7.27 (s, 1H), 4.86 (d, J=5.9 Hz, 2H), 2.41-2.22 (m, 1H), 1.63 (s, 9H).

Example 1: tert-Butyl 4-(4-(((5-methoxy-2-(2-methylimidazo[2,1-b][1,3,4]thiadiazol-6-yl)benzo[d]thiazol-7-yl)oxy)methyl)thiazol-2-yl)benzoate

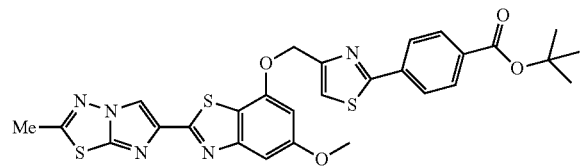 [SMILES: COc1cc(OCc2csc(-c3ccc(C(=O)OC(C)(C)C)cc3)n2)c2sc(-c3cn4nc(C)sc4n3)nc2c1]

To a flame-dried 100 ml round bottomed flask containing 5-methoxy-2-(2-methylimidazo[2,1-b][1,3,4]thiadiazol-6-yl)benzo[d]thiazol-7-ol (Intermediate 1F, 229 mg, 0.719 mmol) and tert-butyl 4-(4-(hydroxymethyl)thiazol-2-yl)benzoate (Intermediate 1J, 210 mg, 0.719 mmol) in dry THF (10 mL) was added tributylphosphine (0.467 mL, 1.798 mmol). The resulting solution was charged with a solution of ADDP (454 mg, 1.798 mmol) in THF (10 mL), added dropwise over 20 min. After stirring for 30 min, the reaction mixture was partitioned between ethyl acetate-saturated aqueous NaHCO₃. The organic phase was separated, washed with brine, dried (MgSO₄), filtered and concentrated to dryness. The residue was purified by ISCO using a REDISEP® 80 g column (DCM/EtOAc). Fractions containing the desired product were concentrated to give a beige solid: tert-butyl 4-(4-(((5-methoxy-2-(2-methylimidazo[2,1-b][1,3,4]thiadiazol-6-yl)benzo[d]thiazol-7-yl)oxy)methyl)thiazol-2-yl)benzoate (373 mg, 0.630 mmol, 88%). LC (Method B): 2.614 min. HRMS (ESI) calcd for $C_{28}H_{26}N_5O_4S_3$ [M+H]⁺ m/z, 592.1141, found 592.1152. ¹HNMR in DMSO-d₆: δ ppm 8.82 (s, 1H), 8.09 (m, 2H), 8.02 (m, 2H), 7.96 (s, 1H), 7.18 (d, J=2.0 Hz, 1H), 6.90 (d, J=2.0 Hz, 1H), 5.49 (s, 2H), 3.86 (s, 3H), 2.76 (s, 3H), 1.57 (s, 9H).

Scheme 4

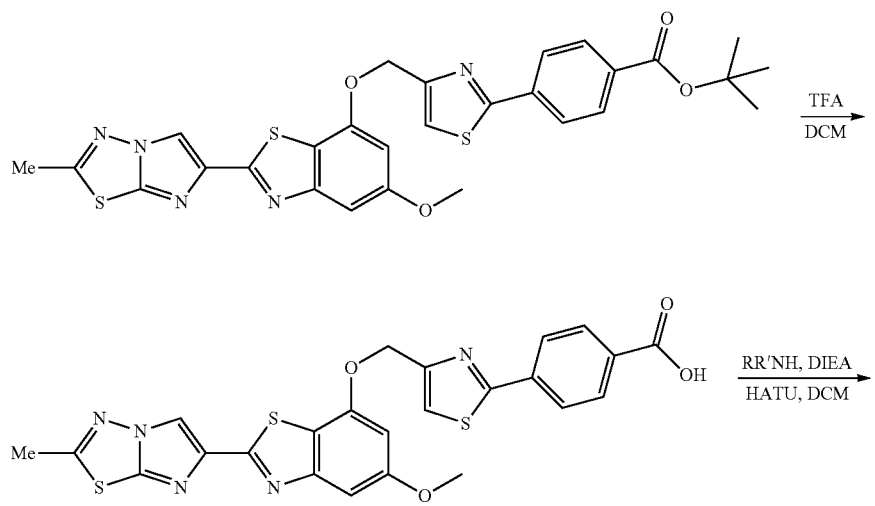

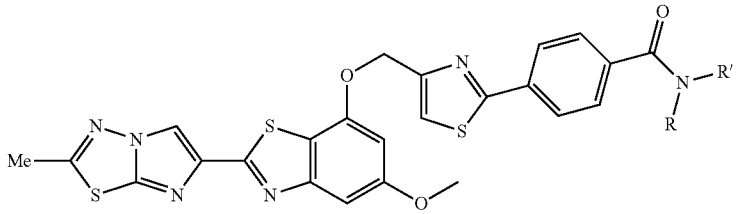

Example 2: 4-(4-(((5-Methoxy-2-(2-methylimidazo[2,1-b][1,3,4]thiadiazol-6-yl)benzo[d]thiazol-7-yl)oxy)methyl)thiazol-2-yl)benzoic acid

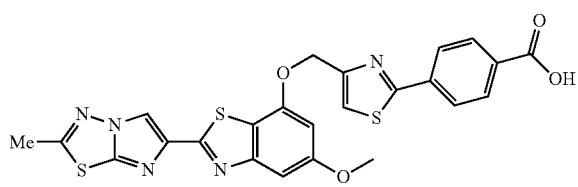 [SMILES: COc1cc(OCc2csc(-c3ccc(C(=O)O)cc3)n2)c2sc(-c3cn4nc(C)sc4n3)nc2c1]

To a stirred solution of tert-butyl 4-(4-(((5-methoxy-2-(2-methylimidazo[2,1-b][1,3,4]thiadiazol-6-yl)benzo[d]thiazol-7-yl)oxy)methyl)thiazol-2-yl)benzoate (Example 1, 160 mg, 0.270 mmol) in DCM (5 mL) was added TFA (1 mL). The reaction mixture was stirred at ambient temperature for 6 h and then it was concentrated to dryness to give 4-(4-(((5-methoxy-2-(2-methylimidazo[2,1-b][1,3,4]thiadiazol-6-yl)benzo[d]thiazol-7-yl)oxy)methyl)thiazol-2-yl)benzoic acid (145 mg, 0.270 mmol, 100%) as a solid. This material was used as such in the next step. LC (Method B): 2.268 min HRMS (ESI): calcd for $C_{24}H_{18}N_5O_4S_3$ [M+H]$^+$ m/z 536.0515, found 536.0556. $^1$HNMR (400 MHz, DMSO-$d_6$) δ ppm 8.80 (s, 1H), 8.07 (m, 4H), 7.95 (s, 1H), 7.17 (d, J=2.0 Hz, 1H), 6.89 (d, J=2.0 Hz, 1H), 5.47 (s, 2H), 3.86 (s, 3H), 2.75 (s, 3H).

Example 3: (S)-4-(4-(((5-methoxy-2-(2-methylimidazo[2,1-b][1,3,4]thiadiazol-6-yl)benzo[d]thiazol-7-yl)oxy)methyl)thiazol-2-yl)-N-methyl-N-(tetrahydrofuran-3-yl)benzamide General Method:

To a stirred solution of 4-(4-(((5-methoxy-2-(2-methylimidazo[2,1-b][1,3,4]thiadiazol-6-yl)benzo[d]thiazol-7-yl)oxy)methyl)thiazol-2-yl)benzoic acid (Example 2, 27 mg, 0.050 mmol) and (S)—N-methyltetrahydrofuran-3-amine hydrochloride (6.9 mg, 0.050 mmol) in DMF (1 mL) was added DIEA (0.035 ml, 0.20 mmol) and then HATU (19 mg, 0.050 mmol). The reaction mixture was stirred at room temperature for 16 h and then it was submitted directly to prep HPLC in TFA buffered methanol-water. Fractions containing the desired product were concentrated to give (S)-4-(4-(((5-methoxy-2-(2-methylimidazo[2,1-b][1,3,4]thiadiazol-6-yl)benzo[d]thiazol-7-yl)oxy)methyl)thiazol-2-yl)-N-methyl-N-(tetrahydrofuran-3-yl)benzamide (16 mg, 0.026 mmol, 52%) as a yellow solid. LC (Method B): 2.272 min. HRMS (ESI): calcd for $C_{29}H_{27}N_6O_4S_3$ [M+H]$^+$ m/z 619.1250, found 619.1280. $^1$HNMR (400 MHz, DMSO-$d_6$) δ ppm 8.82 (s, 1H), 8.02 (m, 2H), 7.91 (s, 1H), 7.52 (m, 2H), 7.18 (d, J=1.6 Hz, 1H), 6.90 (d, J=2.0 Hz, 1H), 5.47 (s, 2H), 3.94 (m, 2H), 3.86 (s, 3H), 3.80 (m, 2H), 2.88 (br s, 3H), 2.76 (s, 3H), 2.14 (br s, 1.5H), 1.96 (m, 1.5H).

Examples 4-11 were prepared according to the general method described in Example 3 above;

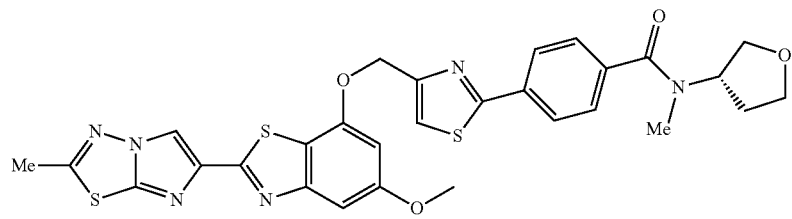 [SMILES: COc1cc(OCc2csc(-c3ccc(C(=O)N(C)[C@H]4CCOC4)cc3)n2)c2sc(-c3cn4nc(C)sc4n3)nc2c1]

Example 4: (S)-(3-Hydroxypiperidin-1-yl)(4-(4-(4-(((5-methoxy-2-(2-methylimidazo[2,1-b][1,3,4]thiadiazol-6-yl)benzo[d]thiazol-7-yl)oxy)methyl)thiazol-2-yl)phenyl)methanone

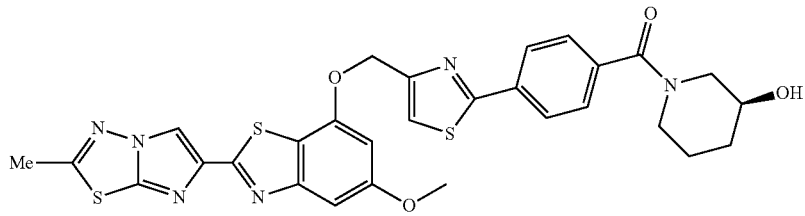 [SMILES: COc1cc(OCc2csc(-c3ccc(C(=O)N4CCC[C@H](O)C4)cc3)n2)c2sc(-c3cn4nc(C)sc4n3)nc2c1]

LC (Method B): 2.220 min. HRMS (ESI): calcd for C$_{29}$H$_{27}$N$_6$O$_4$S$_3$ [M+H]$^+$ m/z 619.1250, found 619.1278. $^1$HNMR (400 MHz, DMSO-d$_6$) δ ppm 8.80 (s, 1H), 7.99 (m, 2H), 7.89 (s, 1H), 7.50 (m, 2H), 7.16 (d, J=1.6 Hz, 1H), 6.88 (d, J=2.0 Hz, 1H), 5.45 (s, 2H), 4.16 (m, 1H), 3.84 (s, 3H), 3.45 (m, 2H), 3.30 (m, 1H), 3.00 (m, 1H), 2.84 (m, 1H), 2.74 (s, 3H), 1.85-1.61 (m, 2H), 1.40 (m, 2H).

Example 5: N—(Cyanomethyl)-4-(4-(((5-methoxy-2-(2-methylimidazo[2,1-b][1,3,4]thiadiazol-6-yl)benzo[d]thiazol-7-yl)oxy)methyl)thiazol-2-yl)-N-methylbenzamide

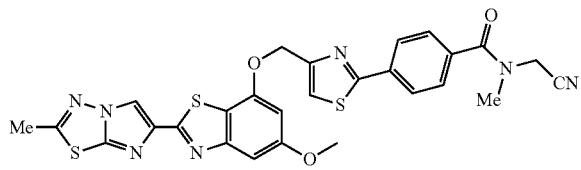 [SMILES: COc1cc(OCc2csc(-c3ccc(C(=O)N(C)CC#N)cc3)n2)c2sc(-c3cn4nc(C)sc4n3)nc2c1]

LC (Method B): 2.196 min. HRMS (ESI): calcd for C$_{27}$H$_{22}$N$_7$O$_3$S$_3$ [M+H]$^+$ m/z 588.0941, found 588.0954. $^1$HNMR (400 MHz, DMSO-d$_6$) δ ppm 8.82 (s, 1H), 8.06 (m, 2H), 7.93 (s, 1H), 7.62 (d, J=7.8 Hz, 2H), 7.18 (d, J=2.0 Hz, 1H), 6.90 (d, J=2.0 Hz, 1H), 5.48 (s, 2H), 4.55 (br s, 2H), 3.86 (s, 3H), 3.05 (s, 3H), 2.76 (s, 3H).

Example 6: 4-(4-(((5-Methoxy-2-(2-methylimidazo[2,1-b][1,3,4]thiadiazol-6-yl)benzo[d]thiazol-7-yl)oxy)methyl)thiazol-2-yl)-N,N-dimethylbenzamide

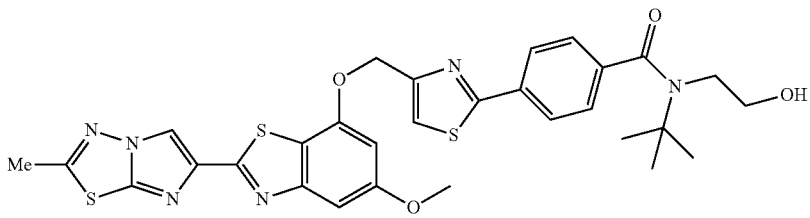 [SMILES: COc1cc(OCc2csc(-c3ccc(C(=O)N(CCO)C(C)(C)C)cc3)n2)c2sc(-c3cn4nc(C)sc4n3)nc2c1]

LC (Method B): 2.227 min. HRMS (ESI): calcd for C$_{26}$H$_{23}$N$_6$O$_3$S$_3$ [M+H]$^+$ m/z 563.0988, found 563.0995. $^1$HNMR (400 MHz, DMSO-d$_6$) δ ppm 8.82 (s, 1H), 8.01 (m, 2H), 7.91 (s, 1H), 7.54 (m, 2H), 7.18 (d, J=2.0 Hz, 1H), 6.91 (d, J=2.0 Hz, 1H), 5.47 (s, 2H), 3.86 (s, 3H), 3.00 (br s, 3H), 2.93 (br s, 3H), 2.76 (s, 3H).

Example 7: N-(tert-Butyl)-N-(2-hydroxyethyl)-4-(4-(4-(((5-methoxy-2-(2-methylimidazo[2,1-b][1,3,4]thiadiazol-6-yl)benzo[d]thiazol-7-yl)oxy)methyl)thiazol-2-yl)benzamide LC (Method B): 2.144 min. HRMS (ESI): calcd for C$_{30}$H$_{31}$N$_6$O$_4$S$_3$ [M+H]$^+$ m/z 635.1563, found 635.1566 $^1$HNMR (400 MHz, DMSO-d$_6$) δ ppm 8.83 (s, 1H), 8.54 (br s, 1.5H), 8.17 (s, 4.5H), 8.00 (s, 1H), 7.19 (d, J=2.0 Hz, 1H), 6.91 (d, J=2.0 Hz, 1H), 5.49 (s, 2H), 4.52 (t, J=5.1 Hz, 2H), 3.86 (s, 3H), 2.77 (s, 3H), 1.32 (s, 9H).

Example 8: (R)-(3-(hydroxymethyl)pyrrolidin-1-yl) (4-(4-(4-(((5-methoxy-2-(2-methylimidazo[2,1-b][1,3,4]thiadiazol-6-yl)benzo[d]thiazol-7-yl)oxy)methyl)thiazol-2-yl)phenyl)methanone

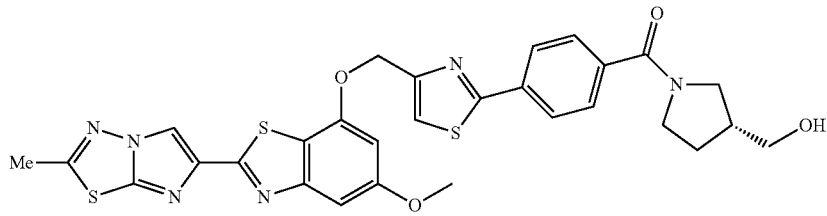 [SMILES: COc1cc(OCc2csc(-c3ccc(C(=O)N4CC[C@@H](CO)C4)cc3)n2)c2sc(-c3cn4nc(C)sc4n3)nc2c1]

LC (Method B): 2.188 min. HRMS (ESI): calcd for $C_{29}H_{27}N_6O_4S_3$ [M+H]$^+$ m/z 619.1256, found 619.1261. $^1$HNMR (400 MHz, DMSO-d$_6$) δ ppm 8.82 (s, 1H), 8.01 (dd, J=3.9, 8.2 Hz, 2H), 7.91 (s, 1H), 7.64 (d, J=8.2 Hz, 2H), 7.18 (d, J=2.0 Hz, 1H), 6.91 (d, J=2.3 Hz, 1H), 5.47 (s, 2H), 3.86 (s, 3H), 3.58 (m, 2H), 3.51-3.36 (m, 2H), 3.30-3.21 (m, 2H), 2.76 (s, 3H), 2.33 (m, 1H), 1.92 (m, 1H), 1.64 (m, 1H), 1.27-1.22 (m, 1H).

Example 9: (R)-(3-(Hydroxymethyl)morpholino)(4-(4-(((5-methoxy-2-(2-methylimidazo[2,1-b][1,3,4]thiadiazol-6-yl)benzo[d]thiazol-7-yl)oxy)methyl)thiazol-2-yl)phenyl)methanone

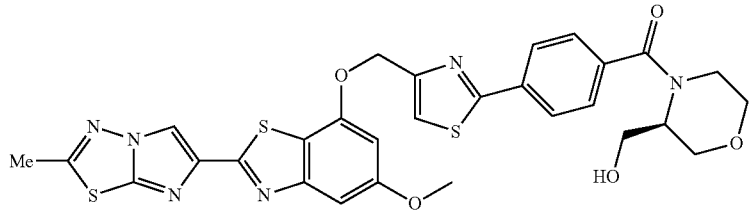 [SMILES: COc1cc(OCc2csc(-c3ccc(C(=O)N4CCOC[C@H]4CO)cc3)n2)c2sc(-c3cn4nc(C)sc4n3)nc2c1]

LC (Method B): 2.151 min. HRMS (ESI): calcd for $C_{29}H_{27}N_6O_5S_3$ [M+H]$^+$ m/z 635.1200, found 635.1196 $^1$HNMR (400 MHz, DMSO-d$_6$) δ ppm 8.82 (s, 1H), 8.01 (d, J=8.2 Hz, 2H), 7.91 (s, 1H), 7.55 (d, J=8.2 Hz, 2H), 7.18 (d, J=2.0 Hz, 1H), 6.90 (d, J=2.3 Hz, 1H), 5.47 (s, 2H), 4.33 (m, 1H), 3.65-3.03 (m, 9H), 2.76 (s, 3H).

Example 10: 4-(4-(((5-Methoxy-2-(2-methylimidazo[2,1-b][1,3,4]thiadiazol-6-yl)benzo[d]thiazol-7-yl)oxy)methyl)thiazol-2-yl)-N-methyl-N-(tetrahydro-2H-pyran-4-yl)benzamide LC (Method B): 2.289 min. HRMS (ESI): calcd for $C_{30}H_{29}N_6O_4S_3$ [M+H]$^+$ m/z 633.1407, found 633.1430 $^1$HNMR (400 MHz, DMSO-d$_6$) δ 8.82 (s, 1H), 8.02 (m, 2H), 7.91 (s, 1H), 7.51 (d, J=7.8 Hz, 2H), 7.18 (d, J=1.6 Hz, 1H), 6.90 (d, J=2.0 Hz, 1H), 5.47 (s, 2H), 4.54 (br s, 1H), 3.93 (br s, 1H), 3.86 (s, 3H), 3.59 (m, 2H), 3.11 (m, 2H), 2.83 (m, 3H), 2.76 (s, 3H), 1.82 (m, 2H), 1.58 (m, 2H).

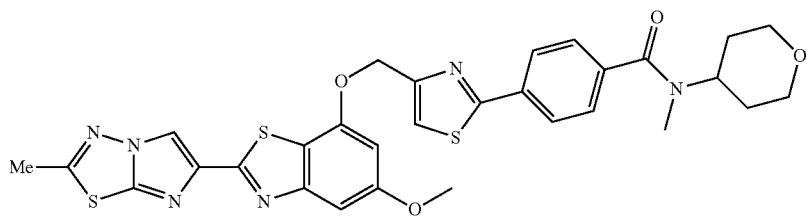 [SMILES: COc1cc(OCc2csc(-c3ccc(C(=O)N(C)C4CCOCC4)cc3)n2)c2sc(-c3cn4nc(C)sc4n3)nc2c1]

Example 11: (S)-(3-(Hydroxymethyl)morpholino) (4-(4-(((5-methoxy-2-(2-methylimidazo[2,1-b][1,3, 4]thiadiazol-6-yl)benzo[d]thiazol-7-yl)oxy)methyl) thiazol-2-yl)phenyl)methanone
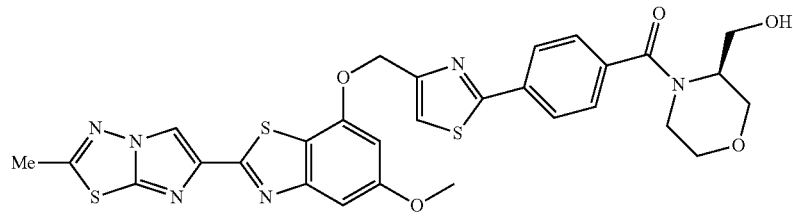 [SMILES: COc1cc(OCc2csc(-c3ccc(C(=O)N4CCOC[C@@H]4CO)cc3)n2)c2sc(-c3cn4nc(C)sc4n3)nc2c1]
LC (Method B): 2.141 min. HRMS (ESI): calcd for $C_{29}H_{27}N_6O_5S_3$ [M+H]$^+$ m/z 635.1200, found 635.1219. $^1$HNMR (400 MHz, DMSO-d$_6$) δ 8.80 (s, 1H), 7.99 (d, J=8.2 Hz, 2H), 7.91 (s, 1H), 7.55 (d, J=8.2 Hz, 2H), 7.18 (d, J=1.6 Hz, 1H), 6.90 (d, J=2.0 Hz, 1H), 5.47 (s, 2H), 4.33 (m, 1H), 4.04 (m, 2H), 3.86 (s, 3H), 3.78-3.55 (m, 7H), 2.76 (s, 3H).
Scheme 5
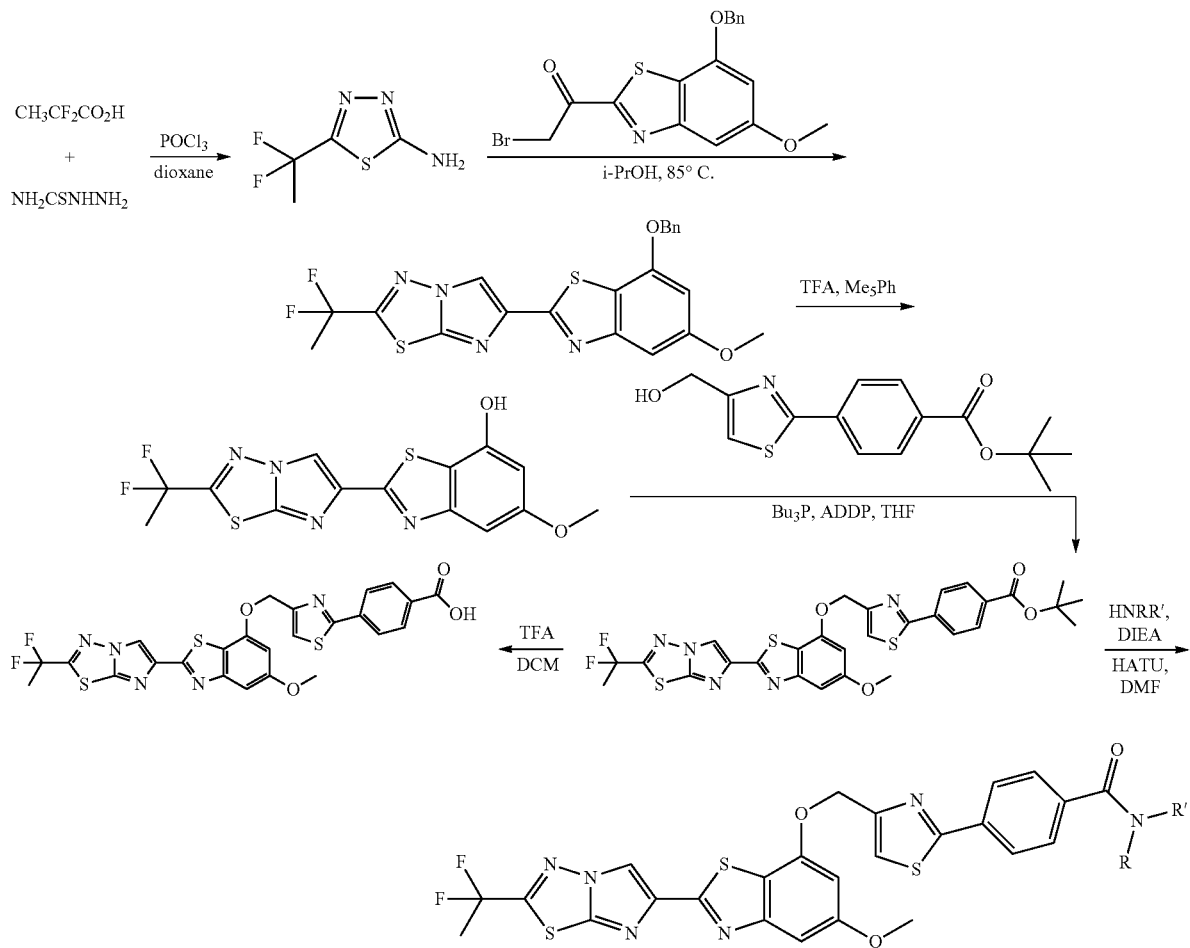

Example 12

7-(Benzyloxy)-2-(2-(1,1-difluoroethyl)imidazo[2,1-b][1,3,4]thiadiazol-6-yl)-5-methoxybenzo[d]thiazole

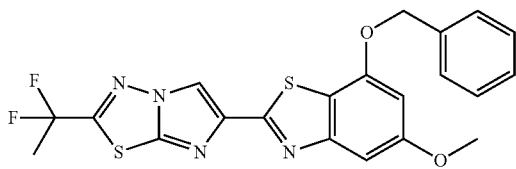 [SMILES: COc1cc(OCc2ccccc2)c2sc(-c3cn4nc(C(C)(F)F)sc4n3)nc2c1]

Intermediate 12A.
5-(1,1-Difluoroethyl)-1,3,4-thiadiazol-2-amine

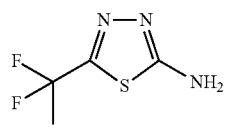

To an ice-cold suspension of thiosemicarbazide (4.97 g, 54.5 mmol) in dioxane (45 mL) was slowly added a solution of 2,2-difluoropropionic acid (4.50 g, 40.9 mmol) in dioxane (5 mL). To the resulting thick off-white slurry was added POCl$_3$ (4.99 mL, 54.5 mmol) dropwise, then the cooling bath was removed and the mixture was stirred at room temperature for 1 h. The vessel was then sealed and the mixture was heated at 90-95° C. (oil bath temperature) for 5 h. The cooled mixture was concentrated under reduced pressure and the concentrate was poured into ice water (150 mL). The mixture was basified to ca.pH 9 using 40% aqueous NaOH and the resulting slurry was filtered. The filter-cake was washed with water, ether and hexanes, and then it was dried in vacuo overnight to give the title compound (4.31 g, 64%) as a white solid. It was used as such in the next step. LC (Method A: Eclipse XDB-C18, 3.5 microns, 4.6×30 mm; 2 min gradient, MeCN—H$_2$O-TFA=5:95:0.5 to 95:5:0.5; 4 min run): 0.891 min. MS (APCI): calcd for C$_4$H$_6$F$_2$N$_3$S [M+H]$^+$ m/z 165.02, found 166.0. $^1$H NMR (600 MHz, DMSO-d$_6$) δ ppm 7.69 (s, 2H), 2.06 (t, J=19.0 Hz, 3H).

Example 12: 7-(Benzyloxy)-2-(2-(1,1-difluoroethyl)imidazo[2,1-b][1,3,4]thiadiazol-6-yl)-5-methoxybenzo[d]thiazole

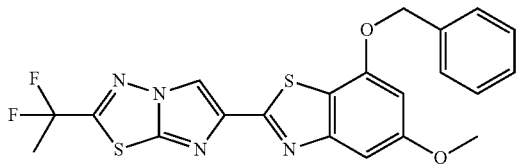 [SMILES: COc1cc(OCc2ccccc2)c2sc(-c3cn4nc(C(C)(F)F)sc4n3)nc2c1]

A sealable vessel was charged with 5-(1,1-difluoroethyl)-1,3,4-thiadiazol-2-amine (0.897 g, 5.43 mmol), 1-(7-(benzyloxy)-5-methoxybenzo[d]thiazol-2-yl)-2-bromoethanone (Intermediate 1D, 1.42 g, 3.62 mmol) and i-PrOH (35 mL). The reaction mixture was heated at 85° C. for 16 h and then the cooled mixture was concentrated to near dryness. The concentrate was partitioned with EtOAc-saturated aqueous NaHCO$_3$ and the organic phase was separated, dried (MgSO$_4$), filtered and concentrated. The residue was purified by ISCO using a REDISEP® 80 g column (DCM/EtOAc) to give 7-(benzyloxy)-2-(2-(1,1-difluoroethyl)imidazo[2,1-b][1,3,4]thiadiazol-6-yl)-5-methoxybenzo[d]thiazole (0.547 g, 1.193 mmol, 33%) as an orange solid. LC (Method B): 2.499 min. HRMS (ESI): calcd for C$_{21}$H$_{17}$F$_2$N$_4$O$_2$S$_2$ [M+H]$^+$ m/z 459.0756, found 459.0764. $^1$HNMR (400 MHz, DMSO-d) δ ppm 9.07 (s, 1H), 7.50 (m, 2H), 7.43 (m, 2H), 7.35 (m, 1H), 7.19 (d, J=2.0 Hz, 1H), 6.78 (d, J=2.0 Hz, 1H), 5.35 (s, 2H), 3.84 (s, 3H), 2.24 (t, J=19.4 Hz, 3H).

Example 13 tert-Butyl 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)benzoate

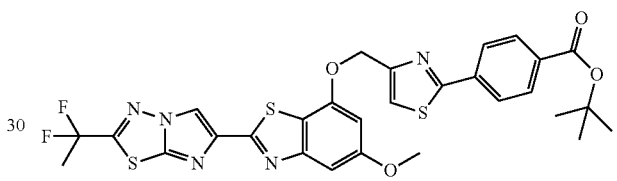

Intermediate 13A. 2-(2-(1,1-Difluoroethyl)imidazo[2,1-b][1,3,4]thiadiazol-6-yl)-5-methoxybenzo[d]thiazol-7-ol

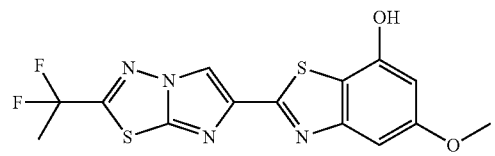 [SMILES: COc1cc(O)c2sc(-c3cn4nc(C(C)(F)F)sc4n3)nc2c1]

To a solution of 1,2,3,4,5-pentamethylbenzene (584 mg, 3.94 mmol) in TFA (12 mL) was added a solution of 7-(benzyloxy)-2-(2-(1,1-difluoroethyl)imidazo[2,1-b][1,3,4]thiadiazol-6-yl)-5-methoxybenzo[d]thiazole (Example 12, 516 mg, 1.13 mmol) in TFA (2.5 mL). The reaction mixture was heated at 60° C. for 6 h, after which it was cooled to room temperature and concentrated to dryness. The residue was purified by ISCO using a REDISEP® 80 g column (DCM/MeOH/AcOH) to give the impure product as a brown solid. Repurification by ISCO using a REDISEP® 80 g column (DCM/EtOAc) afforded pure 2-(2-(1,1-difluoroethyl)imidazo[2,1-b][1,3,4]thiadiazol-6-yl)-5-methoxybenzo[d]thiazol-7-ol (274 mg, 0.744 mmol, 66%) as a beige solid. LC (Method B): 2.100 min. HRMS (ESI): calcd for C$_{14}$H$_{11}$F$_2$N$_4$O$_2$S$_2$ [M+H]$^+$ m/z 369.0286, found 369.0304. $^1$HNMR (400 MHz, DMSO-d$_6$) δ ppm 10.62 (s, 1H), 9.05 (s, 1H), 7.06 (d, J=2.3 Hz, 1H), 6.49 (d, J=2.3 Hz, 1H), 3.80 (s, 3H), 2.24 (t, J=19.4 Hz, 3H).

Example 13: tert-Butyl 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)benzoate

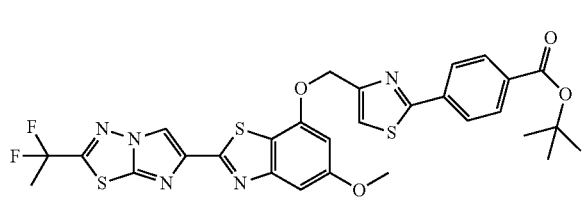 [SMILES: COc1cc(OCc2csc(-c3ccc(C(=O)OC(C)(C)C)cc3)n2)c2sc(-c3cn4nc(C(C)(F)F)sc4n3)nc2c1]

To a mixture of 2-(2-(1,1-difluoroethyl)imidazo[2,1-b][1,3,4]thiadiazol-6-yl)-5-methoxybenzo[d]thiazol-7-ol (274 mg, 0.744 mmol) and tert-butyl 4-(4-(hydroxymethyl)thiazol-2-yl)benzoate (Intermediate 1J, 217 mg, 0.744 mmol) in anhydrous THF (15 mL) was added tributylphosphine (0.483 mL, 1.86 mmol). To the resulting solution was added a solution of ADDP (469 mg, 1.86 mmol) in THF (10 mL) dropwise over 20 min. After stirring for another 30 min the reaction mixture was partitioned between EtOAc-saturated aqueous NaHCO$_3$. The organic phase was separated, washed with brine, dried (MgSO$_4$), filtered and concentrated to dryness. The residue was triturated with acetonitrile and the solid was filtered and then dried in vacuo to give tert-butyl 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)benzoate (394 mg, 0.614 mmol, 83%) as a beige solid. LC (Method B): 2.700 min HRMS (ESI): calcd for C$_{29}$H$_{26}$F$_2$N$_5$O$_4$S$_3$ [M+11]$^+$ m/z 642.1109, found 642.1131. $^1$HNMR (400 MHz, DMSO-d$_6$) δ ppm 9.07 (s, 1H), 8.09 (m, 2H), 8.02 (m, 2H), 7.96 (s, 1H), 7.22 (d, J=2.0 Hz, 1H), 6.93 (d, J=2.0 Hz, 1H), 5.50 (s, 2H), 3.87 (s, 3H), 2.24 (t, J=19.4 Hz, 3H), 1.57 (s, 9H).

Example 14: 4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)benzoic acid

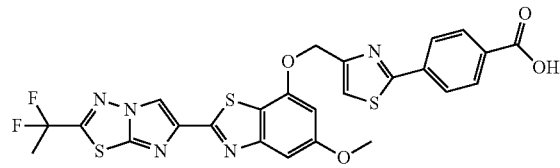 [SMILES: COc1cc(OCc2csc(-c3ccc(C(=O)O)cc3)n2)c2sc(-c3cn4nc(C(C)(F)F)sc4n3)nc2c1]

To a stirred solution of tert-butyl 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)benzoate (375 mg, 0.584 mmol) in DCM (10 mL) was added TFA (1 mL). The reaction mixture was stirred at room temperature for 16 h and then it was concentrated to dryness to give the title compound as a yellow solid. LC (Method B): 2.408 min HRMS (ESI): calcd for C$_{25}$H$_{18}$F$_2$N$_5$O$_4$S$_3$ [M+H]$^+$ m/z 586.0411, found 586.0496. $^1$HNMR (400 MHz, DMSO-d$_6$) δ ppm 9.07 (s, 1H), 8.07 (m, 4H), 7.96 (s, 1H), 7.22 (d, J=2.0 Hz, 1H), 6.94 (d, J=2.0 Hz, 1H), 5.50 (s, 2H), 3.87 (s, 3H), 2.24 (t, J=19.4 Hz, 3H).

Examples 15-22 were prepared from 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)benzoic acid according to the general method described for Example 3;

Example 15: (S)-4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)-N-methyl-N-(tetrahydrofuran-3-yl)benzamide

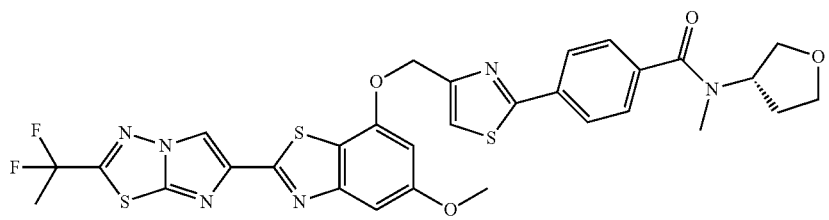 [SMILES: COc1cc(OCc2csc(-c3ccc(C(=O)N(C)[C@H]4CCOC4)cc3)n2)c2sc(-c3cn4nc(C(C)(F)F)sc4n3)nc2c1]

LC (Method B): 2.382 min. HRMS (ESI): calcd for $C_{30}H_{27}F_2N_6O_4S_3$ [M+H]+ m/z 669.1218, found 669.1225. 1HNMR (400 MHz, DMSO-d6) δ ppm 9.07 (s, 1H), 8.02 (d, J=8.2 Hz, 2H), 7.91 (s, 1H), 7.52 (br m, 2H), 7.21 (d, J=2.0 Hz, 1H), 6.93 (d, J=2.0 Hz, 1H), 5.48 (s, 2H), 4.32 (m, 1H), 3.94 (m, 1H), 3.87 (s, 3H), 3.79 (m, 1H), 3.58 (m, 2H), 2.87 (s, 3H), 2.24 (t, J=19.4 Hz, 3H), 2.11 (m, 1H), 1.96 (m, 1H).

Example 16: (S)-(4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)phenyl)(3-hydroxypiperidin-1-yl)methanone

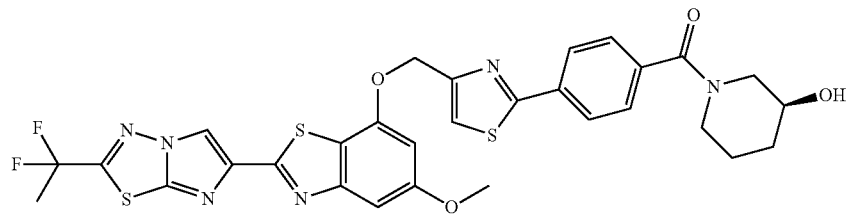 [SMILES: COc1cc(OCc2csc(-c3ccc(C(=O)N4CCC[C@H](O)C4)cc3)n2)c2sc(-c3cn4nc(C(C)(F)F)sc4n3)nc2c1]

LC (Method B): 2.317 min. HRMS (ESI): calcd for $C_{30}H_{27}F_2N_6O_4S_3$ [M+H]+ m/z 669.1218, found 669.1219. 1HNMR (400 MHz, DMSO-d6) δ ppm 9.07 (s, 1H), 8.01 (dd, J=2.0, 8.6 Hz, 2H), 7.91 (s, 1H), 7.52 (br m, 2H), 7.22 (d, J=2.0 Hz, 1H), 6.93 (d, J=2.0 Hz, 1H), 5.48 (s, 2H), 4.22-3.92 (m, 2H), 3.87 (s, 3H), 3.39-3.24 (m, 2H), 3.03 (m, 1H), 2.87 (m, 1H), 2.24 (t, J=19.4 Hz, 3H), 1.90-1.59 (m, 2H), 1.42 (m, 2H).

Example 17: N—(Cyanomethyl)-4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)-N-methylbenzamide

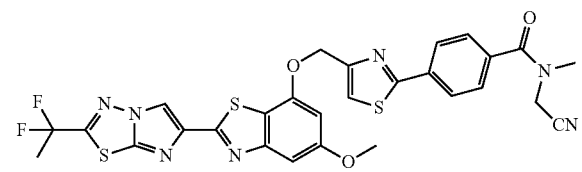 [SMILES: COc1cc(OCc2csc(-c3ccc(C(=O)N(C)CC#N)cc3)n2)c2sc(-c3cn4nc(C(C)(F)F)sc4n3)nc2c1]

LC (Method B): 2.282 min. HRMS (ESI): calcd for $C_{28}H_{22}F_2NH_7O_3S_3$ [M+H]+ m/z 638.0909, found 638.0912. 1HNMR (400 MHz, DMSO-d6) δ ppm 9.07 (s, 1H), 8.06 (d, J=8.2 Hz, 2H), 7.94 (s, 1H), 7.62 (d, J=8.2 Hz, 2H), 7.22 (d, J=2.0 Hz, 1H), 6.94 (d, J=2.0 Hz, 1H), 5.49 (s, 2H), 4.55 (s, 2H), 3.87 (s, 3H), 3.05 (s, 3H), 2.24 (t, J=19.4 Hz, 3H).

Example 18: 4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)-N,N-dimethylbenzamide

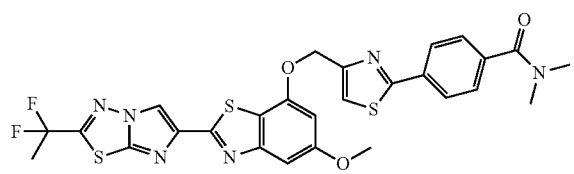 [SMILES: COc1cc(OCc2csc(-c3ccc(C(=O)N(C)C)cc3)n2)c2sc(-c3cn4nc(C(C)(F)F)sc4n3)nc2c1]

LC (Method B): 2.319 min. HRMS (ESI): calcd for $C_{27}H_{23}F_2N_6O_3S_3$ [M+H]+ m/z 613.0956, found 613.0961. 1HNMR (400 MHz, DMSO-d6) δ ppm 9.07 (s, 1H), 8.01 (m, 2H), 7.91 (s, 1H), 7.54 (m, 2H), 7.22 (d, J=2.0 Hz, 1H), 6.93 (d, J=2.0 Hz, 1H), 5.48 (s, 2H), 3.87 (s, 3H), 3.00 (br s, 3H), 2.94 (br s, 3H), 2.24 (t, J=19.4 Hz, 3H).

Example 19: N-(tert-Butyl)-4-(4-(((2-(2-(1,1-difluoroethyl)imidazo[2,1-b][1,3,4]thiadiazol-6-yl)-5-methoxybenzo[d]thiazol-7-yl)oxy)methyl)thiazol-2-yl)-N-(2-hydroxyethyl)benzamide

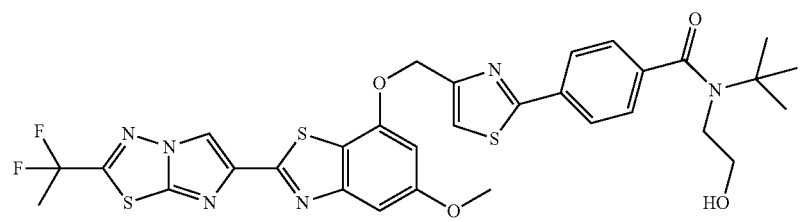 [SMILES: COc1cc(OCc2csc(-c3ccc(C(=O)N(CCO)C(C)(C)C)cc3)n2)c2sc(-c3cn4nc(C(C)(F)F)sc4n3)nc2c1]

LC (Method B): 2.223 min. HRMS (ESI): calcd for C$_{31}$H$_{31}$F$_2$N$_6$O$_4$S$_3$ [M+H]$^+$ m/z 685.1531, found 685.1557. $^1$HNMR (400 MHz, DMSO-d$_6$) δ ppm 9.06 (s, 1H), 8.53 (br s, 1H), 8.15 (s, 4H), 7.99 (s, 1H), 7.20 (d, J=2.0 Hz, 1H), 6.92 (d, J=2.0 Hz, 1H), 5.48 (s, 2H), 4.51 (t, J=5.1 Hz, 2H), 3.85 (s, 3H), 3.37 (br s, 2H), 2.23 (t, J=19.4 Hz, 3H), 1.30 (s, 9H).

Example 20: (R)-(4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)phenyl)(3-(hydroxymethyl)pyrrolidin-1-yl)methanone

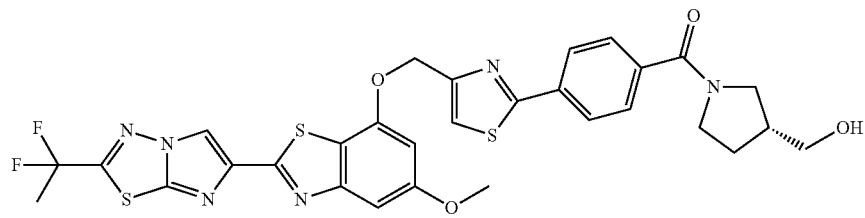 [SMILES: COc1cc(OCc2csc(-c3ccc(C(=O)N4CC[C@@H](CO)C4)cc3)n2)c2sc(-c3cn4nc(C(C)(F)F)sc4n3)nc2c1]

LC (Method B): 2.246 min. HRMS (ESI): calcd for C$_{30}$H$_{27}$F$_2$N$_6$O$_4$S$_3$ [M+H]$^+$ m/z 669.1224, found 669.1215. $^1$HNMR (400 MHz, DMSO-d$_6$) δ ppm 9.07 (s, 1H), 8.01 (dd, J=3.9, 8.6 Hz, 2H), 7.92 (s, 1H), 7.64 (d, J=8.2 Hz, 2H), 7.21 (d, J=2.0 Hz, 1H), 6.93 (d, J=2.3 Hz, 1H), 5.48 (s, 2H), 3.89 (s, 3H), 3.49-3.36 (m, 5H), 3.30-3.21 (m, 2H), 2.33 (m, 1H), 2.24 (t, J=19.4 Hz, 3H), 1.93 (m, 1H), 1.65 (m, 1H).

Example 21: (R)-(4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)phenyl)(3-(hydroxymethyl)morpholino)methanone

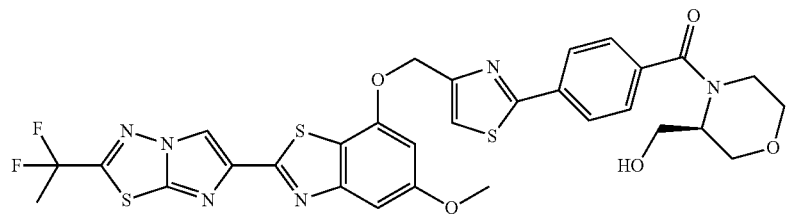 [SMILES: COc1cc(OCc2csc(-c3ccc(C(=O)N4CCOC[C@H]4CO)cc3)n2)c2sc(-c3cn4nc(C(C)(F)F)sc4n3)nc2c1]

LC (Method B): 2.291 min. HRMS (ESI): calcd for C$_{30}$H$_{27}$F$_2$N$_6$O$_5$S$_3$ [M+H]$^+$ m/z 685.1168, found 685.1167. $^1$HNMR (400 MHz, DMSO-d$_6$) δ ppm 9.07 (s, 1H), 8.01 (d, J=8.2 Hz, 2H), 7.91 (s, 1H), 7.55 (d, J=8.2 Hz, 2H), 7.22 (d, J=2.0 Hz, 1H), 6.93 (d, J=2.0 Hz, 1H), 5.48 (s, 2H), 4.42-3.91 (m, 2H), 3.87 (s, 3H), 3.79-3.57 (m, 6H), 3.12 (m, 1H), 2.24 (t, J=19.4 Hz, 3H).

Example 22: 4-(4-(((2-(2-(1,1-Difluoroethyl)imidazo[2,1-b][1,3,4]thiadiazol-6-yl)-5-methoxybenzo[d]thiazol-7-yl)oxy)methyl)thiazol-2-yl)-N-methyl-N-(tetrahydro-2H-pyran-4-yl)benzamide

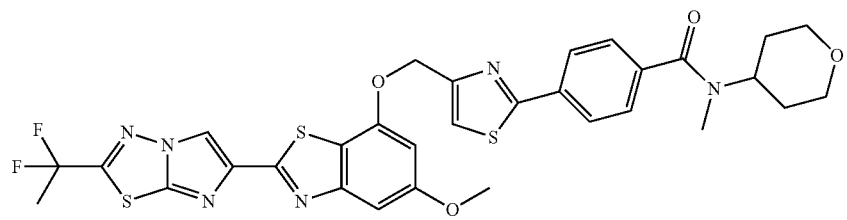 [SMILES: COc1cc(OCc2csc(-c3ccc(C(=O)N(C)C4CCOCC4)cc3)n2)c2sc(-c3cn4nc(C(C)(F)F)sc4n3)nc2c1]

LC (Method B): 2.370 min. HRMS (ESI): calcd for $C_{31}H_{29}F_2N_6O_4S_3$ [M+H]$^+$ m/z 683.1381, found 683.1395.
$^1$HNMR (400 MHz, DMSO-d$_6$) δ ppm 9.05 (s, 1H), 8.00 (d, J=8.2 Hz, 2H), 7.90 (s, 1H), 7.49 (d, J=7.8 Hz, 2H), 7.20 (d, J=2.0 Hz, 1H), 6.92 (d, J=2.0 Hz, 1H), 5.47 (s, 2H), 4.52 (br s, 0.5H), 3.91 (br s, 1H), 3.85 (s, 3H), 3.80 (br s, 1H), 3.59 (br s, 0.5H), 3.42 (br s, 1H), 3.07 (s, 1H), 2.82 (m, 3H), 2.22 (t, J=19.4 Hz, 3H), 1.80 (m, 2H), 1.57 (m, 2H).

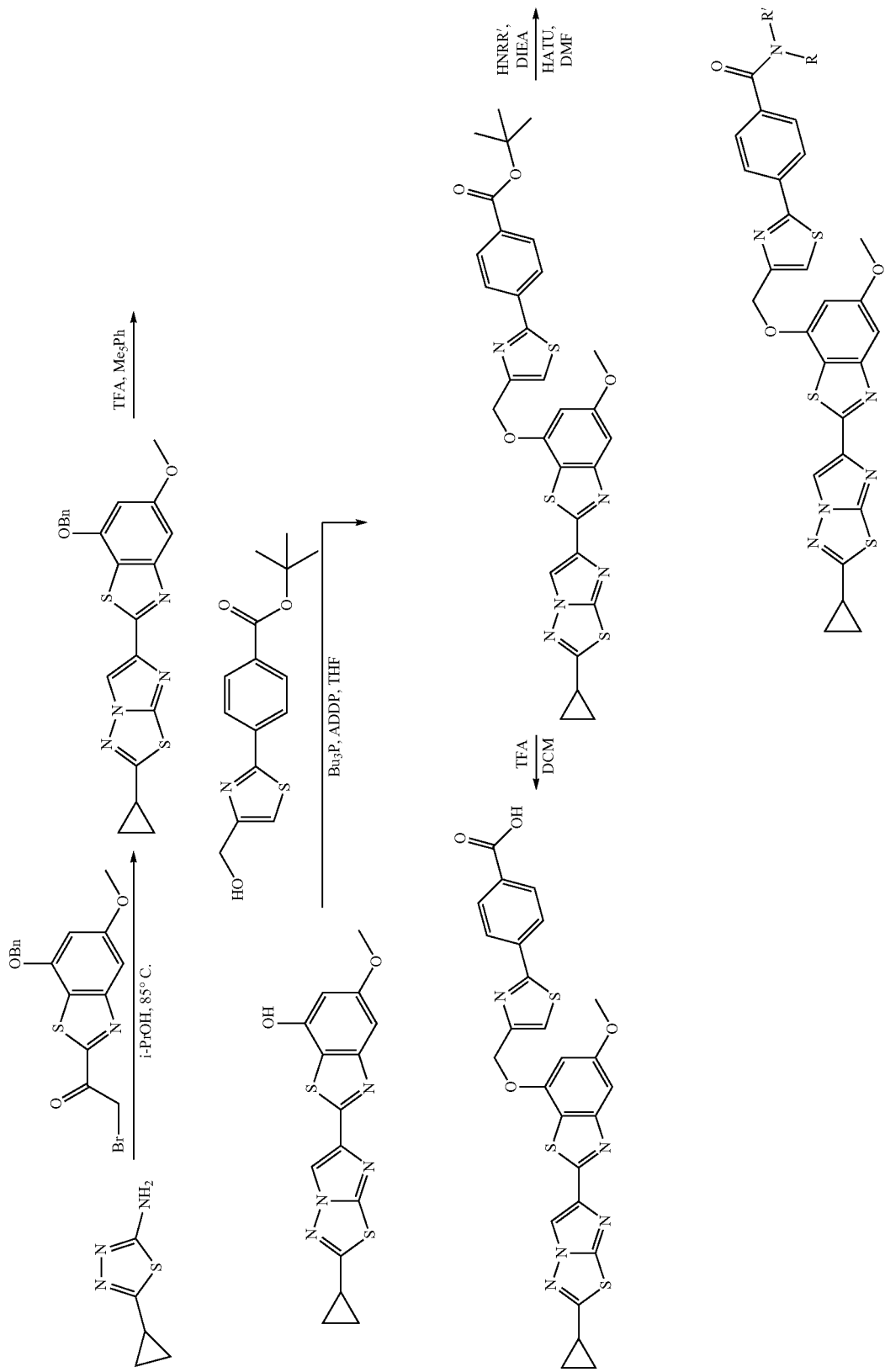

Example 23: 7-(Benzyloxy)-2-(2-cyclopropylimidazo[2,1-b][1,3,4]thiadiazol-6-yl)-5-methoxybenzo[d]thiazole

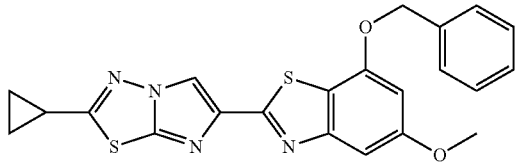 [SMILES: COc1cc(OCc2ccccc2)c2sc(-c3cn4nc(C5CC5)sc4n3)nc2c1]

The title compound was prepared from 5-cyclopropyl-1,3,4-thiadiazol-2-amine and 1-(7-(benzyloxy)-5-methoxybenzo[d]thiazol-2-yl)-2-bromoethanone (Intermediate 1D) using the method described for Example 12. (Method B): 2.418 min HRMS (ESI): calcd for $C_{22}H_{19}N_4O_2S_2$ [M+H]$^+$ m/z 435.0944, found 435.0962. $^1$HNMR (400 MHz, DMSO-$d_6$) δ ppm 8.77 (s, 1H), 7.50 (m, 2H), 7.42 (m, 2H), 7.35 (m, 1H), 7.16 (d, J=2.0 Hz, 1H), 6.75 (d, J=2.0 Hz, 1H), 6.52 (s, 1H), 5.33 (s, 2H), 3.83 (s, 3H), 2.54 (m, 1H), 1.28 (m, 2H), 1.15 (m, 2H).

Example 24 tert-Butyl 4-(4-(((2-(2-cyclopropylimidazo[2,1-b][1,3,4]thiadiazol-6-yl)-5-methoxybenzo[d]thiazol-7-yl)oxy)methyl)thiazol-2-yl)benzoate

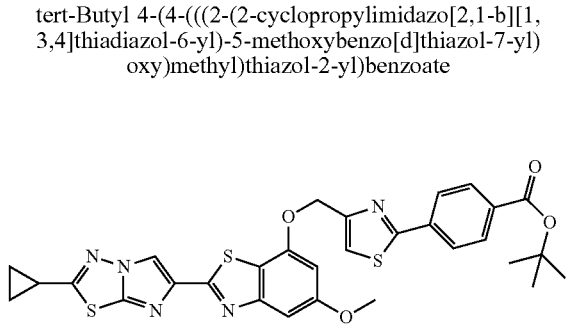

Intermediate 24A. 2-(2-Cyclopropylimidazo[2,1-b][1,3,4]thiadiazol-6-yl)-5-methoxybenzo[d]thiazol-7-ol

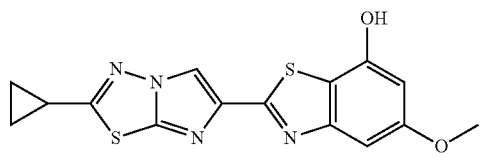 [SMILES: COc1cc(O)c2sc(-c3cn4nc(C5CC5)sc4n3)nc2c1]

To a solution of 1,2,3,4,5-pentamethylbenzene (0.394 g, 2.66 mmol) in TFA (10 mL) was added a solution of 7-(benzyloxy)-2-(2-cyclopropylimidazo[2,1-b][1,3,4]thiadiazol-6-yl)-5-methoxybenzo[d]thiazole (Example 23, 0.330 g, 0.759 mmol) in TFA (4 mL). The reaction mixture was heated at 60° C. for 6 h, after which it was cooled to room temperature and concentrated to dryness. The residue was purified by ISCO using a REDISEP® 40 g column (DCM/EtOAc). Fractions containing the desired product were concentrated to give 2-(2-cyclopropylimidazo[2,1-b][1,3,4]thiadiazol-6-yl)-5-methoxybenzo[d]thiazol-7-ol (0.151 g, 0.438 mmol, 58% yield) as a beige solid. LC (Method B): 2.065 min. MS (APCI): calcd for $C_{15}H_{13}N_4O_2S_2$ [M+H]$^+$ m/z 345.0, found 345.1.

Example 24: tert-Butyl 4-(4-(((2-(2-cyclopropylimidazo[2,1-b][1,3,4]thiadiazol-6-yl)-5-methoxybenzo[d]thiazol-7-yl)oxy)methyl)thiazol-2-yl)benzoate

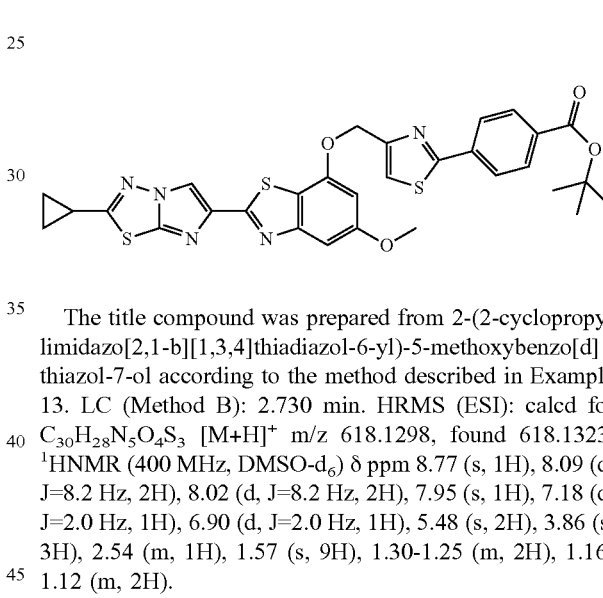

The title compound was prepared from 2-(2-cyclopropylimidazo[2,1-b][1,3,4]thiadiazol-6-yl)-5-methoxybenzo[d]thiazol-7-ol according to the method described in Example 13. LC (Method B): 2.730 min. HRMS (ESI): calcd for $C_{30}H_{28}N_5O_4S_3$ [M+H]$^+$ m/z 618.1298, found 618.1323. $^1$HNMR (400 MHz, DMSO-$d_6$) δ ppm 8.77 (s, 1H), 8.09 (d, J=8.2 Hz, 2H), 8.02 (d, J=8.2 Hz, 2H), 7.95 (s, 1H), 7.18 (d, J=2.0 Hz, 1H), 6.90 (d, J=2.0 Hz, 1H), 5.48 (s, 2H), 3.86 (s, 3H), 2.54 (m, 1H), 1.57 (s, 9H), 1.30-1.25 (m, 2H), 1.16-1.12 (m, 2H).

Example 25

(S)-4-(4-(((2-(2-Cyclopropylimidazo[2,1-b][1,3,4]thiadiazol-6-yl)-5-methoxybenzo[d]thiazol-7-yl)oxy)methyl)thiazol-2-yl)-N-methyl-N-(tetrahydrofuran-3-yl)benzamide

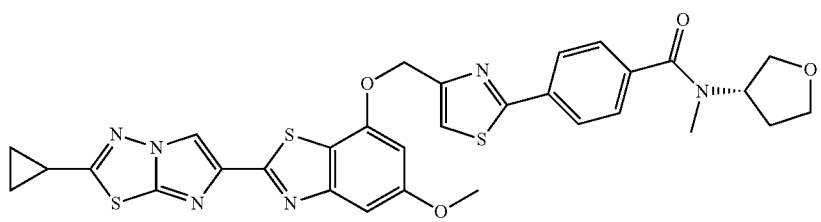 [SMILES: COc1cc(OCc2csc(-c3ccc(C(=O)N(C)[C@H]4CCOC4)cc3)n2)c2sc(-c3cn4nc(C5CC5)sc4n3)nc2c1]

Intermediate 25A. 4-(4-(((2-(2-Cyclopropylimidazo[2,1-b][1,3,4]thiadiazol-6-yl)-5-methoxybenzo[d]thiazol-7-yl)oxy)methyl)thiazol-2-yl)benzoic acid

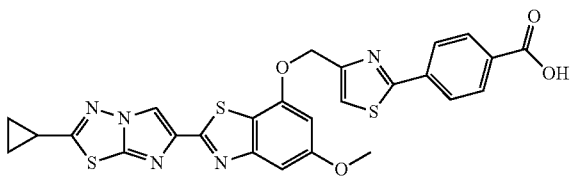 [SMILES: COc1cc(OCc2csc(-c3ccc(C(=O)O)cc3)n2)c2sc(-c3cn4nc(C5CC5)sc4n3)nc2c1]

To a stirred solution of tert-butyl 4-(4-(((2-(2-cyclopropylimidazo[2,1-b][1,3,4]thiadiazol-6-yl)-5-methoxybenzo[d]thiazol-7-yl)oxy)methyl)thiazol-2-yl)benzoate (Example 24, 223 mg, 0.361 mmol) in DCM (5 mL) was added TFA (1 mL). The reaction mixture was stirred at 25° C. for 8 h and then it was concentrated to dryness to give 4-(4-(((2-(2-cyclopropylimidazo[2,1-b][1,3,4]thiadiazol-6-yl)-5-methoxybenzo[d]thiazol-7-yl)oxy)methyl)thiazol-2-yl)benzoic acid (203 mg, 0.361 mmol, 100% yield) as a yellow solid. This material was used as such in the next step. LC (Method B): 2.370 min. MS (APCI): calcd for $C_{26}H_{20}BrN_5O_4S_3$ [M+H]$^+$ m/z, 562.1, found 562.2.

Example 25: (S)-4-(4-(((2-(2-Cyclopropylimidazo[2,1-b][1,3,4]thiadiazol-6-yl)-5-methoxybenzo[d]thiazol-7-yl)oxy)methyl)thiazol-2-yl)-N-methyl-N-(tetrahydrofuran-3-yl)benzamide

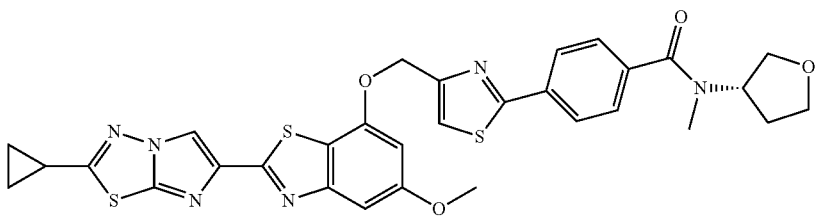 [SMILES: COc1cc(OCc2csc(-c3ccc(C(=O)N(C)[C@H]4CCOC4)cc3)n2)c2sc(-c3cn4nc(C5CC5)sc4n3)nc2c1]

The title compound was prepared according to the general method described in Example 3. LC (Method B): 2.337 min. HRMS (ESI): calcd for $C_{31}H_{29}N_6O_4S_3$ [M+H]$^+$645.1407, found 645.1435. $^1$HNMR (400 MHz, DMSO-d$_6$) δ ppm 8.77 (s, 1H), 8.02 (d, J=8.6 Hz, 2H), 7.91 (s, 1H), 7.52 (m, 2H), 7.18 (d, J=2.0 Hz, 1H), 6.90 (d, J=2.0 Hz, 1H), 5.47 (s, 2H), 5.16 (br s, 1H), 4.33 (br s, 1H), 3.94 (m, 1H), 3.86 (s, 3H), 3.80 (m, 2H), 2.87 (s, 3H), 2.53 (m, 1H), 2.15 (br s, 1H), 1.96 (m, 1H), 1.30-1.25 (m, 2H), 1.14 (m, 2H).

Examples 26-29 were prepared according to the general method described in Example 3 above;

Example 26: (S)-(4-(4-(((2-(2-Cyclopropylimidazo[2,1-b][1,3,4]thiadiazol-6-yl)-5-methoxybenzo[d]thiazol-7-yl)oxy)methyl)thiazol-2-yl)phenyl)(3-hydroxypiperidin-1-yl)methanone

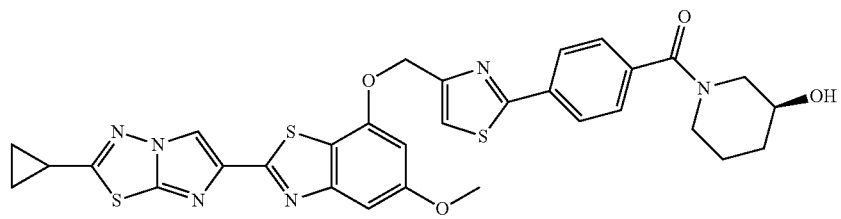 [SMILES: COc1cc(OCc2csc(-c3ccc(C(=O)N4CCC[C@H](O)C4)cc3)n2)c2sc(-c3cn4nc(C5CC5)sc4n3)nc2c1]

LC (Method B): 2.305 min. HRMS (ESI): calcd for $C_{31}H_{29}N_6O_4S_3$ [M+H]$^+$ m/z 645.1407, found 645.1441. $^1$HNMR (400 MHz, DMSO-d$_6$) δ ppm 8.77 (s, 1H), 8.01 (dd, J=2.0, 8.6 Hz, 2H), 7.90 (s, 1H), 7.52 (br s, 2H), 7.17 (d, J=1.6 Hz, 1H), 6.89 (d, J=1.6 Hz, 1H), 5.47 (s, 2H), 4.17 (m, 1H), 3.86 (s, 3H), 3.78 (m, 1.5H), 3.28 (m, 1.5H), 3.04-2.83 (m, 2H), 2.54 (m, 1H), 1.86-1.61 (m, 2H), 1.43 (m, 2H), 1.30-1.25 (m, 2H), 1.14 (m, 2H).

Example 27: N-(Cyanomethyl)-4-(4-(((2-(2-cyclopropylimidazo[2,1-b][1,3,4]thiadiazol-6-yl)-5-methoxybenzo[d]thiazol-7-yl)oxy)methyl)thiazol-2-yl)-N-methylbenzamide

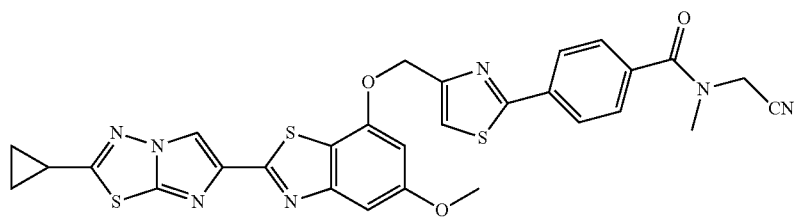 [SMILES: COc1cc(OCc2csc(-c3ccc(C(=O)N(C)CC#N)cc3)n2)c2sc(-c3cn4nc(C5CC5)sc4n3)nc2c1]

LC (Method B): 2.215 min. HRMS (ESI): calcd for $C_{29}H_{24}N_7O_3S_3$ [M+H]$^+$ m/z 614.1097, found 614.1141. $^1$HNMR (400 MHz, DMSO-d$_6$) δ ppm 8.77 (s, 1H), 8.06 (d, J=8.6 Hz, 2H), 7.93 (s, 1H), 7.62 (d, J=7.8 Hz, 2H), 7.18 (d, J=2.0 Hz, 1H), 6.90 (d, J=2.0 Hz, 1H), 5.47 (s, 2H), 4.55 (s, 2H), 3.86 (s, 3H), 3.05 (s, 3H), 2.54 (m, 1H), 1.30-1.25 (m, 2H), 1.14 (m, 2H).

Example 28: 4-(4-(((2-(2-Cyclopropylimidazo[2,1-b][1,3,4]thiadiazol-6-yl)-5-methoxybenzo[d]thiazol-7-yl)oxy)methyl)thiazol-2-yl)-N,N-dimethylbenzamide

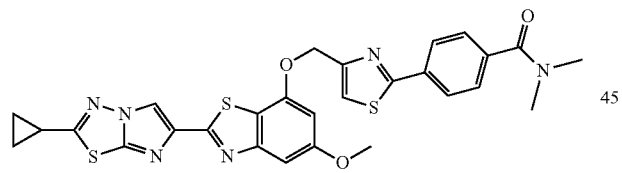

LC (Method B): 2.350 min. HRMS (ESI): calcd for $C_{28}H_{24}N_6O_3S_3$ [M+H]$^+$ m/z 589.1106, found 589.1163. $^1$HNMR (400 MHz, DMSO-d$_6$) δ ppm 8.77 (s, 1H), 8.01 (d, J=1.8, 8.6 Hz, 2H), 7.90 (s, 1H), 7.54 (dt, J=2.0, 8.6 Hz, 2H), 7.18 (d, J=2.0 Hz, 1H), 6.90 (d, J=2.0 Hz, 1H), 5.47 (s, 2H), 3.86 (s, 3H), 3.00 (br s, 3H), 2.94 (br s, 3H), 2.54 (m, 1H), 1.30-1.25 (m, 2H), 1.14 (m, 2H).

Example 29: N-(tert-Butyl)-4-(4-(((2-(2-cyclopropylimidazo[2,1-b][1,3,4]thiadiazol-6-yl)-5-methoxybenzo[d]thiazol-7-yl)oxy)methyl)thiazol-2-yl)-N-(2-hydroxyethyl)benzamide

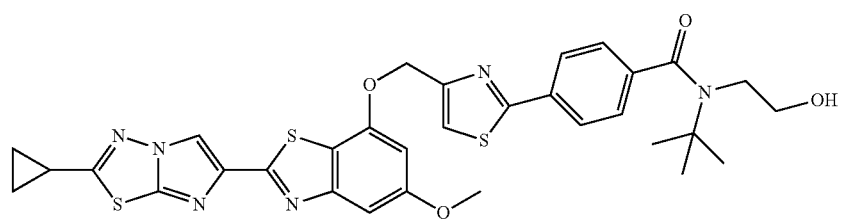 [SMILES: COc1cc(OCc2csc(-c3ccc(C(=O)N(CCO)C(C)(C)C)cc3)n2)c2sc(-c3cn4nc(C5CC5)sc4n3)nc2c1]

LC (Method B): 2.187 min. HRMS (ESI): calcd for $C_{32}H_{33}N_6O_4S_3$ [M+H]$^+$ m/z 661.1720, found 661.1776. $^1$HNMR (400 MHz, DMSO-d$_6$) δ ppm 8.77 (s, 1H), 8.36 (dd, J=1.2, 4.3 Hz, 1H), 8.13 (m, 1H), 8.10 (s, 3H), 7.98 (s, 1H), 7.18 (d, J=2.3 Hz, 1H), 7.16 (m, 1H), 6.90 (d, J=2.0 Hz, 1H), 5.48 (s, 2H), 4.45 (t, J=5.3 Hz, 2H), 3.86 (s, 3H), 3.20 (br s, 2H), 2.54 (m, 1H), 1.30-1.25 (m, 2H), 1.22 (s, 8H), 1.14 (m, 2H).

trated to dryness. The residue was purified by ISCO (EtOAc-DCM) to give 7-(benzyloxy)-2-(2-ethylimidazo[2,1-b][1,3,4]thiadiazol-6-yl)-5-methoxybenzo[d]thiazole (0.425 g, 1.01 mmol, 24%) as a beige solid. LC (Method B): 2.379 min. HRMS (ESI): calcd for $C_{21}H_{19}N_4O_2S_2$ [M+H]$^E$ m/z 423.0871, found 423.0901. $^1$HNMR (400 MHz, DMSO-d$_6$) δ ppm 8.83 (s, 1H), 7.50 (m, 2H), 7.42 (m, 2H), 7.35 (m, 1H), 7.16 (d, J=2.0 Hz, 1H), 6.76 (d, J=2.0 Hz, 1H), 5.34 (s, 2H), 3.84 (s, 3H), 3.12 (q, J=7.4 Hz, 2H), 1.36 (t, J=7.6 Hz, 3H).

Scheme 7

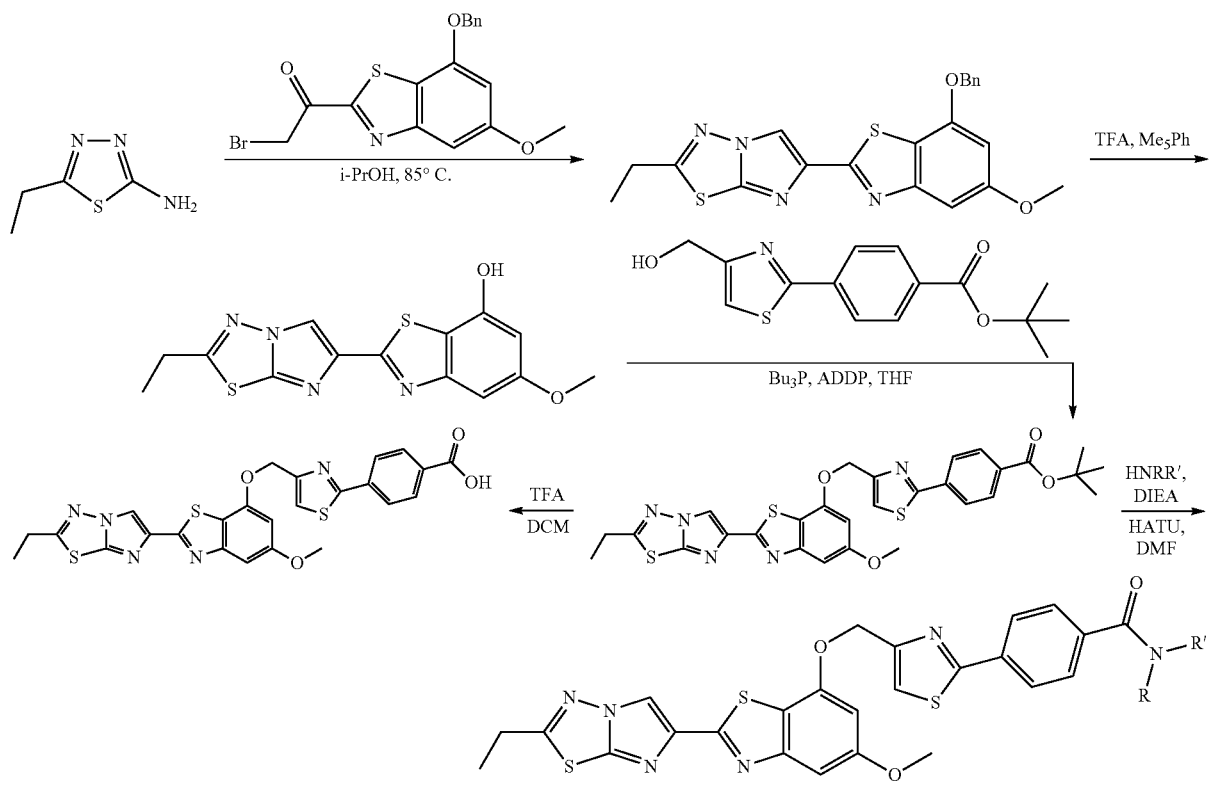

Example 30: 7-(Benzyloxy)-2-(2-ethylimidazo[2,1-b][1,3,4]thiadiazol-6-yl)-5-methoxybenzo[d]thiazole

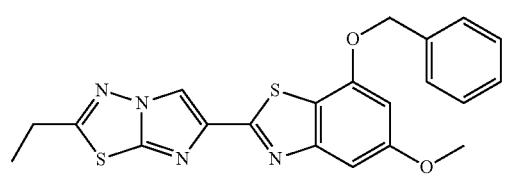 [SMILES: CCc1nn2cc(-c3nc4cc(OC)cc(OCc5ccccc5)c4s3)nc2s1]

A sealable vessel was charged with 5-ethyl-1,3,4-thiadiazol-2-amine (1.08 g, 8.36 mmol), 1-(7-(benzyloxy)-5-methoxybenzo[d]thiazol-2-yl)-2-bromoethanone (Intermediate 1D, 1.64 g, 4.18 mmol) and isopropanol (25 mL). The reaction mixture was heated at 85° C. for 4 h, after which it was transferred to a microwaveable vessel and heated at 155° C. for 45 min. The cooled reaction mixture was then concentrated and the concentrate was partitioned with ethyl acetate-saturated aqueous sodium bicarbonate. The organic phase was separated, dried (MgSO$_4$), filtered and concen- Example 31 tert-Butyl 4-(4-(((2-(2-ethylimidazo[2,1-b][1,3,4]thiadiazol-6-yl)-5-methoxybenzo[d]thiazol-7-yl)oxy)methyl)thiazol-2-yl)benzoate

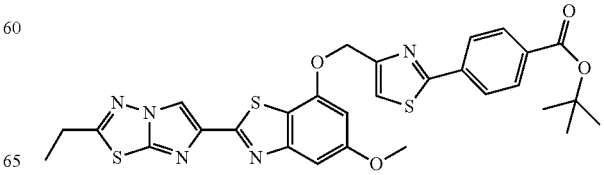

Intermediate 31A. 2-(2-Ethylimidazo[2,1-b][1,3,4]thiadiazol-6-yl)-5-methoxybenzo[d]thiazol-7-ol

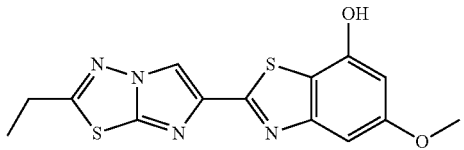 [SMILES: CCc1nn2cc(-c3nc4cc(OC)cc(O)c4s3)nc2s1]

To a solution of 1,2,3,4,5-pentamethylbenzene (491 mg, 3.31 mmol) in TFA (12 mL) was added a solution of 7-(benzyloxy)-2-(2-ethylimidazo[2,1-b][1,3,4]thiadiazol-6-yl)-5-methoxybenzo[d]thiazole (Example 30, 400 mg, 0.947 mmol) in TFA (2.5 mL). The reaction mixture was heated at 60° C. for 6 h, after which it was cooled to room temperature and concentrated to dryness. The residue was purified by ISCO using DCM and [DCM:MeOH:AcOH](50:45:5) as eluent to give the impure product as a brown solid. Repurification by ISCO using DCM:EtOAc as eluent gave pure 2-(2-ethylimidazo[2,1-b][1,3,4]thiadiazol-6-yl)-5-methoxybenzo[d]thiazol-7-ol (201 mg, 0.605 mmol, 64% yield) as a beige solid. LC (Method B): 2.004 min HRMS (ESI): calcd for $C_{14}H_{13}N_4O_2S_2$ $[M+H]^+$ m/z 333.0474, found 333.0515. $^1$HNMR (400 MHz, DMSO-$d_6$) δ ppm 10.57 (s, 1H), 8.81 (s, 1H), 7.03 (d, J=2.3 Hz, 1H), 6.47 (d, J=2.3 Hz, 1H), 3.80 (s, 3H), 3.12 (q, J=7.4 Hz, 2H), 1.36 (t, J=7.4 Hz, 3H).

Example 31: tert-Butyl 4-(4-(((2-(2-ethylimidazo[2,1-b][1,3,4]thiadiazol-6-yl)-5-methoxybenzo[d]thiazol-7-yl)oxy)methyl)thiazol-2-yl)benzoate

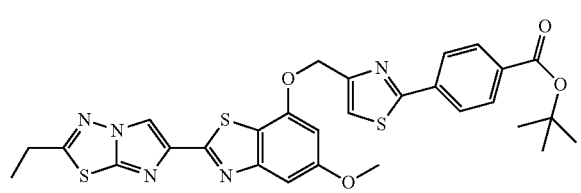 [SMILES: CCc1nn2cc(-c3nc4cc(OC)cc(OCc5csc(-c6ccc(C(=O)OC(C)(C)C)cc6)n5)c4s3)nc2s1]

To a flame-dried 100 ml round bottomed flask containing 2-(2-ethylimidazo[2,1-b][1,3,4]thiadiazol-6-yl)-5-methoxybenzo[d]thiazol-7-ol (173 mg, 0.520 mmol) and tert-butyl 4-(4-(hydroxymethyl)thiazol-2-yl)benzoate (Intermediate 1J, 152 mg, 0.520 mmol) in dry THF (10 mL) was added tributylphosphine (0.338 ml, 1.301 mmol). The resulting solution was added a solution of ADDP (328 mg, 1.301 mmol) in THF (10 mL), dropwise over 30 min. After stirring for an additional 30 min the reaction mixture was partitioned with EtOAc-saturated aqueous NaHCO$_3$. The organic phase was separated, washed with brine, dried (MgSO$_4$), filtered and concentrated to dryness. The residue was purified by ISCO using DCM-EtOAc as eluent to give tert-butyl 4-(4-(((2-(2-ethylimidazo[2,1-b][1,3,4]thiadiazol-6-yl)-5-methoxybenzo[d]thiazol-7-yl)oxy)methyl)thiazol-2-yl)benzoate (263 mg, 0.434 mmol, 83% yield) as a beige solid. LC (Method B): 2.664 min. HRMS (ESI) calcd for $C_{29}H_{28}N_5O_4S_3$ $[M+H]^+$ m/z 606.1298, found 606.1332. $^1$HNMR (400 MHz, DMSO-$d_6$) δ ppm 8.84 (s, 1H), 8.09 (m, 2H), 8.02 (m, 2H), 7.96 (s, 1H), 7.19 (d, J=2.0 Hz, 1H), 6.91 (d, J=2.0 Hz, 1H), 5.49 (s, 1H), 3.86 (s, 3H), 3.12 (q, J=7.4 Hz, 2H), 1.57 (s, 9H), 1.35 (t, J=7.6 Hz, 3H).

Example 32: 4-(4-(((2-(2-Ethylimidazo[2,1-b][1,3,4]thiadiazol-6-yl)-5-methoxybenzo[d]thiazol-7-yl)oxy)methyl)thiazol-2-yl)-N-(3-hydroxy-2,2-dimethylpropyl)benzamide

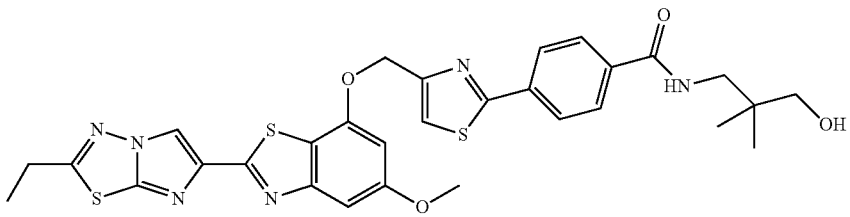 [SMILES: CCc1nn2cc(-c3nc4cc(OC)cc(OCc5csc(-c6ccc(C(=O)NCC(C)(C)CO)cc6)n5)c4s3)nc2s1]

To a stirred solution of tert-butyl 4-(4-(((2-(2-ethylimidazo[2,1-b][1,3,4]thiadiazol-6-yl)-5-methoxybenzo[d]thiazol-7-yl)oxy)methyl)thiazol-2-yl)benzoate (230 mg, 0.380 mmol) in DCM (5 mL) was added TFA (0.5 mL). The reaction mixture was stirred at room temperature for 16 h and then it was concentrated to dryness to give 4-(4-(((2-(2-ethylimidazo[2,1-b][1,3,4]thiadiazol-6-yl)-5-methoxybenzo[d]thiazol-7-yl)oxy)methyl)thiazol-2-yl)benzoic acid (209 mg, 0.380 mmol, 100% yield) as a yellow solid. LC (Method B): 2.305 min HRMS (ESI): calcd for $C_{25}H_{20}N_5O_4S_3$ $[M+H]^+$ m/z 550.0677, found 550.0638. $^1$HNMR (400 MHz, DMSO-$d_6$) 8.84 (s, 1H), 8.07 (m, 4H), 7.96 (s, 1H), 7.18 (d, J=2.0 Hz, 1H), 6.90 (d, J=2.0 Hz, 1H), 5.48 (s, 2H), 3.86 (s, 3H), 3.11 (quartet, J=7.4 Hz, 2H), 1.35 (t, J=7.4 Hz, 3H).

To a stirred solution of 4-(4-(((2-(2-ethylimidazo[2,1-b][1,3,4]thiadiazol-6-yl)-5-methoxybenzo[d]thiazol-7-yl)oxy)methyl)thiazol-2-yl)benzoic acid (25 mg, 0.045 mmol) and 3-amino-2,2-dimethylpropan-1-ol (4.7 mg, 0.045 mmol) in DMF (1 mL) was added DIEA (0.032 ml, 0.182 mmol), followed by HATU (17.3 mg, 0.045 mmol). The reaction mixture was stirred at room temperature for 16 h and then it was diluted with water (5 mL). The resulting precipitate was filtered off, rinsed with acetonitrile (1 mL) then dried under reduced pressure to give 4-(4-(((2-(2-ethylimidazo[2,1-b][1,3,4]thiadiazol-6-yl)-5-methoxybenzo[d]thiazol-7-yl)oxy)methyl)thiazol-2-yl)-N-(3-hydroxy-2,2-dimethylpropyl)benzamide (18 mg, 0.028 mmol, 62% yield) as a white solid. LC (Method B): 2.358 min. HRMS (ESI): calcd for $C_{30}H_{31}N_6O_4S_3$ $[M+H]^+$ m/z 635.1563, found 635.1563. $^1$HNMR (400 MHz, DMSO-$d_6$) δ ppm 8.84 (s, 1H), 8.51 (t, J=6.3 Hz, 1H), 8.05 (m, 2H), 7.97 (m, 2H), 7.93 (m, 2H), 7.19 (d, J=2.0 Hz, 1H), 6.91 (d, J=2.0 Hz, 1H), 5.48 (s, 2H), 3.86 (s, 3H), 3.18 (d, J=6.3 Hz, 2H), 3.14 (s, 2H), 3.11 (q, J=7.6 Hz, 2H), 1.35 (t, J=7.4 Hz, 3H), 0.84 (s, 6H).

Examples 33-36 were prepared according to the general method described in Example 32 above;

Example 33: (S)-(4-(4-(((2-(2-Ethylimidazo[2,1-b][1,3,4]thiadiazol-6-yl)-5-methoxybenzo[d]thiazol-7-yl)oxy)methyl)thiazol-2-yl)phenyl)(3-hydroxypiperidin-1-yl)methanone

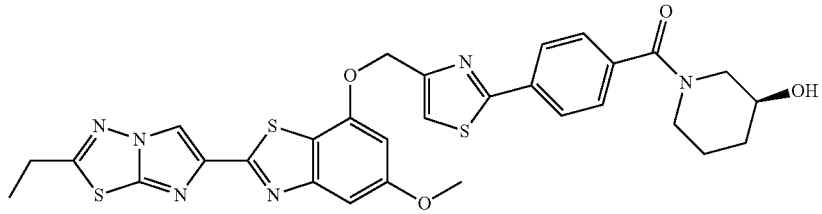 [SMILES: CCc1nn2cc(-c3nc4cc(OC)cc(OCc5csc(-c6ccc(C(=O)N7CCC[C@H](O)C7)cc6)n5)c4s3)nc2s1]

LC (Method B): 2.297 min. HRMS (ESI): calcd for $C_{30}H_{29}N_6O_4S_3$ [M+H]$^+$ m/z 633.1407, found 633.1428. $^1$HNMR (400 MHz, DMSO-d$_6$) δ ppm 8.83 (s, 1H), 8.01 (m, 2H), 7.90 (s, 1H), 7.52 (m, 2H), 7.18 (d, J=2.0 Hz, 1H), 6.90 (d, J=2.0 Hz, 1H), 5.47 (s, 2H), 4.18 (m, 0.5H), 3.86 (s, 3H), 3.79 (m, 1H), 3.62-3.52 (m, 2.5H), 3.28 (m, 1H), 3.11 (q, J=7.5 Hz, 2H), 3.05-2.82 (m, 1H), 1.90-1.60 (m, 2H), 1.43 (m, 2H), 1.35 (t, J=7.4 Hz, 3H).

Example 34: (S)-4-(4-(((2-(2-Ethylimidazo[2,1-b][1,3,4]thiadiazol-6-yl)-5-methoxybenzo[d]thiazol-7-yl)oxy)methyl)thiazol-2-yl)-N-methyl-N-(tetrahydrofuran-3-yl)benzamide

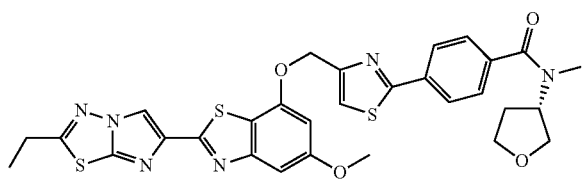 [SMILES: CCc1nn2cc(-c3nc4cc(OC)cc(OCc5csc(-c6ccc(C(=O)N(C)[C@H]7CCOC7)cc6)n5)c4s3)nc2s1]

LC (Method B): 2.334 min. HRMS (ESI): calcd for $C_{30}H_{29}N_6O_4S_3$ [M+H]$^+$ m/z 633.1407, found 633.1419. $^1$HNMR (400 MHz, DMSO-d$_6$) δ ppm 8.83 (s, 1H), 8.02 (d, J=8.6 Hz, 2H), 7.91 (s, 1H), 7.51 (m, 2H), 7.18 (d, J=2.0 Hz, 1H), 6.90 (d, J=2.0 Hz, 1H), 5.47 (s, 2H), 5.16 (br s, 0.5H), 4.33 (br s, 0.5H), 3.94 (m, 1H), 3.86 (s, 3H), 3.79 (m, 1H), 3.59 (br s, 1H), 3.38 (m, 5H), 3.11 (q, J=7.4 Hz, 2H), 2.87 (br s, 13H), 2.14 (br s, 1H), 1.96 (m, 1H), 1.35 (t, J=7.4 Hz, 3H).

Example 35: 4-(4-(((2-(2-Ethylimidazo[2,1-b][1,3,4]thiadiazol-6-yl)-5-methoxybenzo[d]thiazol-7-yl)oxy)methyl)thiazol-2-yl)-N,N-dimethylbenzamide

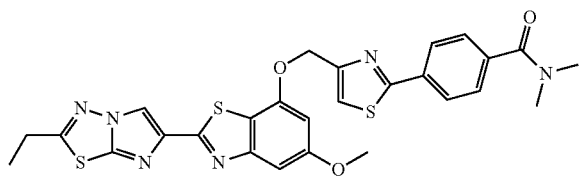 [SMILES: CCc1nn2cc(-c3nc4cc(OC)cc(OCc5csc(-c6ccc(C(=O)N(C)C)cc6)n5)c4s3)nc2s1]

LC (Method B): 2.275 min. HRMS (ESI): calcd for $C_{27}H_{25}N_6O_3S_3$ [M+H]$^+$ m/z 577.1145, found 577.1163. $^1$HNMR (400 MHz, DMSO-d$_6$) δ ppm 8.84 (s, 1H), 8.01 (m, 2H), 7.91 (s, 1H), 7.54 (m, 2H), 7.18 (d, J=2.0 Hz, 1H), 6.90 (d, J=2.0 Hz, 1H), 5.47 (s, 2H), 3.86 (s, 3H), 3.12 (q, J=7.4 Hz, 2H), 3.00 (br s, 3H), 2.94 (br s, 3H), 1.35 (t, J=7.4 Hz, 3H).

Example 36: (4-(4-(((2-(2-Ethylimidazo[2,1-b][1,3,4]thiadiazol-6-yl)-5-methoxybenzo[d]thiazol-7-yl)oxy)methyl)thiazol-2-yl)phenyl)(4-(2-hydroxyethyl)piperidin-1-yl)methanone

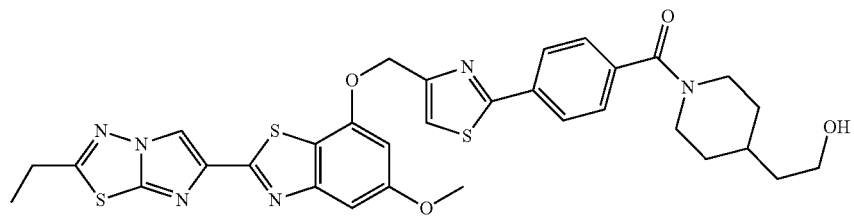 [SMILES: CCc1nn2cc(-c3nc4cc(OC)cc(OCc5csc(-c6ccc(C(=O)N7CCC(CCO)CC7)cc6)n5)c4s3)nc2s1]

LC (Method B): 2.275 min. HRMS (ESI): calcd for $C_{32}H_{33}N_6O_4S_3$ [M+H]$^+$ m/z 661.1725, found 661.1778. $^1$HNMR (400 MHz, DMSO-d$_6$) δ ppm 8.84 (s, 1H), 8.01 (m, 2H), 7.90 (s, 1H), 7.50 (m, 2H), 7.19 (d, J=2.0 Hz, 1H), 6.90 (d, J=2.0 Hz, 1H), 5.47 (s, 2H), 4.44 (br s, 1H), 3.86 (s, 3H), 3.54 (m, 3H), 3.44 (t, J=6.7 Hz, 2H), 3.12 (q, J=7.4 Hz, 2H), 3.01 (m, 1H), 2.76 (m, 1H), 1.78-1.58 (m, 3H), 1.39 (m, 1H), 1.35 (t, J=7.6 Hz, 3H), 1.10 (m, 2H).

Scheme 8
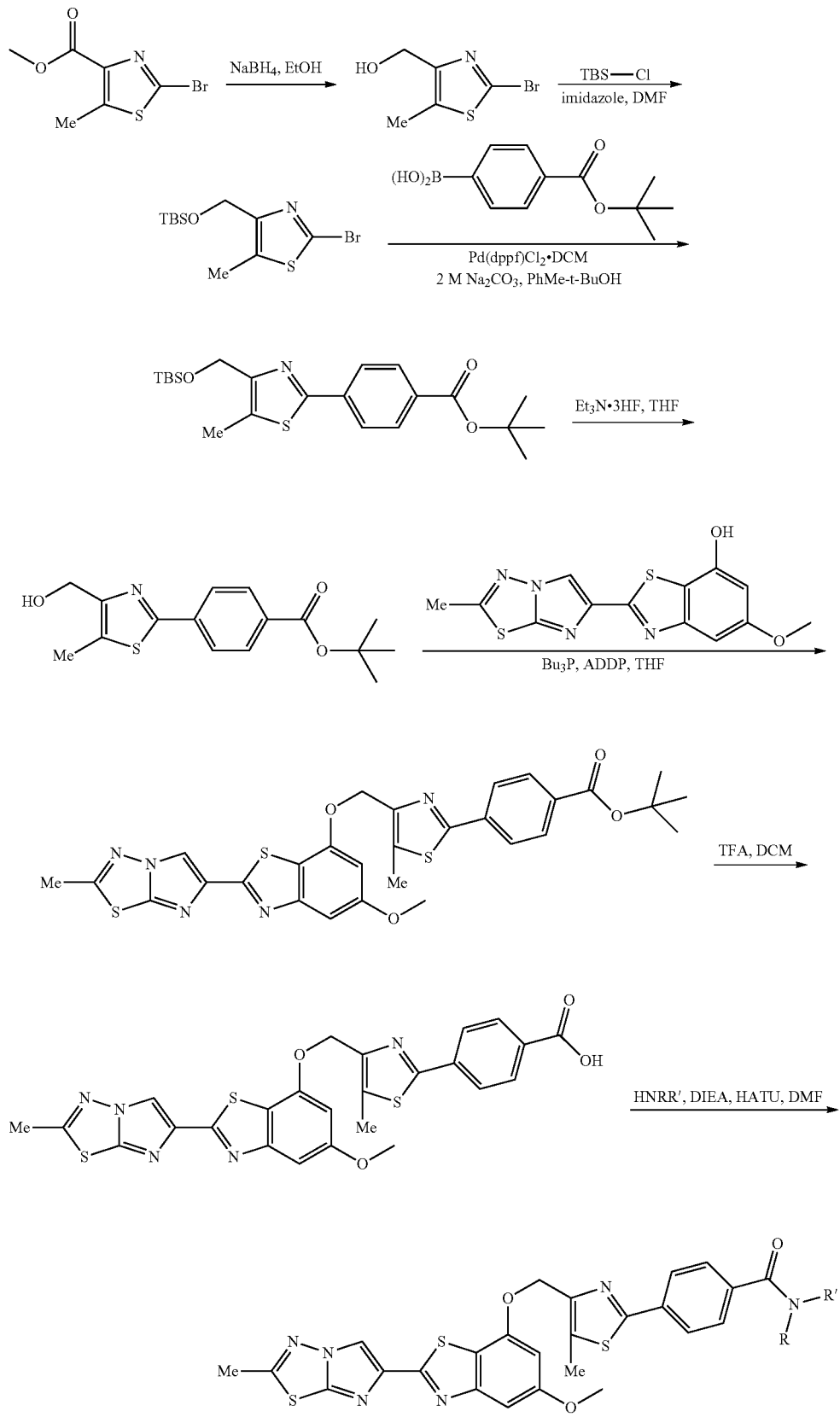

Example 37 tert-Butyl 4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoate

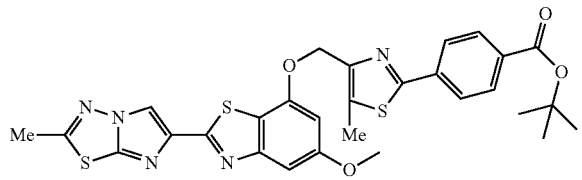 [SMILES: COc1cc(OCc2nc(-c3ccc(C(=O)OC(C)(C)C)cc3)sc2C)c2sc(-c3cn4nc(C)sc4n3)nc2c1]

Intermediate 37A. (2-Bromo-5-methylthiazol-4-yl)methanol

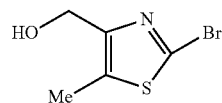

The title compound was prepared from methyl 2-bromothiazole-4-carboxylate according to the method described in Intermediate 1G. MS (APCI): calcd for C$_5$H$_7$BrNOS [M+H]$^+$ m/z, 207.94, found 208.0.

Intermediate 37B. 2-Bromo-4-(((tert-butyldimethylsilyl)oxy)methyl)-5-methylthiazole

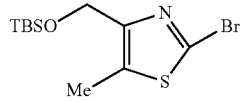

The title compound was prepared according to the method described in Intermediate 1H. MS (APCI): calcd for C$_{11}$H$_{21}$BrNOSSi [M+H]$^+$ m/z, 322.03, found 322.0. $^1$HNMR (400 MHz, CDCl$_3$) δ ppm 4.64 (s, 2H), 2.34 (s, 3H), 0.81 (s, 9H), 0.00 (s, 6H).

Intermediate 37C. tert-Butyl 4-(4-(((tert-butyldimethylsilyl)oxy)methyl)-5-methylthiazol-2-yl)benzoate

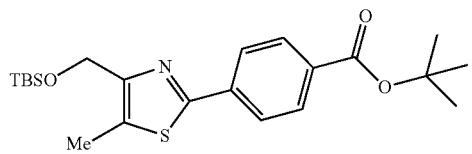 [SMILES: Cc1sc(-c2ccc(C(=O)OC(C)(C)C)cc2)nc1CO[Si](C)(C)C(C)(C)C]

The title compound was prepared according to the method described in Intermediate 1I. LC (Method B): 2.966 min. HRMS (ESI): calcd for C$_{22}$H$_{34}$NO$_3$SSi [M+H]$^+$ 420.2029, found 420.2038. $^1$HNMR (400 MHz, CDCl$_3$) δ ppm 8.10- 7.97 (m, 2H), 7.97-7.85 (m, 2H), 4.86 (s, 2H), 2.54 (s, 3H), 1.62 (s, 9H), 0.94 (s, 9H), 0.14 (s, 6H).

Intermediate 37D. tert-Butyl 4-(4-(hydroxymethyl)-5-methylthiazol-2-yl)benzoate

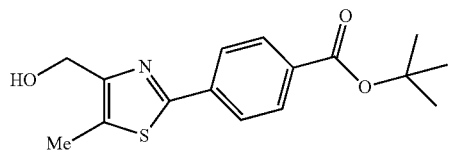 [SMILES: Cc1sc(-c2ccc(C(=O)OC(C)(C)C)cc2)nc1CO]

The title compound was prepared according to the method described in Intermediate 1J. LC (Method B): 2.225 min. HRMS (ESI): calcd for C$_{16}$H$_{20}$NO$_3$S [M+H]$^+$ m/z, 306.1164, found 306.1161. $^1$HNMR (400 MHz, CDCl$_3$) δ ppm 8.07-7.99 (m, 2H), 7.99-7.87 (m, 2H), 4.74 (d, J=5.8 Hz, 2H), 2.50 (s, 3H), 2.35 (t, J=5.8 Hz, 1H), 1.62 (s, 9H).

Example 37: tert-Butyl 4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoate

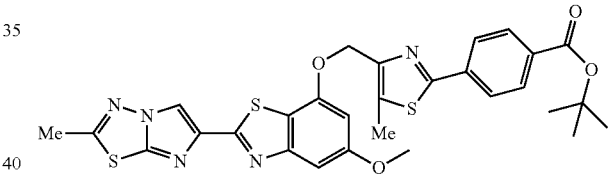

To a flame-dried 250 mL round bottomed flask containing 5-methoxy-2-(2-methylimidazo[2,1-b][1,3,4]thiadiazol-6-yl)benzo[d]thiazol-7-ol (Intermediate 1F, 240 mg, 0.754 mmol) and tert-butyl 4-(4-(hydroxymethyl)-5-methylthiazol-2-yl)benzoate (Intermediate 37D, 230 mg, 0.754 mmol) in dry THF (10 mL) was added tributylphosphine (0.489 ml, 1.885 mmol). To the resulting solution was added a solution of ADDP (476 mg, 1.885 mmol) in THF (10 mL), dropwise over 20 min. After stirring for another 30 min, the reaction mixture was partitioned with EtOAc-saturated aqueous sodium bicarbonate. The organic phase was separated, washed with brine, dried (MgSO$_4$), filtered and concentrated to dryness. The residue was purified by ISCO using a REDISEP® 80 g column (DCM-EtOAc) to give tert-butyl 4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoate (174 mg, 0.287 mmol, 38% yield) as a beige solid. LC (Method B): 2.643 min. HRMS (ESI): calcd for C$_{29}$H$_{28}$N$_5$O$_4$S$_3$ [M+H]$^+$ m/z 606.1298, found 606.1343. $^1$HNMR (400 MHz, DMSO-d$_6$) δ ppm 8.82 (s, 1H), 8.01 (s, 4H), 7.18 (s, 1H), 6.93 (s, 1H), 5.43 (s, 2H), 3.86 (s, 3H), 2.76 (s, 3H), 2.60 (s, 3H), 1.56 (s, 9H).

Example 38

(S)-(3-Hydroxypiperidin-1-yl)(4-(4-(((5-methoxy-2-(2-methylimidazo[2,1-b][1,3,4]thiadiazol-6-yl)benzo[d]thiazol-7-yl)oxy)methyl)-5-methylthiazol-2-yl)phenyl)methanone

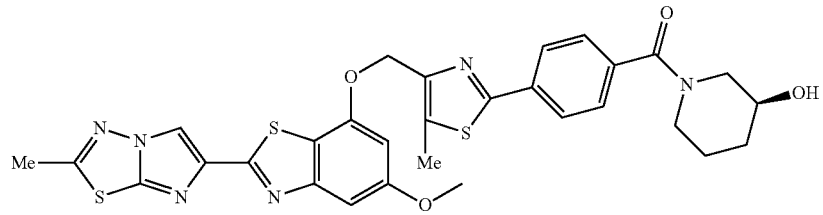 [SMILES: COc1cc(OCc2nc(-c3ccc(C(=O)N4CCC[C@H](O)C4)cc3)sc2C)c2sc(-c3cn4nc(C)sc4n3)nc2c1]

Intermediate 38A. 4-(4-(((5-Methoxy-2-(2-methylimidazo[2,1-b][1,3,4]thiadiazol-6-yl)benzo[d]thiazol-7-yl)oxy)methyl)-5-methylthiazol-2-yl)benzoic acid

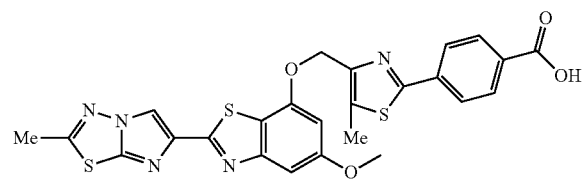 [SMILES: COc1cc(OCc2nc(-c3ccc(C(=O)O)cc3)sc2C)c2sc(-c3cn4nc(C)sc4n3)nc2c1]

To a stirred suspension of tert-butyl 4-(4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoate (168 mg, 0.277 mmol) in DCM (10 mL) was added TFA (1.5 mL) and the resulting solution was stirred at room temperature for 1 h. The reaction mixture was then concentrated to dryness to give 4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoic acid (152 mg, 0.277 mmol, 100%) as a yellow solid. This material was used as such without further purification. LC (Method B): 2.362 min. HRMS (ESI): calcd for $C_{25}H_{20}N_5O_4S_3$ [M+H]$^+$ m/z 550.6072, found 550.6074.

Example 38: (S)-(3-Hydroxypiperidin-1-yl)(4-(4-(((5-methoxy-2-(2-methylimidazo[2,1-b][1,3,4]thiadiazol-6-yl)benzo[d]thiazol-7-yl)oxy)methyl)-5-methylthiazol-2-yl)phenyl)methanone To a stirred solution of 4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzoic acid (0.030 g, 0.054 mmol) and (S)-piperidin-3-ol hydrochloride (7.43 mg, 0.054 mmol) in DMF (1 mL) was added DIEA (0.038 ml, 0.216 mmol), followed by HATU (0.021 g, 0.054 mmol). The reaction mixture was stirred at room temperature for 16 h and then it was diluted with water (5 mL). The desired product was filtered off, rinsed with acetonitrile (1 mL) then dried under reduced pressure to give (S)-(3-hydroxypiperidin-1-yl)(4-(4-(((5-methoxy-2-(2-methylimidazo[2,1-b][1,3,4]thiadiazol-6-yl)benzo[d]thiazol-7-yl)oxy)methyl)-5-methylthiazol-2-yl)phenyl)methanone (0.021 g, 0.033 mmol, 62% yield) as a white solid. LC (Method B): 2.132 min. HRMS (ESI): calcd for $C_{30}H_{29}N_6O_4S_3$ [M+H]$^+$ m/z 633.1407, found 633.1409. $^1$HNMR (400 MHz, DMSO-d$_6$) δ ppm 8.82 (s, 1H), 7.94 (dd, J=1.6, 8.2, Hz, 2H), 7.50 (m, 2H), 7.17 (d, J=2.0 Hz, 1H), 6.93 (d, J=2.0 Hz, 1H), 5.41 (s, 2H), 4.85 (br s, 1H), 4.16 (br s, 1H), 3.86 (s, 3H), 3.78 (m, 1H), 3.54-3.40 (m, 2H), 3.06-2.82 (m, 1H), 2.76 (s, 3H), 2.58 (s, 3H), 1.90-1.59 (m, 1H), 1.42 (m, 2H).

Examples 39-42 were prepared according to the general method described in Example 38 above;

Example 39: (S)-4-(4-(((5-Methoxy-2-(2-methylimidazo[2,1-b][1,3,4]thiadiazol-6-yl)benzo[d]thiazol-7-yl)oxy)methyl)-5-methylthiazol-2-yl)-N-methyl-N-(tetrahydrofuran-3-yl)benzamide

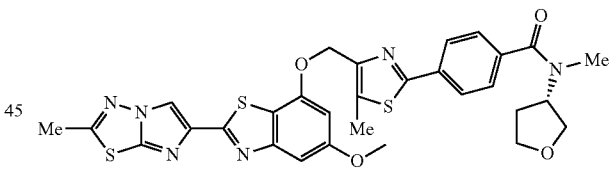

LC (Method B): 2.259 min. HRMS (ESI): calcd for $C_{30}H_{29}N_6O_4S_3$ [M+H]$^+$ m/z 633.1407, found 633.1416. $^1$HNMR (400 MHz, DMSO-d$_6$) δ ppm 8.82 (s, 1H), 7.95 (d, J=8.2 Hz, 2H), 7.50 (m, 2H), 7.17 (d, J=1.6 Hz, 1H), 6.93 (d, J=1.6 Hz, 1H), 5.42 (s, 2H), 3.79 (dd, J=3.9, 9.4 Hz, 1H), 3.59 (m, 2H), 2.87 (br s, 3H), 2.76 (s, 3H), 2.59 (s, 3H), 2.14 (m, 1H), 1.96 (m, 1H).

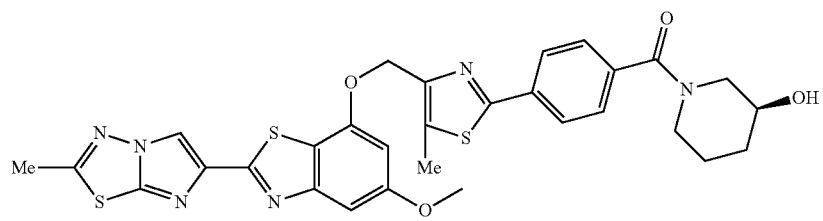 [SMILES: COc1cc(OCc2nc(-c3ccc(C(=O)N4CCC[C@H](O)C4)cc3)sc2C)c2sc(-c3cn4nc(C)sc4n3)nc2c1]

Example 40: N-(3-Hydroxy-2,2-dimethylpropyl)-4-(4-(((5-methoxy-2-(2-methylimidazo[2,1-b][1,3,4]thiadiazol-6-yl)benzo[d]thiazol-7-yl)oxy)methyl)-5-methylthiazol-2-yl)benzamide

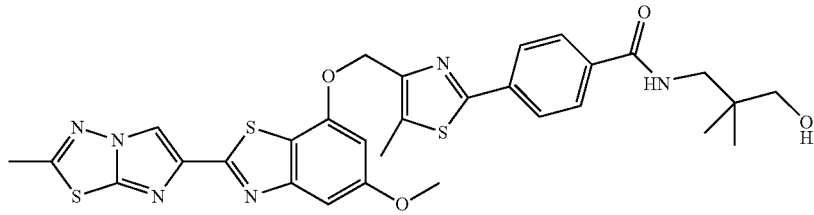 [SMILES: COc1cc(OCc2nc(-c3ccc(C(=O)NCC(C)(C)CO)cc3)sc2C)c2sc(-c3cn4nc(C)sc4n3)nc2c1]

LC (Method B): 2.337 min. HRMS (ESI): calcd for $C_{30}H_{29}N_6O_4S_3$ [M+H]$^+$ m/z 635.1563, found 635.1595. $^1$HNMR (400 MHz, DMSO-d$_6$) δ ppm 8.82 (s, 1H), 8.49 (t, J=6.3 Hz, 1H), 7.96 (m, 4H), 7.18 (d, J=2.0 Hz, 1H), 6.94 (d, J=2.0 Hz, 1H), 5.42 (s, 2H), 3.87 (s, 3H), 3.16 (m, 4H), 2.76 (m, 3H), 2.59 (s, 3H), 0.84 (s, 6H).

Example 41: 4-(4-(((5-Methoxy-2-(2-methylimidazo[2,1-b][1,3,4]thiadiazol-6-yl)benzo[d]thiazol-7-yl)oxy)methyl)-5-methylthiazol-2-yl)-N,N-dimethylbenzamide

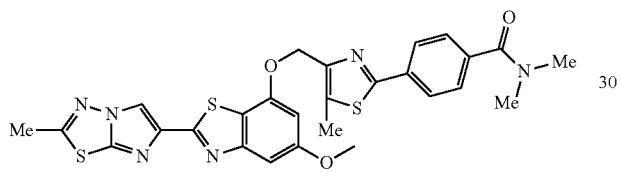

LC (Method B): 2.281 min. HRMS (ESI): calcd for $C_{27}H_{25}N_6O_3S_3$ [M+H]$^+$ m/z 577.1145, found 577.1168. $^1$HNMR (400 MHz, DMSO-d$_6$) δ ppm 8.82 (s, 1H), 7.94 (m, 2H), 7.52 (m, 2H), 7.17 (d, J=2.0 Hz, 1H), 6.93 (d, J=2.0 Hz, 1H), 5.41 (s, 2H), 3.86 (s, 3H), 3.00 (br s, 3H), 2.94 (br s, 3H), 2.76 (s, 3H), 2.59 (s, 3H).

Example 42: (4-(2-Hydroxyethyl)piperidin-1-yl)(4-(4-(((5-methoxy-2-(2-methylimidazo[2,1-b][1,3,4]thiadiazol-6-yl)benzo[d]thiazol-7-yl)oxy)methyl)-5-methylthiazol-2-yl)phenyl)methanone

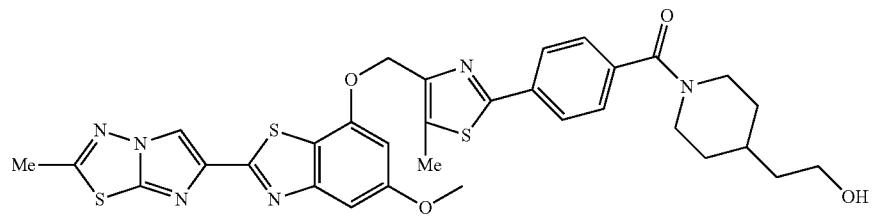 [SMILES: COc1cc(OCc2nc(-c3ccc(C(=O)N4CCC(CCO)CC4)cc3)sc2C)c2sc(-c3cn4nc(C)sc4n3)nc2c1]

LC (Method B): 2.307 min. HRMS (ESI): calcd for $C_{32}H_{33}N_6O_4S_3$ [M+H]$^+$ m/z 661.1720, found 661.1745. $^1$HNMR (400 MHz, DMSO-d$_6$) δ ppm 8.82 (s, 1H), 7.94 (dd, J=2.0, 8.6 Hz, 2H), 7.48 (dd, J=1.6, 8.2 Hz, 2H), 7.17 (m, 1H), 6.93 (d, J=1.6 Hz, 1H), 5.41 (s, 2H), 4.45 (m, 1H), 3.86 (s, 3H), 3.44 (t, J=6.7 Hz, 2H), 3.07-2.92 (m, 2H), 2.76 (s, 3H), 2.58 (s, 3H), 1.77-1.58 (m, 4H), 1.38 (quartet, J=6.3 Hz, 2H), 1.11 (m, 2H).

Scheme 9

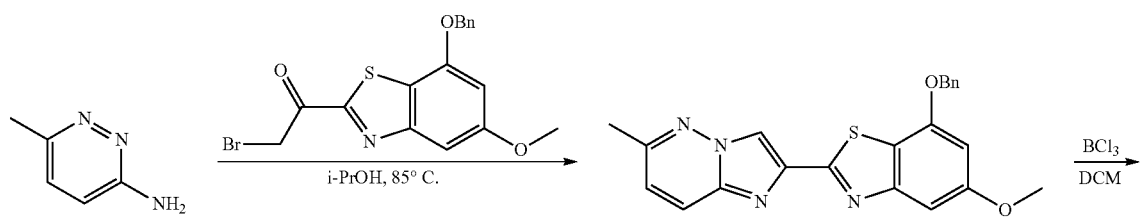

-continued

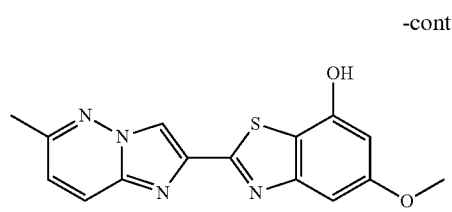 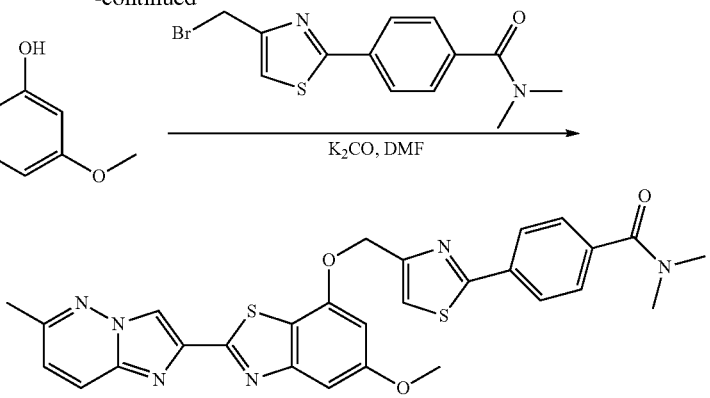

Example 43: 7-(Benzyloxy)-5-methoxy-2-(6-methylimidazo[1,2-b]pyridazin-2-yl)benzo[d]thiazole

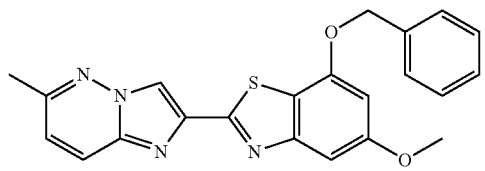 [SMILES: COc1cc(OCc2ccccc2)c2sc(-c3cn4nc(C)ccc4n3)nc2c1]

A sealable tube was charged with 6-methylpyridazin-3-amine (16.0 mg, 0.147 mmol), 1-(7-(benzyloxy)-5-methoxybenzo[d]thiazol-2-yl)-2-bromoethanone (Intermediate 1D, 48 mg, 0.122 mmol) and ethanol (3 mL). The reaction mixture was heated at 85° C. for 2 h and then concentrated to dryness. The residue was dissolved in dichloromethane, washed with saturated aqueous sodium bicarbonate and brine, then dried (MgSO$_4$) and concentrated to dryness. The residue was purified by ISCO using a REDISEP® 12 g column (dichloromethane-ethyl acetate to give 7-(benzyloxy)-5-methoxy-2-(6-methylimidazo[1,2-b]pyridazin-2-yl)benzo[d]thiazole (27 mg, 0.067 mmol, 55% yield) as an orange solid. LC (Method B): 2.341 min HRMS (ESI): calcd for C$_{22}$H$_{19}$N$_4$O$_2$S [M+H]$^+$ m/z, 403.1223, found 403.1223. $^1$H NMR (400 MHz, DMSO-d$_6$) δ ppm 8.80 (s, 1H), 8.11 (d, J=9.4 Hz, 1H), 7.51 (m, 2H), 7.43 (m, 2H), 7.36 (m, 1H), 7.26 (d, J=9.4 Hz, 1H), 7.22 (d, J=2.3 Hz, 1H), 6.79 (d, J=2.0 Hz, 1H), 5.34 (s, 2H), 3.85 (s, 3H), 2.56 (s, 3H).

Intermediate C: 5-Methoxy-2-(6-methylimidazo[1,2-b]pyridazin-2-yl)benzo[d]thiazol-7-ol

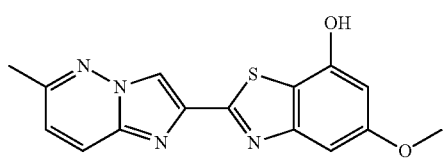

A suspension of 7-(benzyloxy)-5-methoxy-2-(6-methylimidazo[1,2-b]pyridazin-2-yl)benzo[d]thiazole (Example 43, 0.085 g, 0.21 mmol) and 1,2,3,4,5-pentamethylbenzene (0.354 g, 2.39 mmol) in dry dichloromethane (5.5 mL) was cooled to −78° C. under N$_2$ atmosphere and boron trichloride (1.0 M in CH$_2$Cl$_2$, 0.852 ml, 0.852 mmol) was added dropwise. The resulting dark orange-red solution was stirred at −78° C. for 1 h and then it was quenched with saturated aqueous NaHCO$_3$. The cooling bath was removed and the mixture was vigorously stirred for 1.5 h. The resulting golden-yellow suspension was diluted with ethyl acetate and the organic phase was separated, washed with brine, dried (MgSO$_4$) and concentrated to dryness. The residue was purified by ISCO using a REDISEP® 12 g column (DCM-EtOAc) to give 5-methoxy-2-(6-methylimidazo[1,2-b]pyridazin-2-yl)benzo[d]thiazol-7-ol (0.020 g, 0.064 mmol, 19% yield) as a beige solid. LC (Method B): 1.921 min. HRMS (ESI): calcd. for C$_{15}$H$_{13}$N$_4$O$_2$S [M+H]$^+$313.0754, found 313.0757. $^1$H NMR (400 MHz, DMSO-d$_6$) δ ppm 10.62 (br s, 1H), 8.79 (s, 1H), 8.13 (d, J=9.4 Hz, 1H), 7.27 (d, J=9.4 Hz, 1H), 7.09 (d, J=2.3 Hz, 1H), 6.50 (d, J=2.0 Hz, 1H), 3.81 (s, 3H), 2.56 (s, 3H).

Example 44

4-(4-(((5-Methoxy-2-(6-methylimidazo[1,2-b]pyridazin-2-yl)benzo[d]thiazol-7-yl)oxy)methyl)thiazol-2-yl)-N,N-dimethylbenzamide

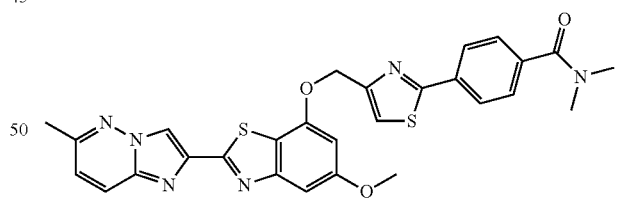

Intermediate 44A. 4-(4-(((tert-Butyldimethylsilyl)oxy)methyl)thiazol-2-yl)-N,N-dimethylbenzamide

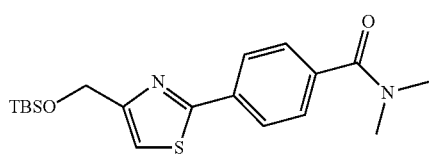 [SMILES: CN(C)C(=O)c1ccc(-c2nc(CO[Si](C)(C)C(C)(C)C)cs2)cc1]

To a mixture of 2-bromo-4-(((tert-butyldimethylsilyl)oxy)methyl)thiazole (Intermediate 1H, 3.00 g, 9.73 mmol) and (4-(dimethylcarbamoyl)phenyl)boronic acid (2.82 g, 14.61 mmol) in toluene:ethanol (3:1, 120 mL) was added 2 M Na$_2$CO$_3$ (6.0 mL, 12.0 mmol) and the mixture was purged with a stream of nitrogen bubbles in a sealable flask for 10 min. To this mixture was added Pd(dppf)Cl$_2$.DCM (500 mg, 0.61 mmol), the flask was sealed and the mixture was stirred at 95° C. (oil bath temperature) for 2 h. The cooled mixture was partitioned with EtOAc-saturated aqueous sodium bicarbonate and the organic phase was separated, washed with brine, dried over MgSO$_4$ and evaporated to give a light yellow gum. Flash chromatography (0-20% EtOAc-DCM) afforded the title compound (3.24 g, 88%) as a colorless gum. LC (Method B): 2.401 min. $^1$HNMR (400 MHz, DMSO-d$_6$) δ ppm 7.97 (d, J=8.2 Hz, 2H), 7.52 (d, J=8.2 Hz, 2H), 7.54-7.48 (br s, 1H), 4.83 (s, 2H), 3.00 (br s, 3H), 2.93 (br s, 3H), 0.91 (s, 9H), 0.11 (s, 6H).

Intermediate 44B. 4-(4-(Hydroxymethyl)thiazol-2-yl)-N,N-dimethylbenzamide

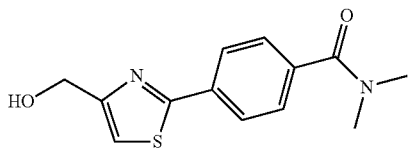 [SMILES: CN(C)C(=O)c1ccc(-c2nc(CO)cs2)cc1]

To a solution of 4-(4-(((tert-butyldimethylsilyl)oxy)methyl)thiazol-2-yl)-N,N-dimethylbenzamide (Intermediate 44A, 3.24 g, 8.60 mmol) in dry THF (150 mL) under nitrogen was added triethylamine trihydofluoride (7.0 mL, 43.0 mmol) dropwise and the mixture was then stirred at room temperature for 18 h. The reaction mixture was quenched by the addition saturated aqueous NaHCO$_3$ and stirring was continued at room temperature for 10 min. The resulting mixture was extracted with DCM (3×250 mL) and the combined organic extract was washed with saturated aqueous NaHCO$_3$ and brine. The organic phase was separated, dried (MgSO$_4$) and evaporated to give the crude product. Flash chromatography (50-100% EtOAc-DCM) afforded the title compound (1.98 g, 88%) as a white solid. LC (Method B): 1.762 min HRMS (ESI): calcd for C$_{13}$H$_{15}$N$_2$O$_2$S [M+H]$^+$ m/z, 263.0849, found 263.0865. $^1$HNMR (400 MHz, CDCl$_3$) δ ppm 7.96 (d, J=7.8 Hz, 2H), 7.49 (d, J=7.8 Hz, 2H), 7.22 (s, 1H), 4.82 (s, 2H), 3.13 (br s, 3H), 3.00 (br s, 3H), 2.66 (br s, 1H).

Intermediate 44C. 4-(4-(Bromomethyl)thiazol-2-yl)-N,N-dimethylbenzamide

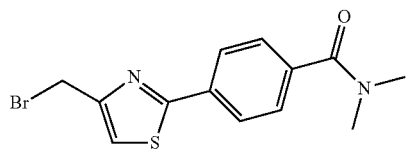 [SMILES: CN(C)C(=O)c1ccc(-c2nc(CBr)cs2)cc1]

To an ice-cold mixture of 4-(4-(hydroxymethyl)thiazol-2-yl)-N,N-dimethylbenzamide (Intermediate 44B, 0.525 g, 2.000 mmol) in DCM (15 mL) under nitrogen was added phosphorous tribromide (0.095 mL, 1.000 mmol) dropwise. After 5 min the cooling bath was removed and the mixture was stirred at room temperature for 3 h. The resulting white suspension was poured into a mixture of ice (50 mL) and saturated aqueous NaHCO$_3$ (50 mL) and extracted with DCM (×2). The combined organic phase was washed (brine), dried (Na$_2$SO$_4$) and evaporated to give a pale yellow gum. Flash chromatography (Isco/50-100% EtOAc-DCM) afforded 4-(4-(bromomethyl)thiazol-2-yl)-N,N-dimethylbenzamide (0.549 g, 84% yield) as a colorless gum which solidified on standing in vacuo. This material was used as such in the next step. LC (Method B): 1.772 min. HRMS (ESI): calcd for C$_{13}$H$_{14}$BrN$_2$OS [M+H]$^+$ m/z 325.0010; found 325.0003. $^1$Hnmr (400 MHz, DMSO-d$_6$) δ ppm 7.98 (d, J=8.6 Hz, 2H), 7.87 (s, 1H), 7.53 (d, J=8.2 Hz, 2H), 4.81 (s, 2H), 2.99 (br s, 3H), 2.92 (br s, 3H).

Example 44: 4-(4-(((5-Methoxy-2-(6-methylimidazo[1,2-b]pyridazin-2-yl)benzo[d]thiazol-7-yl)oxy)methyl)thiazol-2-yl)-N,N-dimethylbenzamide

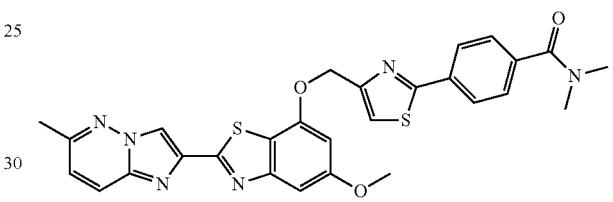

To a solution of 5-methoxy-2-(6-methylimidazo[1,2-b]pyridazin-2-yl)benzo[d]thiazol-7-ol (Intermediate C, 21 mg, 0.067 mmol) in DMF (2 mL) was added 4-(4-(bromomethyl)thiazol-2-yl)-N,N-dimethylbenzamide (Intermediate 44C, 22 mg, 0.067 mmol), followed by potassium carbonate (27.9 mg, 0.202 mmol). The mixture was stirred at 85° C. in a sealed vial for 2.5 h and then the cooled reaction mixture was filtered through Celite and the filtrate was submitted directly to prep HPLC purification in TFA buffered acetonitrile-water. Fractions containing the desired product were concentrated to dryness and the residue was lyophilized from acetonitrile-water to give 4-(4-(((5-methoxy-2-(6-methylimidazo[1,2-b]pyridazin-2-yl)benzo[d]thiazol-7-yl)oxy)methyl)thiazol-2-yl)-N,N-dimethylbenzamide (12 mg, 32% yield) as an amorphous light yellow solid. LC (Method B): 2.229 min HRMS (ESI): calcd for C$_{28}$H$_{25}$N$_6$O$_3$S$_2$ [M+H]$^E$ m/z, 557.1424, found 557.1443. $^1$H NMR (400 MHz, DMSO-d$_6$) δ ppm 8.81 (s, 1H), 8.12 (d, J=9.4 Hz, 1H), 8.02 (m, 2H), 7.92 (m, 2H), 7.54 (m, 2H), 7.27 (d, J=9.4 Hz, 1H), 7.24 (d, J=2.0 Hz, 1H), 6.94 (d, J=2.0 Hz, 1H), 5.49 (s, 2H), 3.88 (s, 3H), 2.96 (m, 6H), 2.56 (s, 3H).

Scheme 10

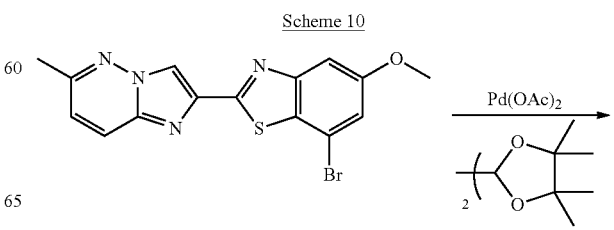

-continued

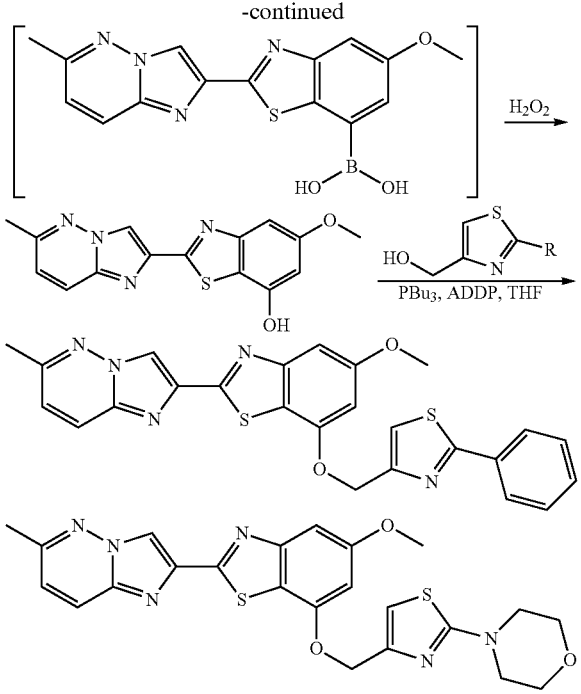

Example 45

5-Methoxy-2-(6-methylimidazo[1,2-b]pyridazin-2-yl)-7-((2-phenylthiazol-4-yl)methoxy)benzo[d]thiazole

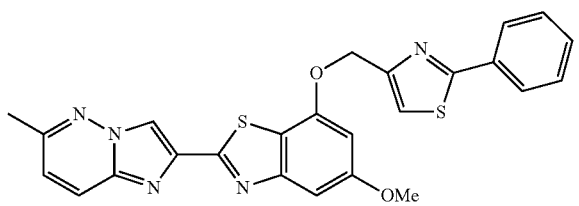 [SMILES: COc1cc(OCc2csc(-c3ccccc3)n2)c2sc(-c3cn4nc(C)ccc4n3)nc2c1]

Intermediate 45A. (5-Methoxy-2-(6-methylimidazo[1,2-b]pyridazin-2-yl)benzo[d]thiazol-7-yl)boronic acid

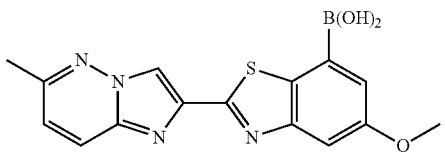

To a stirred solution of 7-bromo-5-methoxy-2-(6-methylimidazo[1,2-b]pyridazin-2-yl)benzo[d]thiazole (Intermediate A, 348 mg, 0.927 mmol) in anhydrous DMF (30 mL) was added 5,5,5',5'-tetramethyl-2,2'-bi(1,3,2-dioxaborinane) (628 mg, 2.78 mmol), potassium acetate (364 mg, 3.71 mmol) and PdCl$_2$(dppf) (68 mg, 0.093 mmol). The reaction mixture was purged with nitrogen for 15 min and then it was heated at 80° C. for 6 h. The cooled reaction mixture was partitioned between dichloromethane-water and the organic phase was separated, washed with brine, dried (MgSO$_4$), filtered and concentrated to dryness to give (5-methoxy-2-(6-methylimidazo[1,2-b]pyridazin-2-yl)benzo[d]thiazol-7-yl)boronic acid (451 mg, 100%) as a white solid which was used directly in the next step.

Intermediate 45B. 5-Methoxy-2-(6-methylimidazo[1,2-b]pyridazin-2-yl)benzo[d]thiazol-7-ol

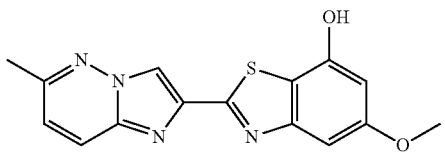

To a stirred solution of (5-methoxy-2-(6-methylimidazo[1,2-b]pyridazin-2-yl)benzo[d]thiazol-7-yl)boronic acid (Intermediate 45A, 485 mg, 0.927 mmol) in anhydrous THF (10 mL) at ambient temperature was added 30% H$_2$O$_2$ (1.05 mL, 9.27 mmol). The reaction mixture was stirred for 3 h and then it was partitioned with dichloromethane-0.5 N HCl. The organic phase was separated, dried (MgSO$_4$), filtered and concentrated to dryness to give a yellow oil. This oil was purified by ISCO using a gradient of 0 to 30% MeOH (containing 1% AcOH)-DCM as eluent to give 5-methoxy-2-(6-methylimidazo[1,2-b]pyridazin-2-yl)benzo[d]thiazol-7-ol (81 mg, 0.26 mmol, 28% yield) as a beige solid. This material was identical with the compound prepared by an alternate method as described for Intermediate C. LC (Method B): 1.929 min. HRMS (ESI): calcd for C$_{15}$H$_{13}$N$_4$O$_2$S [M+H]$^+$ m/z, 313.0754, found 313.0803. $^1$H NMR (400 MHz, DMSO-d$_6$) δ ppm 10.62 (br s, 1H), 8.79 (s, 1H), 8.13 (d, J=9.4 Hz, 1H), 7.27 (d, J=9.4 Hz, 1H), 7.09 (d, J=2.3 Hz, 1H), 6.50 (d, J=2.0 Hz, 1H), 3.81 (s, 3H), 2.56 (s, 3H).

Example 45: 5-Methoxy-2-(6-methylimidazo[1,2-b]pyridazin-2-yl)-7-((2-phenylthiazol-4-yl)methoxy)benzo[d]thiazole

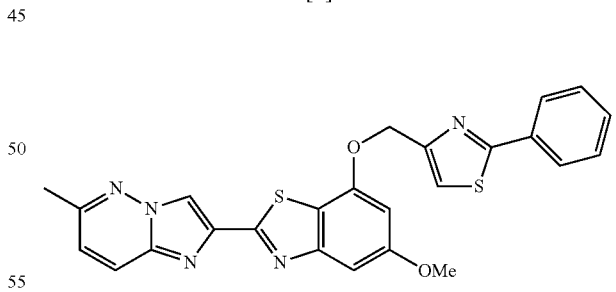

To a solution of 5-methoxy-2-(6-methylimidazo[1,2-b]pyridazin-2-yl)benzo[d]thiazol-7-ol (0.030 g, 0.096 mmol) in DMF (2 mL) in a sealable vial was added 4-(chloromethyl)-2-phenylthiazole (0.022 g, 0.106 mmol), followed by freshly pulverized potassium carbonate (0.040 g, 0.288 mmol). The vial was then sealed and the mixture stirred at 60° C. for 3 h. The cooled reaction mixture was partitioned with dichloromethane-50% saturated aqueous sodium bicarbonate. The organic phase was separated, dried (MgSO$_4$), filtered and concentrated to dryness. The residue was triturated with acetonitrile and the resulting solid was filtered and dried under reduced pressure to give 5-methoxy-2-(6-methylimidazo[1,2-b]pyridazin-2-yl)-7-((2-phenylthiazol-4-yl)methoxy)benzo[d]thiazole (0.029 g, 62% yield) as a light beige solid. LC (Method B): 2.416 min. HRMS (ESI): calcd for $C_{25}H_{20}N_5O_2S_2$ [M+H]$^+$ m/z, 486.1053, found 486.1058. $^1$H NMR (400 MHz, DMSO-d$_6$) δ ppm 8.81 (s, 1H), 8.12 (d, J=9.4 Hz, 1H), 7.97 (m, 2H), 7.88 (s, 1H), 7.55-7.50 (m, 3H), 7.27 (d, J=9.4 Hz, 1H), 7.24 (d, J=2.0 Hz, 1H), 6.94 (d, J=2.0 Hz, 1H), 5.55 (s, 2H), 3.88 (s, 3H), 2.56 (s, 3H).

Example 46: 4-(4-(((5-Methoxy-2-(6-methylimidazo[1,2-b]pyridazin-2-yl)benzo[d]thiazol-7-yl)oxy)methyl)thiazol-2-yl)morpholine

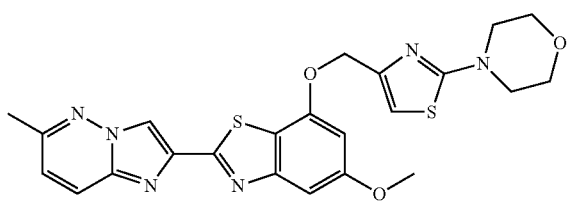 [SMILES: COc1cc(OCc2csc(N3CCOCC3)n2)c2sc(-c3cn4nc(C)ccc4n3)nc2c1]

To a flame-dried 100 mL round-bottomed flask containing 5-methoxy-2-(6-methylimidazo[1,2-b]pyridazin-2-yl)benzo[d]thiazol-7-ol (52 mg, 0.17 mmol) and (2-morpholinothiazol-4-yl)methanol (33.3 mg, 0.166 mmol) in dry THF (5 mL) was added tributylphosphine (0.108 mL, 0.416 mmol). To the resulting solution was added a solution of ADDP (105 mg, 0.416 mmol) in THF (2 mL), dropwise over 30 min. After stirring for another 30 min, the reaction mixture was partitioned with dichloromethane-saturated aqueous sodium bicarbonate. The organic phase was separated, washed with brine, dried (MgSO$_4$), filtered and concentrated to dryness. The residue was triturated with acetonitrile and the solid material was filtered off and dried in vacuo to give 4-(4-(((5-methoxy-2-(6-methylimidazo[1,2-b]pyridazin-2-yl)benzo[d]thiazol-7-yl)oxy)methyl)thiazol-2-yl)morpholine (32 mg, 0.065 mmol, 39% yield) as a beige solid. LC (Method B): 2.118 min. HRMS (ESI): calcd for $C_{23}H_{23}N_6O_3S_2$ [M+H]$^+$ m/z, 495.1268, found 495.1271. $^1$H NMR (400 MHz, DMSO-d$_6$) δ ppm 8.81 (s, 1H), 8.13 (d, J=9.4 Hz, 1H), 7.27 (d, J=9.4 Hz, 1H), 7.22 (d, J=2.0 Hz, 1H), 6.98 (s, 1H), 6.85 (d, J=2.0 Hz, 1H), 5.16 (s, 2H), 3.86 (s, 3H), 3.71 (t, J=4.7 Hz, 4H), 3.38 (t, J=4.7 Hz, 4H), 2.56 (s, 3H).

Scheme 11

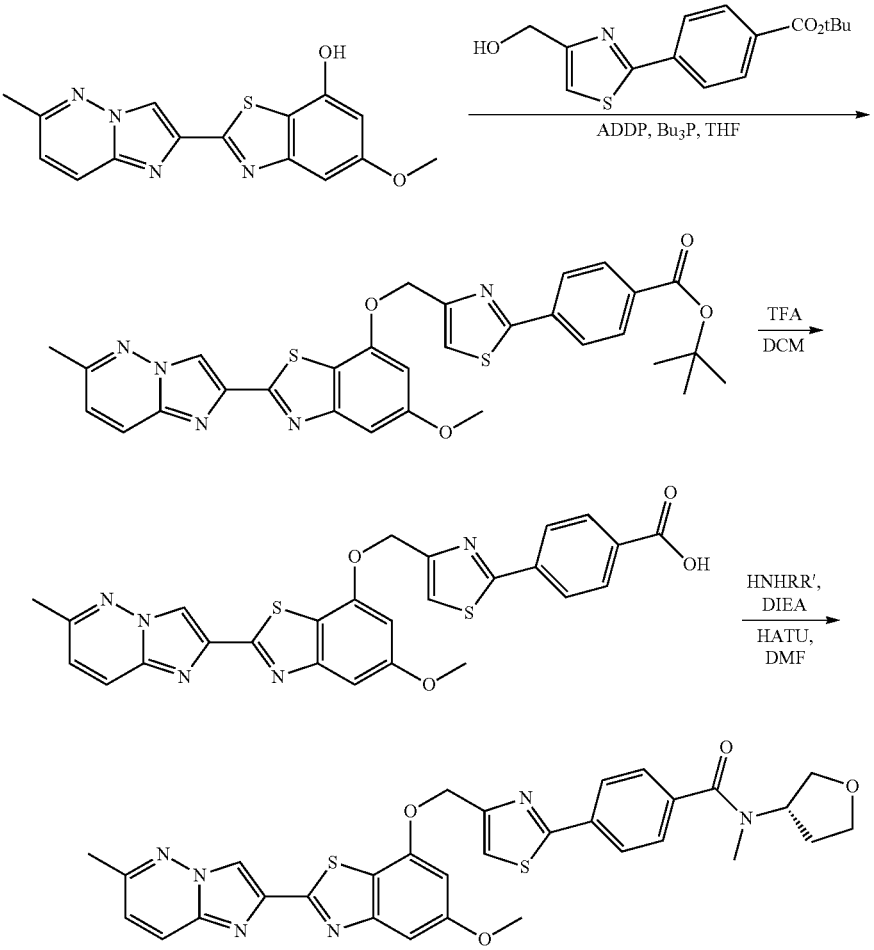

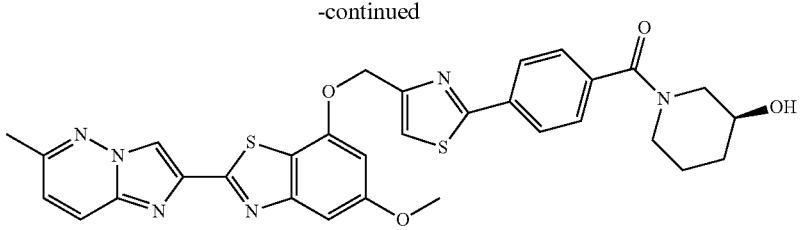

Example 47

(S)-4-(4-(((5-Methoxy-2-(6-methylimidazo[1,2-b]pyridazin-2-yl)benzo[d]thiazol-7-yl)oxy)methyl)thiazol-2-yl)-N-methyl-N-(tetrahydrofuran-3-yl)benzamide

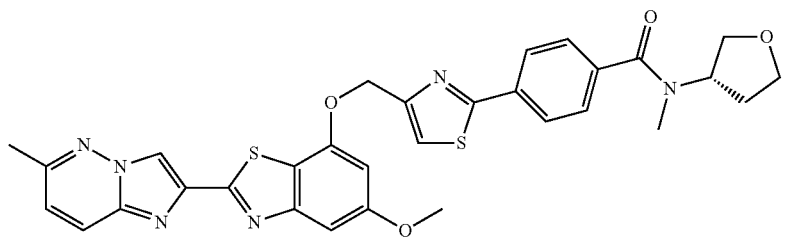 [SMILES: COc1cc(OCc2csc(-c3ccc(C(=O)N(C)[C@H]4CCOC4)cc3)n2)c2sc(-c3cn4nc(C)ccc4n3)nc2c1]

Intermediate 47A. tert-Butyl 4-(4-(((5-methoxy-2-(6-methylimidazo[1,2-b]pyridazin-2-yl)benzo[d]thiazol-7-yl)oxy)methyl)thiazol-2-yl)benzoate

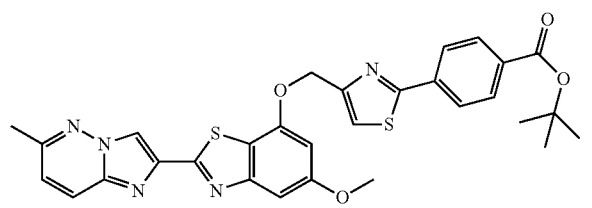 [SMILES: COc1cc(OCc2csc(-c3ccc(C(=O)OC(C)(C)C)cc3)n2)c2sc(-c3cn4nc(C)ccc4n3)nc2c1]

To a flame-dried 100 mL round bottomed flask containing 5-methoxy-2-(6-methylimidazo[1,2-b]pyridazin-2-yl)benzo[d]thiazol-7-ol (Intermediate 45B, 90 mg, 0.29 mmol) and tert-butyl 4-(4-(hydroxymethyl)thiazol-2-yl)benzoate (Intermediate 1J, 84 mg, 0.29 mmol) in dry THF (40 mL) was added tributylphosphine (0.187 ml, 0.720 mmol). To the resulting solution was added a solution of ADDP (182 mg, 0.720 mmol) in THF (10 mL), dropwise over 30 min. After stirring for an additional 30 min, the reaction mixture was partitioned with ethyl acetate-saturated aqueous NaHCO₃. The organic phase was separated, washed with brine, dried (MgSO₄), filtered and concentrated to dryness. The residue was purified by ISCO using a REDISEP® 24 g column (dichloromethane-ethyl acetate) to give the product as a beige solid. This material was triturated with acetonitrile and the resulting suspension was filtered and the filter-cake dried in vacuo to give tert-butyl 4-(4-(4-(((5-methoxy-2-(6-methylimidazo[1,2-b]pyridazin-2-yl)benzo[d]thiazol-7-yl)oxy)methyl)thiazol-2-yl)benzoate (66.0 mg, 0.113 mmol, 39% yield) as a white solid. LC (Method B): 2.613 min. MS (APCI): calcd for $C_{30}H_{28}N_5O_4S_2$ [M+H]⁺ m/z, 586.2, found 586.2. ¹HNMR (400 MHz, DMSO-d₆) δ ppm 8.82 (s, 1H), 8.11 (m, 2H), 8.08 (s, 1H), 8.03 (s, 1H), 7.99 (m, 2H), 7.27 (d, J=9.4 Hz, 1H), 7.25 (d, J=2.0 Hz, 1H), 6.94 (d, J=2.0 Hz, 1H), 5.50 (s, 2H), 3.88 (s, 2H), 2.56 (s, 3H), 1.57 (s, 9H).

Intermediate 47B. 4-(4-(((5-Methoxy-2-(6-methylimidazo[1,2-b]pyridazin-2-yl)benzo[d]thiazol-7-yl)oxy)methyl)thiazol-2-yl)benzoic acid

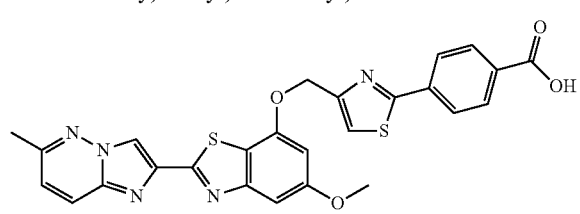

To a stirred solution of tert-butyl 4-(4-(((5-methoxy-2-(6-methylimidazo[1,2-b]pyridazin-2-yl)benzo[d]thiazol-7-yl)oxy)methyl)thiazol-2-yl)benzoate (0.066 g, 0.113 mmol) in dichloromethane (3 mL) was added trifluoroacetic acid (0.500 mL, 6.49 mmol). The reaction mixture was stirred at room temperature for 16 h and then it was concentrated to dryness to give the title compound (0.060 g, 0.113 mmol, 100%) as a white solid which was used as such. LC (Method B): 2.262 min. MS (APCI): calcd for $C_{26}H_{20}N_5O_4S_2$ [M+H]⁺ m/z, 530.1, found 530.1.

Example 47: (S)-4-(4-(((5-Methoxy-2-(6-methylimidazo[1,2-b]pyridazin-2-yl)benzo[d]thiazol-7-yl)oxy)methyl)thiazol-2-yl)-N-methyl-N-(tetrahydrofuran-3-yl)benzamide

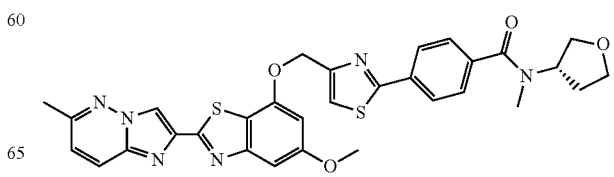

To a stirred solution of 4-(4-(((5-methoxy-2-(6-methyl-imidazo[1,2-b]pyridazin-2-yl)benzo[d]thiazol-7-yl)oxy)methyl)thiazol-2-yl)benzoic acid (0.030 g, 0.057 mmol) in DMF (2 mL) at room temperature was added DIEA (0.049 mL, 0.28 mmol), (S)—N-methyltetrahydrofuran-3-amine hydrochloride (7.8 mg, 0.057 mmol) and HATU (0.021 g, 0.057 mmol). The reaction mixture was stirred for 1 h and then it was submitted directly to prep HPLC in TFA buffered MeOH-water. The product-containing fractions were evaporated and the residue was lyophilized from acetonitrile-water to give (S)-4-(4-(4-(((5-methoxy-2-(6-methylimidazo[1,2-b]pyridazin-2-yl)benzo[d]thiazol-7-yl)oxy)methyl)thiazol-2-yl)-N-methyl-N-(tetrahydrofuran-3-yl)benzamide (0.021 g, 0.034 mmol, 60.7% yield) as an amorphous white solid. LC (Method B): 2.225 min. HRMS (ESI): calcd for $C_{31}H_{29}N_6O_4S_2$ [M+11]$^+$ m/z, 613.1686, found 613.1702. $^1$H NMR (400 MHz, DMSO-d$_6$) δ ppm 8.81 (s, 1H), 8.12 (d, J=9.4 Hz, 1H), 8.03 (d, J=8.2 Hz, 2H), 7.93 (s, 1H), 7.51 (m, 2H), 7.26 (d, J=9.4 Hz, 1H), 7.24 (d, J=2.0 Hz, 1H), 6.94 (d, J=2.0 Hz, 1H), 5.49 (s, 2H), 5.14 (br s, 0.5H), 4.33 (br s, 0.5H), 3.93 (m, 1H), 3.88 (s, 3H), 3.80 (m, 1H), 3.60 (br s, 2H), 2.87 (br s, 3H), 2.56 (s, 3H), 2.14 (br s, 1H), 1.96 (m, 1H).

Example 48: (S)-(3-Hydroxypiperidin-1-yl)(4-(4-(((5-methoxy-2-(6-methylimidazo[1,2-b]pyridazin-2-yl)benzo[d]thiazol-7-yl)oxy)methyl)thiazol-2-yl)phenyl)methanone

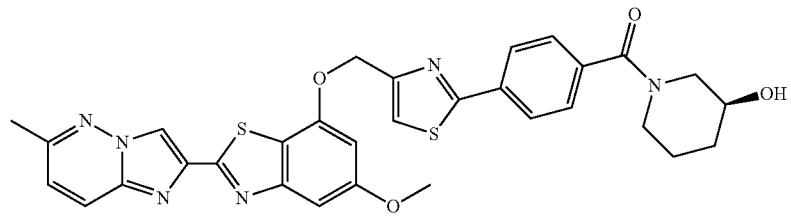 [SMILES: COc1cc(OCc2csc(-c3ccc(C(=O)N4CCC[C@H](O)C4)cc3)n2)c2sc(-c3cn4nc(C)ccc4n3)nc2c1]

The title compound was prepared according to the general method described in Example 47 above. LC (Method B): 1.569 min. HRMS (ESI): calcd for $C_{31}H_{29}N_6O_4S_2$ [M+H]$^+$ m/z, 613.1686, found 613.1789. $^1$H NMR (400 MHz, DMSO-d$_6$) δ ppm 8.81 (s, 1H), 8.12 (d, J=9.8 Hz, 1H), 8.02 (d, J=8.2 Hz, 1H), 7.92 (s, 1H), 7.52 (m, 2H), 7.27 (d, J=9.4 Hz, 1H), 7.24 (d, J=2.0 Hz, 1H), 6.94 (d, J=1.6 Hz, 1H), 5.49 (s, 2H), 4.17 (br s, 0.5H), 3.88 (s, 3H), 3.79 (br s, 1H), 3.28 (br s, 1H), 3.03 (br s, 1H), 2.86 (br s, 0.5H), 2.56 (s, 3H), 1.90-1.59 (m, 2H), 1.42 (m, 2H).

General Procedure for Examples 49-82:

Into a reaction vessel containing amine (0.118 mmol) was added 4-(4-((((5-methoxy-2-(2-methylimidazo[2,1-b][1,3,4]thiadiazol-6-yl)benzo[d]thiazol-7-yl)oxy)methyl)thiazol-2-yl)benzoic acid (18 mg, 0.034 mmol) dissolved in DMF (0.084 M), HATU (25.6 mg, 0.067 mmol) and diisopropylethylamine (29.3 μl, 0.168 mmol). The reaction mixture was stirred at rt for 3 h. Upon complete conversion as monitored by LC-MS, reaction mixture was diluted with DMF (1.6 mL) and the reaction mixture was subjected to reverse-phase HPLC purification to afford the desired product.

Analytical Method A: Column: Supelco Ascentris Express 4.6×50 mm, 237 μm particles; Mobile Phase A: 5:95 acetonitrile:water with 10 mM NH4OAc; Mobile Phase B: 95:5 acetonitrile:water with 10 mM NH4OAc; Gradient: 0-100% B over 4 minutes, 4.0 ml/min; Detection: UV at 220 nm.

Analytical Method C: Column: Supelco Ascentris Express 4.6×50 mm, 2.7 μm particles; Mobile Phase A: 5:95 acetonitrile:water with 0.1% trifluoroacetic acid; Mobile Phase B: 95:5 acetonitrile:water with 0.1% trifluoroacetic acid; Gradient: 0-100% B over 4 minutes, Flow: 4 mL/min; Detection: UV at 220 nm.

TABLE 1

Structures and Analytical data for Examples 49-82:

| Example Number | Structure | MW | HPLC Retention Time (min) | % Purity | Observed MS Ion | Analytical Method |
|---|---|---|---|---|---|---|
| 49 | Chiral | 618.7495 | 1.81 | 98 | 619.3 | C |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 50 | 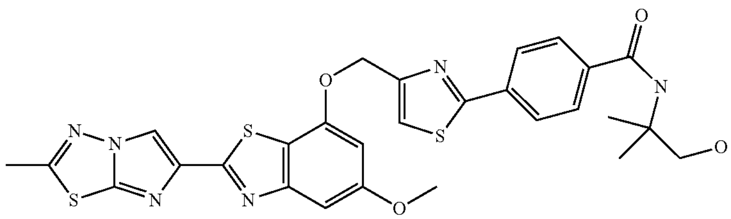 [SMILES: COc1cc(OCc2csc(-c3ccc(C(=O)NC(C)(C)CO)cc3)n2)c2sc(-c3cn4nc(C)sc4n3)nc2c1] | 606.7388 | 1.86 | 98 | 607.2 | C |
| 51 | Chiral | 620.7654 | 1.87 | 99 | 621.2 | C |
| 52 | 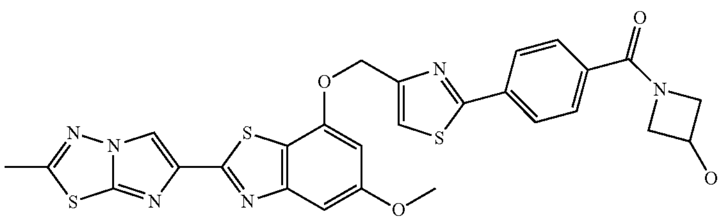 [SMILES: COc1cc(OCc2csc(-c3ccc(C(=O)N4CC(O)C4)cc3)n2)c2sc(-c3cn4nc(C)sc4n3)nc2c1] | 590.6964 | 1.64 | 97 | 591 | C |
| 53 | Chiral | 632.7761 | 1.87 | 99 | 633.3 | C |
| 54 | 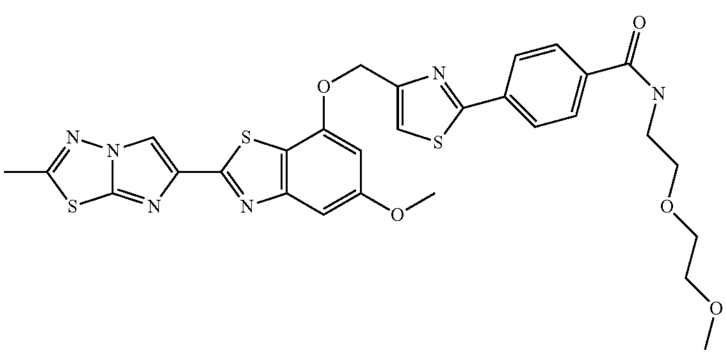 [SMILES: COCCOCCNC(=O)c1ccc(-c2nc(COc3cc(OC)cc4nc(-c5cn6nc(C)sc6n5)sc34)cs2)cc1] | 636.7648 | 1.82 | 97 | 637.2 | C |
| 55 | 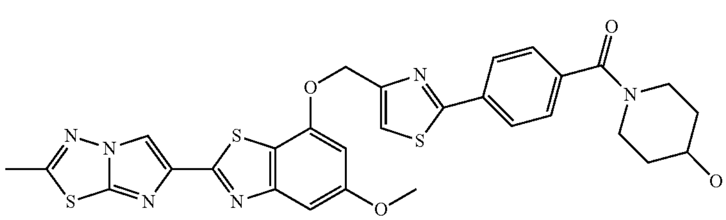 [SMILES: COc1cc(OCc2csc(-c3ccc(C(=O)N4CCC(O)CC4)cc3)n2)c2sc(-c3cn4nc(C)sc4n3)nc2c1] | 618.7495 | 1.68 | 97 | 619.2 | C |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 56 | 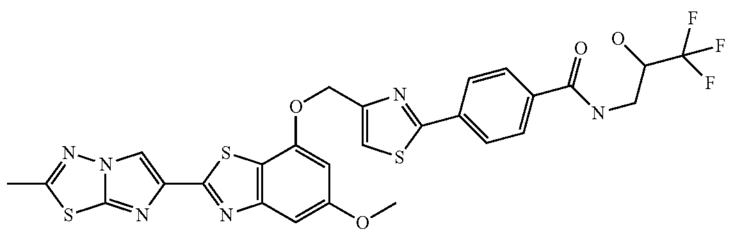 [SMILES: COc1cc(OCc2csc(-c3ccc(C(=O)NCC(O)C(F)(F)F)cc3)n2)c2sc(-c3cn4nc(C)sc4n3)nc2c1] | 646.6836 | 1.9 | 98 | 647.1 | C |
| 57 | 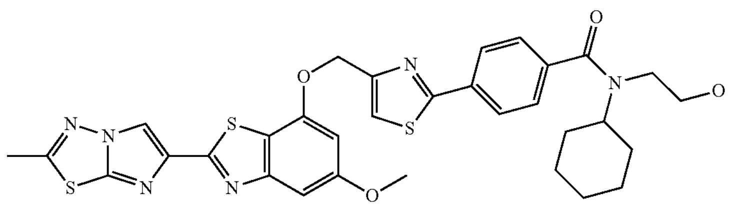 [SMILES: COc1cc(OCc2csc(-c3ccc(C(=O)N(CCO)C4CCCCC4)cc3)n2)c2sc(-c3cn4nc(C)sc4n3)nc2c1] | 660.8293 | 2.11 | 99 | 661.4 | C |
| 58 | 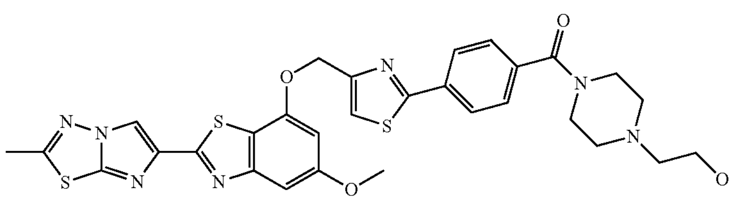 | 647.7908 | 1.62 | 100 | 648.2 | C |
| 59 | 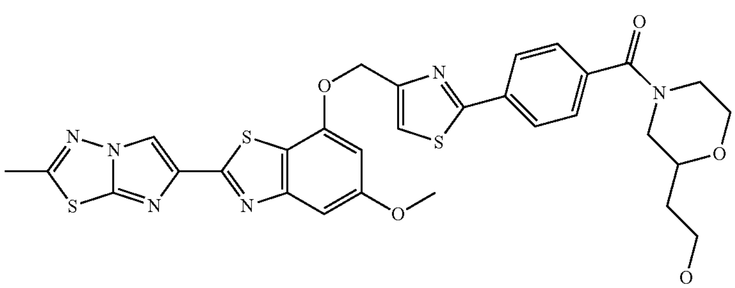 [SMILES: COc1cc(OCc2csc(-c3ccc(C(=O)N4CCOC(CCO)C4)cc3)n2)c2sc(-c3cn4nc(C)sc4n3)nc2c1] | 648.7755 | 1.68 | 97 | 649.1 | C |
| 60 | 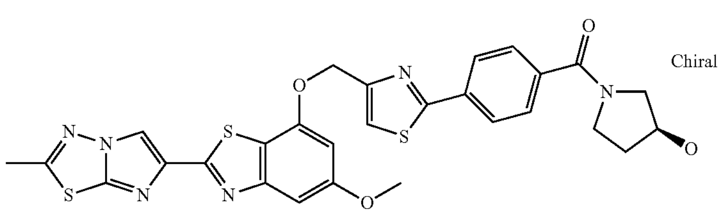 [SMILES: COc1cc(OCc2csc(-c3ccc(C(=O)N4CC[C@H](O)C4)cc3)n2)c2sc(-c3cn4nc(C)sc4n3)nc2c1] | 604.723 | 1.64 | 99 | 605.15 | C |
| 61 | 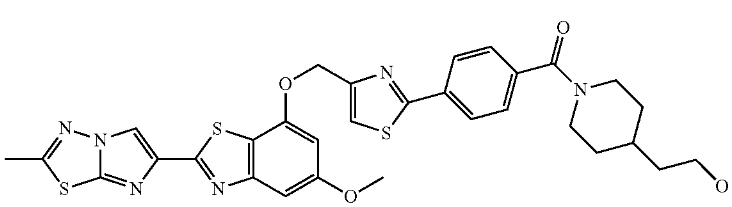 [SMILES: COc1cc(OCc2csc(-c3ccc(C(=O)N4CCC(CCO)CC4)cc3)n2)c2sc(-c3cn4nc(C)sc4n3)nc2c1] | 646.8027 | 1.8 | 98 | 647.17 | C |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 62 | 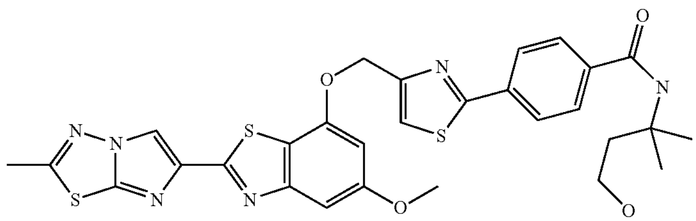 [SMILES: COc1cc(OCc2csc(-c3ccc(C(=O)NC(C)(C)CCO)cc3)n2)c2sc(-c3cn4nc(C)sc4n3)nc2c1] | 620.7654 | 1.9 | 97 | 621.2 | A |
| 63 | 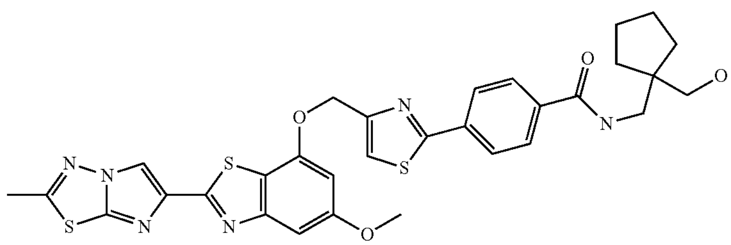 [SMILES: COc1cc(OCc2csc(-c3ccc(C(=O)NCC4(CO)CCCC4)cc3)n2)c2sc(-c3cn4nc(C)sc4n3)nc2c1] | 646.8027 | 2.06 | 100 | 647 | A |
| 64 | 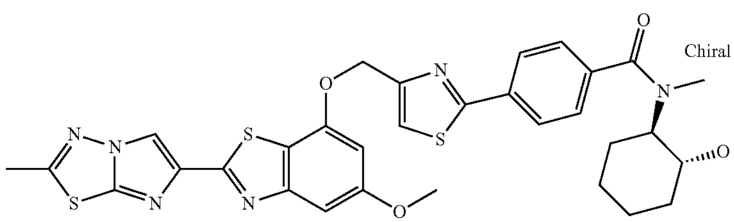 [SMILES: COc1cc(OCc2csc(-c3ccc(C(=O)N(C)[C@@H]4CCCC[C@H]4O)cc3)n2)c2sc(-c3cn4nc(C)sc4n3)nc2c1] | 646.8027 | 1.98 | 99 | 647 | A |
| 65 | 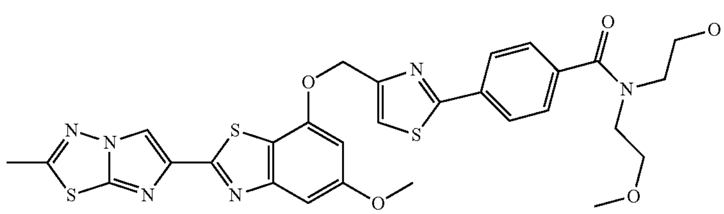 [SMILES: COCCN(CCO)C(=O)c1ccc(-c2nc(COc3cc(OC)cc4nc(-c5cn6nc(C)sc6n5)sc34)cs2)cc1] | 636.7648 | 1.75 | 100 | 637 | A |
| 66 | 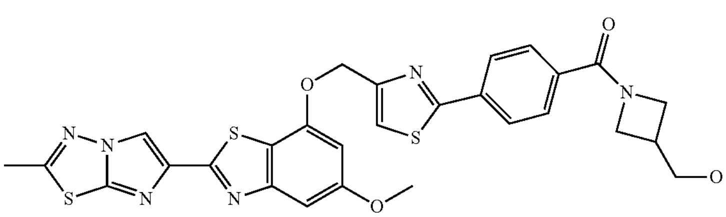 [SMILES: COc1cc(OCc2csc(-c3ccc(C(=O)N4CC(CO)C4)cc3)n2)c2sc(-c3cn4nc(C)sc4n3)nc2c1] | 604.723 | 1.68 | 95 | 605 | A |
| 67 | 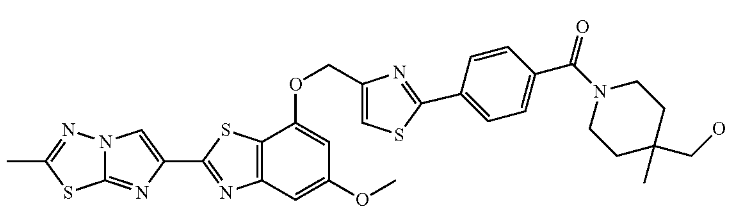 [SMILES: COc1cc(OCc2csc(-c3ccc(C(=O)N4CCC(C)(CO)CC4)cc3)n2)c2sc(-c3cn4nc(C)sc4n3)nc2c1] | 646.8027 | 1.87 | 98 | 647 | A |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 68 | 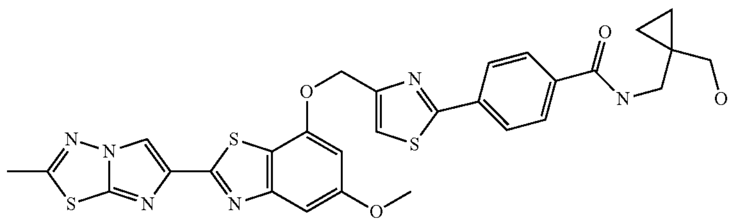 [SMILES: COc1cc(OCc2csc(-c3ccc(C(=O)NCC4(CO)CC4)cc3)n2)c2sc(-c3cn4nc(C)sc4n3)nc2c1] | 618.7495 | 1.84 | 96 | 619.2 | A |
| 69 | 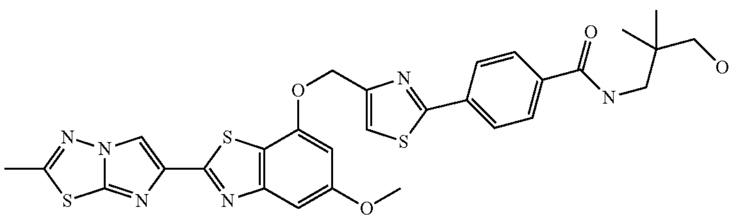 [SMILES: COc1cc(OCc2csc(-c3ccc(C(=O)NCC(C)(C)CO)cc3)n2)c2sc(-c3cn4nc(C)sc4n3)nc2c1] | 620.7654 | 1.92 | 98 | 621 | A |
| 70 | 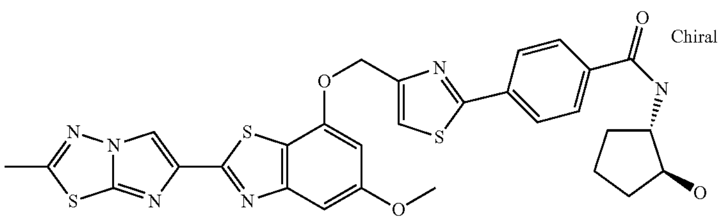 [SMILES: COc1cc(OCc2csc(-c3ccc(C(=O)N[C@H]4CCC[C@@H]4O)cc3)n2)c2sc(-c3cn4nc(C)sc4n3)nc2c1] | 618.7495 | 1.85 | 98 | 619.2 | A |
| 71 | 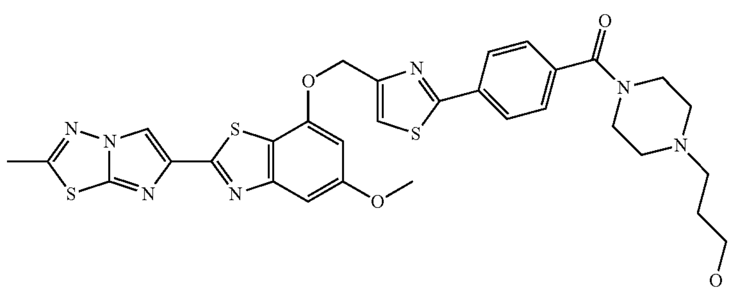 [SMILES: COc1cc(OCc2csc(-c3ccc(C(=O)N4CCN(CCCO)CC4)cc3)n2)c2sc(-c3cn4nc(C)sc4n3)nc2c1] | 661.8173 | 1.66 | 100 | 662 | A |
| 72 | 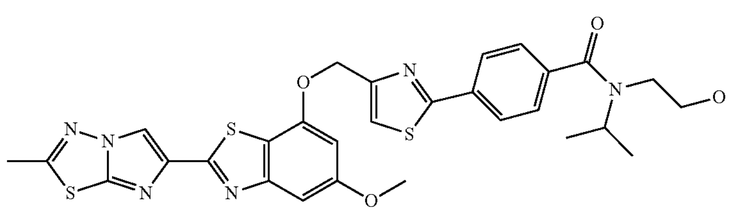 [SMILES: COc1cc(OCc2csc(-c3ccc(C(=O)N(CCO)C(C)C)cc3)n2)c2sc(-c3cn4nc(C)sc4n3)nc2c1] | 620.7654 | 1.92 | 97 | 621.17 | A |
| 73 | 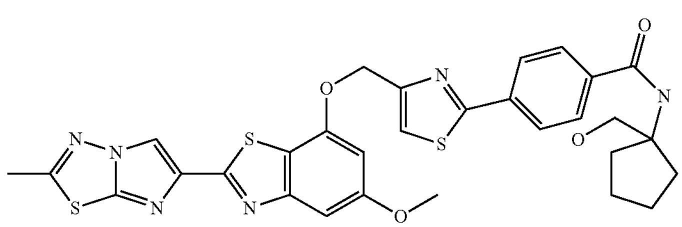 [SMILES: COc1cc(OCc2csc(-c3ccc(C(=O)NC4(CO)CCCC4)cc3)n2)c2sc(-c3cn4nc(C)sc4n3)nc2c1] | 632.7761 | 2.01 | 100 | 633.2 | A |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 74 | 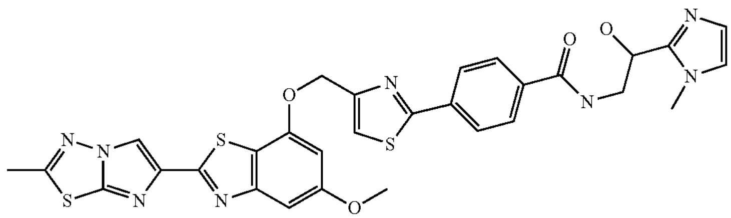 [SMILES: COc1cc(OCc2csc(-c3ccc(C(=O)NCC(O)c4nccn4C)cc3)n2)c2sc(-c3cn4nc(C)sc4n3)nc2c1] | 658.7736 | 1.55 | 99 | 659.1 | C |
| 75 | 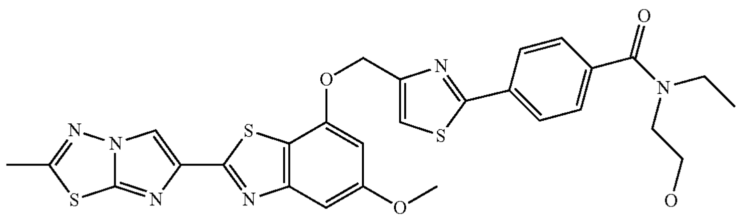 [SMILES: CCN(CCO)C(=O)c1ccc(-c2nc(COc3cc(OC)cc4nc(-c5cn6nc(C)sc6n5)sc34)cs2)cc1] | 606.7388 | 1.79 | 98 | 607.3 | A |
| 76 | 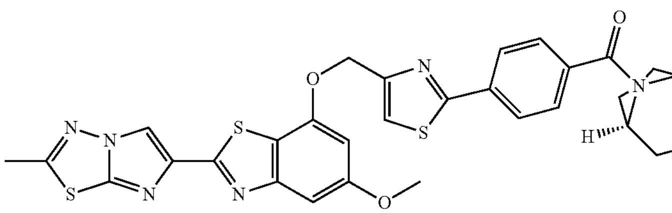 | 644.7868 | 1.85 | 98 | 645.1 | A |
| 77 | 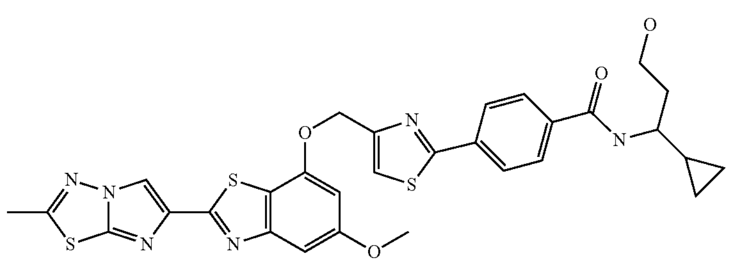 [SMILES: COc1cc(OCc2csc(-c3ccc(C(=O)NC(CCO)C4CC4)cc3)n2)c2sc(-c3cn4nc(C)sc4n3)nc2c1] | 632.7761 | 1.89 | 99 | 633 | A |
| 78 | 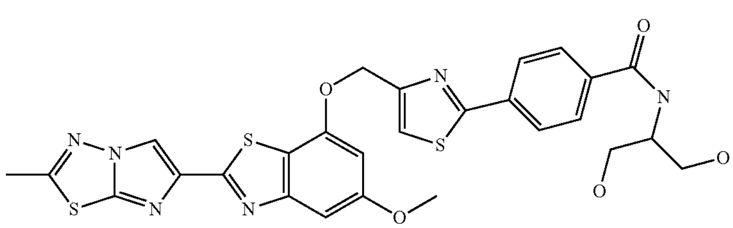 [SMILES: COc1cc(OCc2csc(-c3ccc(C(=O)NC(CO)CO)cc3)n2)c2sc(-c3cn4nc(C)sc4n3)nc2c1] | 608.7117 | 1.59 | 98 | 609.1 | A |
| 79 | 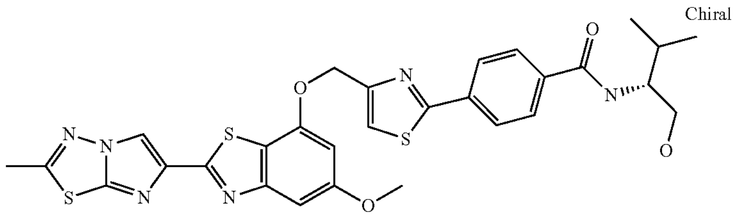 [SMILES: COc1cc(OCc2csc(-c3ccc(C(=O)N[C@@H](CO)C(C)C)cc3)n2)c2sc(-c3cn4nc(C)sc4n3)nc2c1] | 620.7654 | 1.9 | 97 | 621.3 | A |

TABLE 1-continued

Structures and Analytical data for Examples 49-82:

| Example Number | Structure | MW | HPLC Retention Time (min) | % Purity | Observed MS Ion | Analytical Method |
|---|---|---|---|---|---|---|
| 80 | 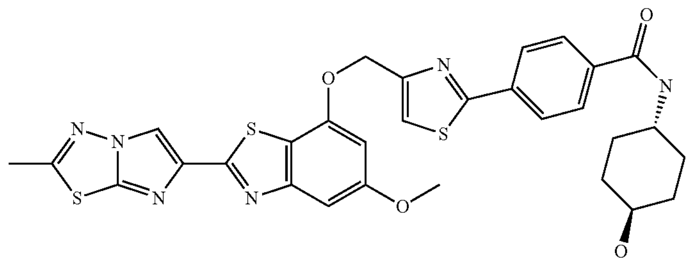 [SMILES: COc1cc(OCc2csc(-c3ccc(C(=O)N[C@H]4CC[C@H](O)CC4)cc3)n2)c2sc(-c3cn4nc(C)sc4n3)nc2c1] | 632.7761 | 1.78 | 100 | 633 | A |
| 81 | 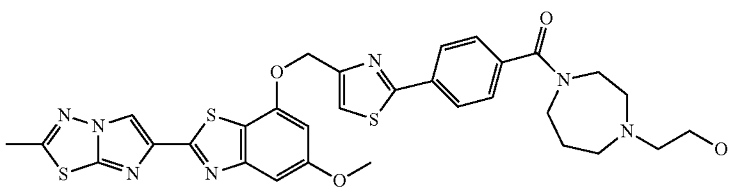 [SMILES: COc1cc(OCc2csc(-c3ccc(C(=O)N4CCCN(CCO)CC4)cc3)n2)c2sc(-c3cn4nc(C)sc4n3)nc2c1] | 661.8173 | 1.59 | 99 | 662 | A |
| 82 | 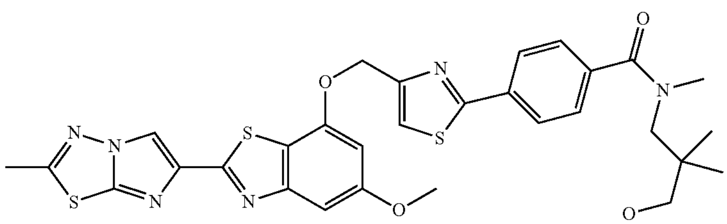 [SMILES: COc1cc(OCc2csc(-c3ccc(C(=O)N(C)CC(C)(C)CO)cc3)n2)c2sc(-c3cn4nc(C)sc4n3)nc2c1] | 634.792 | 2.03 | 100 | 635 | C |

BIOLOGY

The term "PAR4 antagonist" denotes an inhibitor of platelet aggregation which binds PAR4 and inhibits PAR4 cleavage and/or signaling. Typically, PAR4 activity is reduced in a dose dependent manner by at least 10%, 20%, 30%, 40%, 50%, 60%, 70%, 80%, 90%, or 100% compared to such activity in a control cell. The control cell is a cell that has not been treated with the compound. PAR4 activity is determined by any standard method in the art, including those described herein (for example calcium mobilization in PAR4 expressing cells, platelet aggregation, platelet activation assays measuring e.g., calcium mobilization, p-selectin or CD40L release, or thrombosis and hemostasis models). The term "PAR4 antagonist" also includes a compound that inhibits both PAR1 and PAR4.

It is desirable to find compounds with advantageous and improved characteristics compared with known anti-platelet agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; (h) improved therapeutic index with less propensity for bleeding; and (h) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a PAR4 antagonist. Exemplary subjects include human beings of any age with risk factors for cardiovascular disease, or patients that have already experienced one episode of cardiovascular disease. Common risk factors include, but are not limited to, age, male sex, hypertension, smoking or smoking history, elevation of triglycerides, elevation of total cholesterol or LDL cholesterol.

In some embodiments, the subject is a species having a dual PAR1/PAR4 platelet receptor repertoire. As used herein, the term "dual PAR1/PAR4 platelet receptor repertoire" means that a subject expresses PAR1 and PAR4 in platelets or their precursors. Exemplary subjects having a dual PAR1/PAR4 platelet receptor repertoire include human beings, non-human primates, and guinea pigs.

In other embodiments, the subject is a species having a dual PAR3/PAR4 platelet receptor repertoire. As used herein, the term "dual PAR3/PAR4 platelet receptor repertoire" means that a subject expresses PAR3 and PAR4 in platelets or their precursors. Exemplary subjects having a dual PAR3/PAR4 platelet receptor repertoire include rodents and rabbits.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit and/or antagonize PAR4 and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi) within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population. (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005).) Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular weight heparin preparations have been approved by the FDA for these indications.

The term "pharmaceutical composition", as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy*, 20th Edition, Mack Publishing Co., Easton, Pa. (2000).

The invention includes administering to a subject a pharmaceutical composition that includes a compound that binds to PAR4 and inhibits PAR4 cleavage and/or signaling (referred to herein as a "PAR4 antagonist" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the PAR4 antagonist is a biologically active dose. A biologically active dose is a dose that will inhibit cleavage and/or signaling of PAR4 and have an anti-thrombotic effect. Desirably, the PAR4 antagonist has the ability to reduce the activity of PAR4 by at least 5%, 10%, 20%, 30%, 40%, 50%, 60%, 70%, 80%, 90%, 100%, or more than 100% below untreated control levels. The levels of PAR4 in platelets is measured by any method known in the art, including, for example, receptor binding assay, platelet aggregation, platelet activation assays (e.g., p-selectin expression by FACS), Western blot or ELISA analysis using PAR4 cleavage sensitive antibodies. Alternatively, the biological activity of PAR4 is measured by assessing cellular signaling elicited by PAR4 (e.g., calcium mobilization or other second messenger assays).

In some embodiments, a therapeutically effective amount of a PAR4 compound is preferably from about less than 100 mg/kg, 50 mg/kg, 10 mg/kg, 5 mg/kg, 1 mg/kg, or less than 1 mg/kg. In a more preferred embodiment, the therapeutically effective amount of the PAR4 compound is less than 5 mg/kg. In a most preferred embodiment, the therapeutically effective amount of the PAR4 compound is less than 1 mg/kg. Effective doses vary, as recognized by those skilled in the art, depending on route of administration and excipient usage.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, or Formula IA, or Formula IB, or Formula IC, or Formula ID, or Formula IE, or Formula IF, or a compound selected from one of the Examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The activity of the PAR4 antagonists of the present invention can be measured in a variety of in vitro assays. Exemplary assays are shown in the Examples below.

The FLIPR assay is an exemplary in vitro assay for measuring the activity of the PAR4 antagonists of the present invention. In this assay, intracellular calcium mobilization is induced in PAR4 expressing cells by a PAR4 agonist and calcium mobilization is monitored. See, e.g., Example A.

AYPGKF is a known PAR4 agonist. An alternative PAR4 agonist is H-Ala-Phe(4-F)-Pro-Gly-Trp-Leu-Val-Lys-Asn-Gly-NH$_2$. H-Ala-Phe(4-F)-Pro-Gly-Trp-Leu-Val-Lys-Asn-Gly-NH$_2$ has improved agonist activity as compared to AYPGKF with an $EC_{50}$ that is 10 fold lower than the $EC_{50}$ for AYPGKF in the FLIPR assay. H-Ala-Phe(4-F)-Pro-Gly-Trp-Leu-Val-Lys-Asn-Gly-NH$_2$ can be synthesized using methods well known to those of skill in the art.

The FLIPR assay can also be used as a counterscreen to test agonist activity or PAR1 antagonist activity in a cell line that expresses both PAR1 and PAR4. The PAR1 antagonist activity can be tested by the ability of the compound to inhibit calcium mobilization induced by the PAR1 agonist peptide SFLLRN or other PAR1 agonist peptides.

The compounds of the current invention can be tested in vitro for their ability to inhibit platelet aggregation induced by gamma-thrombin as shown in Example B. Gamma-thrombin, a proteolytic product of alpha-thrombin which no longer interacts with PAR1, selectively cleaves and activates PAR4 (Soslau, G. et al., "Unique pathway of thrombin-induced platelet aggregation mediated by glycoprotein Ib", *J. Biol. Chem.*, 276:21173-21183 (2001)). Platelet aggregation can be monitored in a 96-well microplate aggregation assay format or using standard platelet aggregometer. The aggregation assay can also be employed to test the selectivity of the compound for inhibiting platelet aggregation induced by PAR4 agonist peptides, PAR1 agonist peptide, ADP, or thromboxane analogue U46619.

Example C is an alpha-thrombin-induced platelet aggregation assay. Alpha-thrombin activates both PAR1 and PAR4.

Example D is a tissue factor-induced platelet aggregation assay. The conditions in this assay mimic the physiological events during thrombus formation. In this assay, platelet aggregation in human PRP was initiated by the addition of tissue factor and CaCl$_2$. Tissue factor, the initiator of the extrinsic coagulation cascade, is highly elevated in human atherosclerotic plaque. Exposure of blood to tissue factor at the atherosclerotic site triggers a robust generation of thrombin and induces the formation of obstructive thrombi.

The efficacy of the PAR4 antagonists of the present invention in preventing thrombosis can also be measured in a variety of in vivo assays. Exemplary mammals that can provide models of thrombosis and hemostasis to test the effectiveness of the PAR4 antagonists of the present invention as antithrombotic agents include, but are not limited to, guinea pigs and primates. Relevant efficacy models include, but are not limited to, electrolytic injury-induced carotid artery thrombosis, FeCl$_3$-induced carotid artery thrombosis and arteriovenous-shunt thrombosis. Models of kidney bleeding time, renal bleeding time and other bleeding time measurements can be used to assess the bleeding risk of the antithrombotic agents described in the current invention. Example F describes an in vivo model of arterial thrombosis in cynolmolgus monkeys. Compounds of the present invention can be tested in this model for their ability to inhibit thrombus formation induced by electrolytic injury of the carotid artery. Demonstration of efficacy in this model supports the utility of PAR4 antagonists of the present invention for treatment of thromboembolic diseases.

Assays

Materials

1) PAR1 and PAR4 Agonist Peptides

SFFLRR is a known high affinity PAR1 selective agonist peptide. (Reference: Seiler, S. M., "Thrombin receptor antagonists", *Seminars in Thrombosis and Hemostasis*, 22(3):223-232 (1996).) The PAR4 agonist peptides AYPGKF and H-Ala-Phe(4-F)-Pro-Gly-Trp-Leu-Val-Lys-Asn-Gly-NH$_2$ were synthesized. H-Ala-Phe(4-F)-Pro-Gly-Trp-Leu-Val-Lys-Asn-Gly-NH$_2$ showed improved PAR4 agonist activity over AYPGKF in the FLIPR assay ($EC_{50}$ value of 8 µM for H-Ala-Phe(4-F)-Pro-Gly-Trp-Leu-Val-Lys-Asn-Gly-NH$_2$ and 60 µM for AYPGKF) and in washed platelet aggregation assay ($EC_{50}$ value of 0.9 µM for H-Ala-Phe(4-F)-Pro-Gly-Trp-Leu-Val-Lys-Asn-Gly-NH$_2$ and 12 µM for AYPGKF).

2) PAR4 Expressing Cells

HEK293 cells stably expressing PAR4 were generated by a standard method of transfection of human PAR4 (F2R23) cDNA expression vector and selected based on PAR4 protein expression or mRNA expression. Those cells demonstrated functional responses to PAR4 agonist peptide-induced intracellular calcium elevation using FLIPR® (Fluorometric Imaging Plate Reader; Molecular Devices Corp.). These cells also express endogenous PAR1 and can elicit calcium signal upon stimulation with PAR1 agonist peptide. Therefore, the same cells were also used to determine selectivity against PAR1 and agonist activity for both receptors. Cells from HEK293 PAR4 Clone 1.2A (BMS Arctic ID 383940) were propagated and used for calcium mobilization studies.

3) Preparation of Platelet Rich Plasma (PRP)

Human blood was collected in 3.8% sodium citrate at a ratio of 1 ml per 9 ml blood and centrifuged in a Sorvall® RT6000B centrifuge at 900 revolution per minute (rpm) at room temperature (RT) for 15 minutes. PRP was collected and used for aggregation assay. Refludan (Berlex Labs, Wayne, N.J.), a recombinant hirudin, at a final concentration of 1 unit/mL was added to the sample to selectively prevent PAR1 activation induced by residual alpha-thrombin contamination. The remaining blood sample was centrifuged at 2500 rpm at room temperature for 5 minutes to collect platelet-poor plasma (PPP).

4) Preparation of Washed Platelets (WP)

Human blood was collected in ACD (85 mM tri-sodium citrate, 78 mM citric acid, 110 mM D-glucose, pH 4.4) at a ratio of 1.4 ml per 10 ml blood. PRP was isolated by centrifugation at 170 g for 14 minutes and platelets were further pelleted by centrifugation at 1300 g for 6 minutes. Platelets were washed once with 10 ml ACD containing 1 mg/ml bovine serum albumin Platelets were resuspended at ~2.5×10$^8$/ml in Tyrode's Buffer (137 mM NaCl, 2 mM KCl, 1.0 mM MgCl$_2$, 1 mM CaCl$_2$, 5 mM glucose, 20 mM HEPES pH 7.4).

Example A

FLIPR Assay in PAR4-Expressing HEK293 Cells

FLIPR-based calcium mobilization assay in HEK293 cells was used to measure PAR4 antagonism, agonism, and selectivity against PAR1. The activity of the PAR4 antagonists of the present invention were tested in PAR4 expressing cells by monitoring H-Ala-Phe(4-F)-Pro-Gly-Trp-Leu-Val-Lys-Asn-Gly-NH$_2$-induced intracellular calcium mobilization. Counter screens for agonist activity and PAR1 antagonist activity were also performed. Briefly, PAR1/PAR4-expressing HEK293 cells were grown in DMEM (Life Technology, Grand Island, N.Y.) containing 10% heat-inactivated FBS, 1% Penicillin-Streptomycin, 10 μg/mL blasticidin, and 100 μg/mL Zeocin at 37° C. with 5% CO$_2$. Cells were plated overnight prior to the experiment in a black 384-well Purecoat Amine clear bottom plate (Becton Dickinson Biosciences, San Jose, Calif.) at 10,000 cells/well in 30 μL growth medium and incubated in a humidified chamber at 37° C. with 5% CO$_2$ overnight. Prior to compound addition, the cell medium was replaced with 40 μL of 1× calcium and magnesium-containing Hank's Balanced Saline Solution (HBSS) (with 20 mM HEPES) and 1:1000 diluted fluorescent calcium indicator (Codex Biosolutions, Gaithersburg, Md.). After a 30 minute incubation period at 37° C. and a further 30 minute incubation and equilibration period at room temperature, 20 μL test compound (diluted in 1×HBSS buffer) was added at various concentrations at 0.17% dimethyl sulfoxide (DMSO) final concentration. Changes in fluorescence intensity were measured using a Functional Drug Screening System (FDSS, Hamamatsu, Japan) to determine agonist activities. The cells were then incubated for 30 minutes at room temperature followed by addition of 20 μL of agonist peptide for antagonist activity measurement. The PAR4 agonist peptide (H-Ala-Phe(4-F)-Pro-Gly-Trp-Leu-Val-Lys-Asn-Gly-NH$_2$) and the PAR1 agonist peptide (SFFLRR) were routinely tested to ensure a proper response at the EC$_{50}$ value in the assay (~5 μM for PAR4 agonist peptide and ~2 μM for PAR1 agonist peptide). Compound potency was derived from 11-point concentration-response curves.

Example B

Gamma Thrombin Induced Platelet Aggregation Assays

The ability of the compounds of the current invention to inhibit platelet aggregation induced by gamma-thrombin was tested in a 96-well microplate aggregation assay format. Briefly, 90 μL of PRP or washed platelets were pre-incubated for 5 minutes at 37° C. with 3-fold serially diluted test compound, which was prepared as a 100-fold stock solution in dimethyl sulfoxide (DMSO). Aggregation was initiated by addition of 10 μL of gamma-thrombin (Haematologic Technologies, Inc. Essex Junction, Vt.) at 50-100 nM final concentration, which was titrated daily to achieve 80% platelet aggregation. The plate was then placed into a SpectraMax® Plus Plate Reader (Molecular Devices) at 37° C. Platelet aggregation was monitored at a wavelength of 405 nm using a kinetic analysis mode. Prior to the first data collection time point, the plate was shaken for 10 seconds to allow thorough mixing. Data was subsequently collected every 10 seconds for up to 7 minutes total. Data was collected using SoftMax® 5.4.1 software and exported to Microsoft Excel for analysis. The optical density (OD) values at the time point that achieved 75% platelet activation by agonist alone were used for analysis. The OD value from a PRP sample without any treatment served as ODmaximum, and the OD value from a PPP sample containing no platelets served as the ODminimum. Inhibition of platelet aggregation (IPA) was calculated based on the formula: % IPA=(100−100*[ODcompound−ODminimum]/[ODmaximum−ODminimum]). The IC$_{50}$ value of the test compound was calculated by fitting the % IPA values to the one-site concentration response equation: Y=A+(B−A)/{1+(C/X)^13]}, using XLfit for 32 bit Excel® Version 2 Build 30 (ID Business Solutions Limited).

The aggregation assays were also employed to test the selectivity of the compound against other platelet receptors by using SFFLRR for PAR1, collagen (Chrono-Log, Havertown, Pa.) for collagen receptors, ADP for P2Y1 and P2Y12 and U46619 (Cayman Chemical, Ann Arbor, Mich.) for thromboxane receptors.

Example C

Alpha-Thrombin Induced Platelet Aggregation Assays

The ability of PAR4 antagonists to inhibit platelet aggregation induced by alpha-thrombin can be tested using human washed platelets. The antagonists are pre-incubated with washed platelets for 20 min. Aggregation is initiated by addition of 1.5 nM alpha-thrombin (Haematologic Technologies, Essex Junction, Vt.) to 300 μl of washed platelets at stirring speed of 1000 rpm. Platelet aggregation is monitored using an Optical Aggregometer (Chrono-Log, Havertown, Pa.) and the area under the curve (AUC) at 6 min was measured. IC$_{50}$ values are calculated using vehicle control as 0% inhibition.

Example D

Tissue Factor-Induced Platelet Aggregation Assay

The ability of PAR1 or PAR4 antagonists to inhibit platelet aggregation induced by endogenous thrombin can be tested in a tissue factor driven aggregation assay. Aggregation is initiated by addition of CaCl$_2$ and recombinant human tissue factor, which results in the generation of thrombin through activation of the coagulation pathway in the plasma. Anticoagulant agents such as corn trypsin inhibitor (Haematologic Technologies, Essex Junction, Vt.) at 50 μg/ml and PEFABLOC® FG (Centerchem, Norwalk, Conn.) are also added to the sample to prevent fibrin clot formation during the time of the study. Platelet aggregation is monitored using standard instrumentation including optical aggregometer or impedance aggregometer.

Example E

The following table sets out results obtained employing various compounds of the invention tested in the FLIPR assay. As indicated above in Example A, the FLIPR assay, an in vitro assay, measures PAR4 antagonist activity.

TABLE 2

| Example # | PAR4 FLIPR IC50 (μM) |
|---|---|
| 1 | 2.4 |
| 2 | 45 |
| 3 | 3.6 |
| 4 | 4.2 |
| 5 | 1.1 |
| 6 | 3.8 |
| 7 | 30 |
| 8 | 1.8 |
| 9 | 0.33 |
| 10 | 0.98 |
| 11 | 1.4 |
| 12 | 3200 |
| 13 | 800 |
| 14 | 87 |
| 15 | 3.7 |
| 16 | 15 |
| 17 | 2.6 |
| 18 | 5.1 |
| 19 | 81 |
| 20 | 1.2 |
| 21 | 0.92 |
| 22 | 0.76 |
| 23 | 830 |
| 24 | 380 |
| 25 | 2.6 |
| 26 | 9.1 |
| 27 | 1.2 |
| 28 | 3.7 |
| 29 | 80 |
| 30 | 320 |
| 31 | 2.0 |
| 32 | 1.4 |
| 33 | 3.6 |
| 34 | 1.3 |
| 35 | 1.2 |
| 36 | 1.3 |
| 38 | 1.6 |
| 39 | 1.8 |
| 40 | 1.6 |
| 41 | 1.7 |
| 42 | 1.1 |
| 43 | 500 |
| 44 | 2.6 |
| 45 | 1.8 |
| 46 | 2.5 |
| 47 | 6.4 |
| 48 | 9.9 |
| 67 | 0.93 |

Data in Table 2 are reported with two significant figures.

Example F

Cynomolgus Monkey Electrolytic Injury-Induced Carotid Artery Thrombosis Model Healthy cynomolgus monkeys can be used in the study. These monkeys are retired from other pharmacokinetic and pharmacodynamic studies and had at least a 4-week washout period.

On the day of the study, compounds or vehicles are administered orally at 1 to 2 hours before the experiment. Monkeys are then sedated by intramuscular administration of 0.2 mg/kg atropine, 5 mg/kg TELAZOL® (tiletamine/zolazepam) and 0.1 mg/kg hydromorphone to facilitate placement of an endotracheal tube. An intravenous catheter is placed in the left cephalic vein for fluid administration to prevent dehydration. Animals are then administered with an inhalant anesthetic, isoflurane (1-5% to effect) and oxygen, ventilated, and placed on a thermostatically controlled heating pad to maintain the body temperature at 37° C. General anesthesia is maintained at a surgical plane using inhaled isoflurane and oxygen. The left brachial artery is cannulated to record blood pressure and heart rate. Blood pressure and heart rate are monitored to maintain normal vital signs.

The carotid arterial thrombosis model in monkeys is based on a rabbit arterial thrombosis model, as described by Wong et al. (Wong, P. C. et al., "Nonpeptide factor Xa inhibitors: II. Antithrombotic evaluation in a rabbit model of electrically induced carotid artery thrombosis", *J. Pharmacol. Exp. Ther.*, 295:212-218 (2002).) Thrombosis is induced by electrical stimulation of the carotid artery for 5 min at 10 mA using an external stainless-steel bipolar electrode. Carotid blood flow is measured with an appropriately sized TRANSONIC® flow probe and a TRANSONIC® perivascular flowmeter (TS420 Model, Transonic Systems Inc., Ithaca, N.Y.). It is continuously recorded over a 90-min period to monitor thrombosis-induced occlusion. Integrated carotid blood flow is measured by the area under the flow-time curve. It is expressed as percent of total control carotid blood flow, which would result if control blood flow had been maintained continuously for 90 min. In addition, thrombus from the injured artery is removed, blotted twice on a weighing paper to remove residual fluid, and weighed.

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

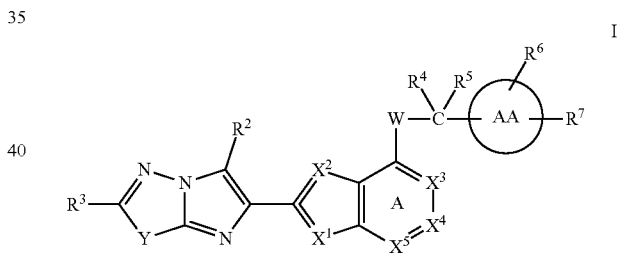

or a stereoisomer, tautomer, or pharmaceutically acceptable salt thereof, wherein:

the dashed lines represent double-bonds with the proviso that only one of the two dashed line double bonds exists at the same time;

$X^2$ is S and $X^1$ is N or $CR^{1a}$; or $X^2$ is O and $X^1$ is N; or $X^2$ is $NR^{1b}$ and $X^1$ is N or $CR^{1a}$; or $X^2$ is N and $X^1$ is $NR^{1b}$; or $X^2$ is $CR^{1a}$ and $X^1$ is $NR^{1b}$;

$X^3$, $X^4$, and $X^5$ are independently selected from $CR^{1d}$ and N;

$R^{1a}$ is selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;

$R^{1b}$ is selected from the group consisting of H, $C_1$-$C_3$ alkyl, and halo-$C_1$-$C_2$alkyl;

$R^{1d}$ is selected from the group consisting of H, $C_1$-$C_4$ alkyl, $C_2$-$C_4$ alkenyl, $C_2$-$C_4$ alkynyl, $C_1$-$C_4$ alkoxy, $C_1$-$C_4$ alkylthio, halo, OH, CN, $OCF_3$, $OCHF_2$, $OCH_2F$, $C_1$-$C_2$-alkoxy-$C_1$-$C_2$-alkoxy, halo-$C_1$-$C_3$-alkyl, halo-$C_{1-2}$-alkoxy, halo-$C_{1-2}$-alkylthio, benzyloxy substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano, and —$(CH_2)_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

Y is S or —$CR^{1e}$=$CR^{1f}$—;

$R^{1e}$ is independently at each occurrence selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;

$R^{1f}$ is independently at each occurrence selected from the group consisting of H, halo, cyano, $C_1$-$C_3$ alkyl, $C_3$-$C_5$ cycloalkyl, halo-$C_1$-$C_2$alkyl, and $C_1$-$C_3$ alkoxy;

$R^2$ is H, halo, $C_1$-$C_4$ alkyl, halo-$C_1$-$C_2$alkyl, $C_1$-$C_4$ alkoxy, CN or $C_3$-$C_5$ cycloalkyl;

$R^3$ is selected from the group consisting of $C_{1-4}$ alkyl, $C_{1-4}$ alkoxy, $C_{1-4}$ alkylthio, $C_{1-2}$ haloalkyl, $C_{1-2}$ haloalkoxy, $C_{1-2}$ haloalkylthio, $C_{3-4}$ cycloalkyl, halo-$C_{3-4}$ cycloalkyl, $C_{1-4}$ alkylamino, di-$C_{1-4}$ alkylamino, ($C_{1-2}$ alkoxy) $C_{1-2}$ alkyl, $C_{2-3}$ alkenyl, $C_{2-3}$ alkynyl, tetrahydrofuran-2-yl, and halo;

W is O or S;

$R^4$ and $R^5$ are independently selected from H, $C_1$-$C_6$ alkyl, $C_1$-$C_4$ fluoroalkyl, and $C_1$-$C_4$ hydroxyalkyl, or $R^4$ and $R^5$ can be taken together with the carbon to which they are attached to form a $C_3$-$C_7$ cycloalkyl ring;

(AA)

is selected from the group consisting of a phenyl ring, a 5-membered heteroaryl ring containing at least one O, N or S atom, or a 6-membered heteroaryl ring containing at least one nitrogen atom; wherein (i) when ring (AA)

is a 5-membered heteroaryl ring, then either
(a) $R^6$ is selected from the group consisting of H, halo, $OCF_3$, $OCHF_2$, OH, CN, $NO_2$, $NR^{11}R^{12}$, COOH, $C_1$-$C_4$ alkoxycarbonyl, (C=O)$NR^{11}R^{12}$, $C_1$-$C_4$ alkylsulfonyl, S(=O)$_2NR^{11}R^{12}$, and $C_1$-$C_5$ alkyl substituted by 0 to 7 groups independently selected from halo, $CF_3$, $OCF_3$, OH, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)-$C_1$-$C_4$-alkyl, di-$C_1$-$C_4$-alkylamino, $C_3$-$C_6$-cycloalkyl, and $C_1$-$C_4$ alkylthio, or
(b) $R^6$ is B—D—, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a linker selected from a single bond, —O—, —S—,

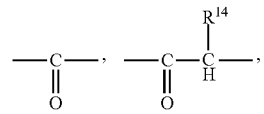

$C_1$-$C_4$ alkylene substituted by 0 to 4 groups independently selected from halo or OH, $C_1$-$C_4$ alkyleneoxy, $C_1$-$C_4$ alkylenethio, $C_1$-$C_4$ alkyleneoxy-$C_1$-$C_4$-alkylene, $C_1$-$C_4$-alkylenethio-$C_1$-$C_4$-alkylene, —S—$C_1$-$C_4$-alkylene, —O—$C_1$-$C_4$-alkylene, —NHC(=O), —C(=O)NH—, $SO_2NH$—, and —$NHSO_2$—, and $C_2$-$C_6$ alkenylene; and (ii) when ring (AA)

is phenyl or 6-membered heteroaryl, then
$R^6$ is B—D, where B is selected from the group consisting of a $C_6$-$C_{10}$ aryl, a 5- to 10-membered heteroaryl, a 4- to 10-membered heterocyclyl containing carbon atoms and 1 to 4 additional heteroatoms selected from N, O, and S, a $C_3$-$C_8$ cycloalkyl which may contain unsaturation, and a $C_5$-$C_{11}$ spirocycloalkyl which may contain unsaturation and optionally containing 1 to 3 heteroatoms selected from O, N or S, all of which may be optionally substituted with one or more $R^b$, $R^c$, $R^d$ and $R^e$; and D is a single bond;

each of $R^b$, $R^c$, $R^d$ and $R^e$, at each occurrence, is independently selected from the group consisting of halo, halo-$C_1$-$C_4$ alkoxy, OH, CN, $NO_2$, =O, $NR^{11}R^{12}$, COOH, $C_1$-$C_4$ alkoxy, $C_1$-$C_4$ alkylthio, $C_1$-$C_4$ alkoxycarbonyl, (C=O)$NR^{11}R^{12}$, $C_1$-$C_4$ alkoxy-$C_1$-$C_4$ alkoxy, $C_1$-$C_4$ alkylsulfonyl, $C_1$-$C_4$ alkylsulfinyl, S(=O)$_2NR^{11}R^{12}$, $N(R^{13})$(C=O)$NR^{11}R^{12}$, $N(R^{13})$(C=O)$OR^{14}$, $SO_2R^{14}$, $N(R^{13})$(C=O)$R^{14}$, $NR^{13}S(O)R^{14}$, $NR^{13}SO_2R^{14}$, O(C=O)$NR^{11}R^{12}$, O(C=O)$OR^{14}$, O(C=O)$R^{14}$, (C=O)$OR^{14}$, $C_3$-$C_6$ cycloalkyl, a 4- to 10-membered heterocyclyloxy; a $C_1$-$C_5$ alkyl substituted by 0 to 7 groups independently selected from halo, $CF_3$, $OCF_3$, OH, CN, hydroxy-$C_1$-$C_4$-alkyl, $C_1$-$C_4$ alkoxy, $C_1$-$C_4$ alkoxy-$C_1$-$C_4$ alkoxy, di-$C_1$-$C_4$-alkylaminophenyl-$C_1$-$C_4$-alkyl, (di-$C_1$-$C_4$-alkoxy-$C_1$-$C_4$-alkyl)$C_1$-$C_4$-alkyl, di-$C_1$-$C_4$-alkylamino, $C_3$-$C_6$-cycloalkyl, phenyl, $C_1$-$C_4$-alkoxyphenyl-$C_1$-$C_4$-alkoxy, 4- to 10-membered heterocyclyloxy, $C_1$-$C_4$-alkylcarbonyloxy and $C_1$-$C_4$ alkylthio; —$(CHR^{13})_n$-5- or 6-membered heteroaryl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$; —$(CHR^{13})_n$-4- to 10-membered-heterocyclyl substituted by 0 to 3 groups independently selected from the group consisting of halo, $C_1$-$C_4$ alkoxy, $C_1$-$C_4$ alkyl, cyclopropyl, $CF_3$, $OCF_3$, and $CF_2CH_3$-, hydroxy-$C_1$-$C_4$-alkyl, halo-$C_1$-$C_4$ alkoxy, di-$C_1$-$C_4$-alkylamino-$C_1$-$C_4$-alkyl, halo-$C_1$-$C_4$ alkyl, $C_1$-$C_4$-alkoxy-$C_1$-$C_4$-alkyl, $C_3$-$C_6$ cycloalkyl-$C_1$-$C_4$-alkylcarbonyl, $C_6$-$C_{10}$ arylcarbonyl, $C_1$-$C_4$-alkylcarbonyloxy-$C_1$-$C_4$-alkyl, and a $C_6$-$C_{10}$ aryl substituted by 0 to 3 groups independently selected from the group consisting of halo, $C_1$-$C_4$ alkoxy, $C_1$-$C_4$ alkyl, cyclopropyl, $C_1$-$C_4$-alkoxycarbonyl, (C=O)$NR^{11}R^{12}$, $CF_3$, $OCF_3$, and $CF_2CH_3$;

R¹¹ and R¹² are independently, at each occurrence, selected from the group consisting of H; $C_1$-$C_4$ alkyl; halo-$C_1$-$C_4$-alkyl; hydroxy-$C_1$-$C_4$-haloalkyl; $C_1$-$C_4$ alkyleneoxy-$C_1$-$C_4$-alkylene; $C_2$-$C_4$ alkenyl; $C_2$-$C_4$ alkynyl; di-$C_1$-$C_4$-alkylamino-$C_1$-$C_4$-alkyl; $C_1$-$C_4$-alkylcarbonylamino-$C_1$-$C_4$-alkyl; di-$C_1$-$C_4$-alkoxy-$C_1$-$C_4$-alkyl; di-$C_1$-$C_4$-alkylaminophenyl; hydroxy-$C_1$-$C_4$-alkyl; cyano-$C_1$-$C_4$-alkyl; $C_1$-$C_4$-alkoxy-$C_1$-$C_4$-alkyl; $C_1$-$C_4$ alkoxycarbonyl-$C_1$-$C_4$-alkyl; $C_1$-$C_4$-alkoxycarbonyl; $C_1$-$C_4$-alkylcarbonyl; phenylcarbonyl; $C_1$-$C_4$-alkoxycarbonylamino-$C_1$-$C_4$-alkylcarbonyl; di-$C_1$-$C_4$-alkylamino-$C_1$-$C_4$-alkylcarbonyl; amino-$C_1$-$C_4$-alkylcarbonyl; 4- to 10-membered-heterocyclyl-carbonyl; —($CR^{14}R^{14}$)$_n$-phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano; —($CHR^{13}$)$_n$-$C_3$-$C_6$-cycloalkyl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl; —($CHR^{13}$)$_n$-4- to 10-membered-heterocyclyl substituted by 0 to 3 groups independently selected from the group consisting of halo, $CF_3$, $OCF_3$, 5- or 6-membered heteroaryl, OH, oxo, hydroxy-$C_1$-$C_4$-alkyl, and $C_1$-$C_4$ alkyl; and —($CHR^{13}$)$_n$-5- to 10-membered-heteroaryl substituted by 0 to 3 groups independently selected from the group consisting of halo, $CF_3$, $OCF_3$, 5- or 6-membered heteroaryl, OH, hydroxy-$C_1$-$C_4$-alkyl, and $C_1$-$C_4$ alkyl; or alternatively, $R^{11}$ and $R^{12}$, when attached to the same nitrogen, can be combined to form a 4- to 10-membered mono- or bicyclic heterocyclic ring containing carbon atoms substituted by 0 to 3 groups independently selected from the group consisting of halo, cyano, $CF_3$, $CHF_2$, $OCF_3$, $OCHF_2$, $OCH_2F$, 5- or 6-membered heteroaryl, OH, oxo, hydroxy-$C_1$-$C_4$-alkyl, $C_1$-$C_4$ alkyl and $C_1$-$C_4$ alkoxy, and 0 to 2 additional heteroatoms selected from N, $NR^{13}$, O and $S(O)_p$;

$R^{13}$ is independently, at each occurrence, selected from the group consisting of H, $C_1$-$C_6$ alkyl and —($CH_2$) phenyl;

$R^{14}$ is independently, at each occurrence, selected from the group consisting of H, $C_1$-$C_6$ alkyl, halo-$C_1$-$C_4$-alkyl, $C_1$-$C_4$-alkoxycarbonylamino, ($C_6$-$C_{10}$ arylcarbonylamino), (a 5- to 10-membered heteroarylcarbonylamino) and —($CH_2$)$_n$ phenyl substituted by 0 to 3 groups independently selected from the group consisting of halo, $C_1$-$C_4$ alkoxy, $C_1$-$C_4$ alkyl, cyclopropyl, $CF_3$, $OCF_3$, 5- or 6-membered heteroaryl, OH, $OCHF_2$, di-$C_1$-$C_4$-alkylamino, and cyano;

$R^7$ is selected from the group consisting of H, halo, hydroxyl, cyano, oxo, $C_1$-$C_4$ alkyl, hydroxy-$C_1$-$C_4$-alkyl, $C_1$-$C_4$-alkoxy-$C_1$-$C_4$-alkyl, halo-$C_1$-$C_4$-alkyl, $C_3$-$C_6$-cycloalkyl, halo-$C_3$-$C_6$-cycloalkyl, $C_1$-$C_4$-alkoxy, and halo-$C_1$-$C_4$-alkoxy; or $R^6$ and $R^7$ can be taken together with the carbons to which they attach to form a 5-7 membered heterocyclyl, heteroaryl, or aryl ring;

n, at each occurrence, is independently selected from 0, 1, 2, 3, 4 or 5; and p, at each occurrence, is selected from 0, 1 and 2.

2. The compound of claim 1, wherein $X^2$ is S and $X^1$ is N or $CR^{1a}$.

3. The compound of claim 1, wherein $X^2$ is S and $X^1$ is N.

4. The compound of claim 1, wherein $X^3$, $X^4$, and $X^5$ are all $CR^{1d}$.

5. The compound of claim 1, wherein $X^3$ and $X^5$ are CH, and $X^4$ is $CR^{1d}$.

6. The compound of claim 1, wherein $X^3$ and $X^5$ are CH and $X^4$ is C—(OMe).

7. The compound of claim 1, wherein Y is S.

8. The compound of claim 1, wherein Y is —(CH═CH)—.

9. The compound of claim 1, wherein W is O, $R^2$ is H and $R^3$ is methyl, ethyl, methoxy, 1,1-difluoroethyl or 1-fluoroethyl.

10. The compound of claim 1, wherein $R^4$ and $R^5$ are both H.

11. The compound of claim 1, wherein ring

is phenyl or a 6-membered heteroaryl ring.

12. The compound of claim 1, wherein ring

is a 5-membered heteroaryl ring.

13. The compound of claim 1, wherein Y is S, W is O, $R^2$ is H, $R^3$ is methyl, ethyl, methoxy, 1,1-difluoroethyl, or 1-fluoroethyl, $R^4$ and $R^5$ are both H, and ring

is phenyl, a 5-membered heteroaryl ring or a 6-membered heteroaryl ring.

14. The compound of claim 1, wherein Y is —(CH═CH)—, W is O, $R^2$ is H, $R^3$ is methyl, ethyl, methoxy, 1,1-difluoroethyl, or 1-fluoroethyl, $R^4$ and $R^5$ are both H, and

is phenyl, a 5-membered heteroaryl ring or a 6-membered heteroaryl ring.

15. The compound of claim 1, wherein

is thiazolyl, $R^6$ is phenyl or morpholino, $R^7$ is H or methyl, $R^6$ is optionally substituted with one or more $R^b$, $R^c$, $R^d$ and $R^e$.

16. The compound of claim 1, wherein the compound is selected from the following:

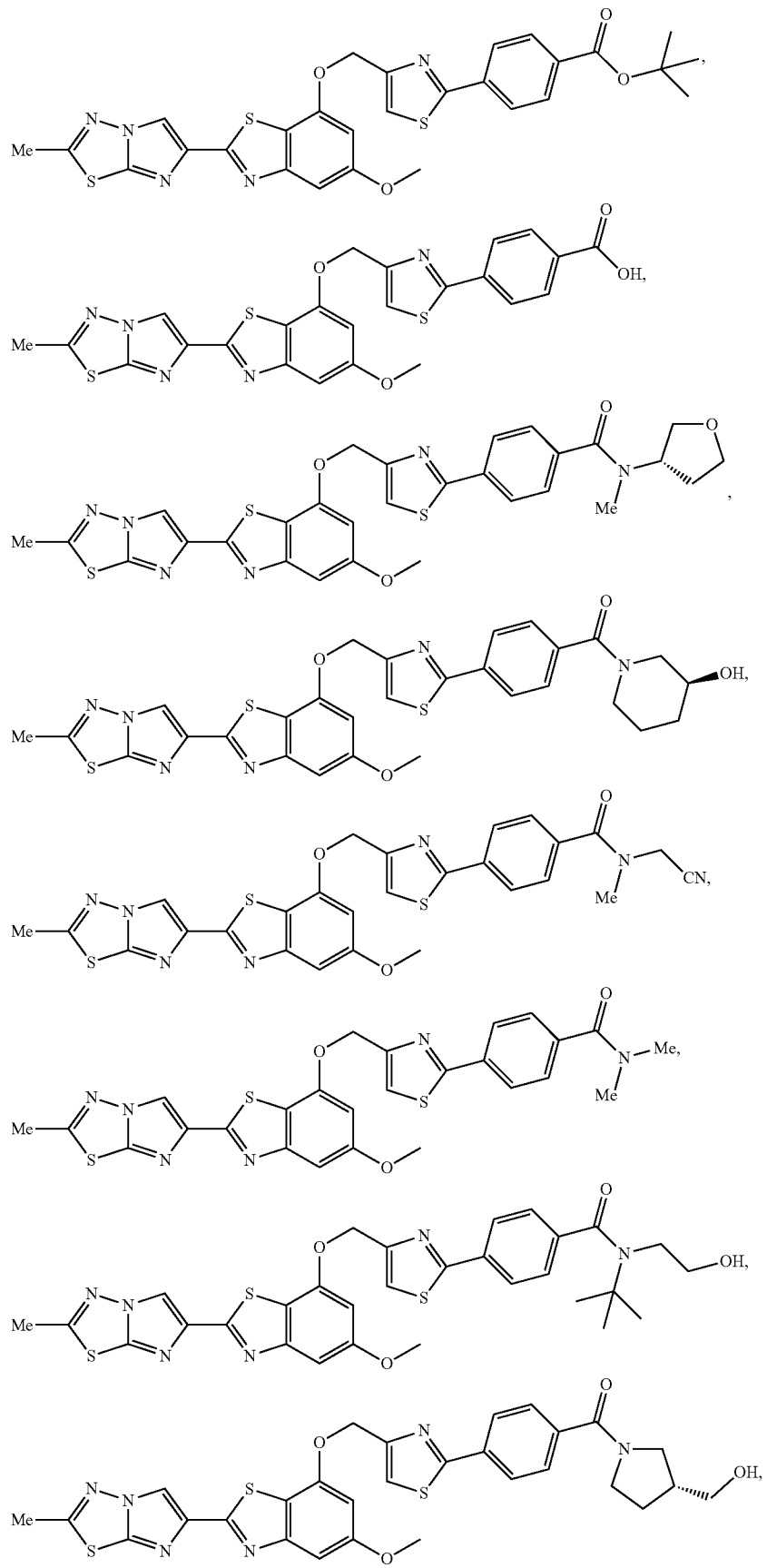

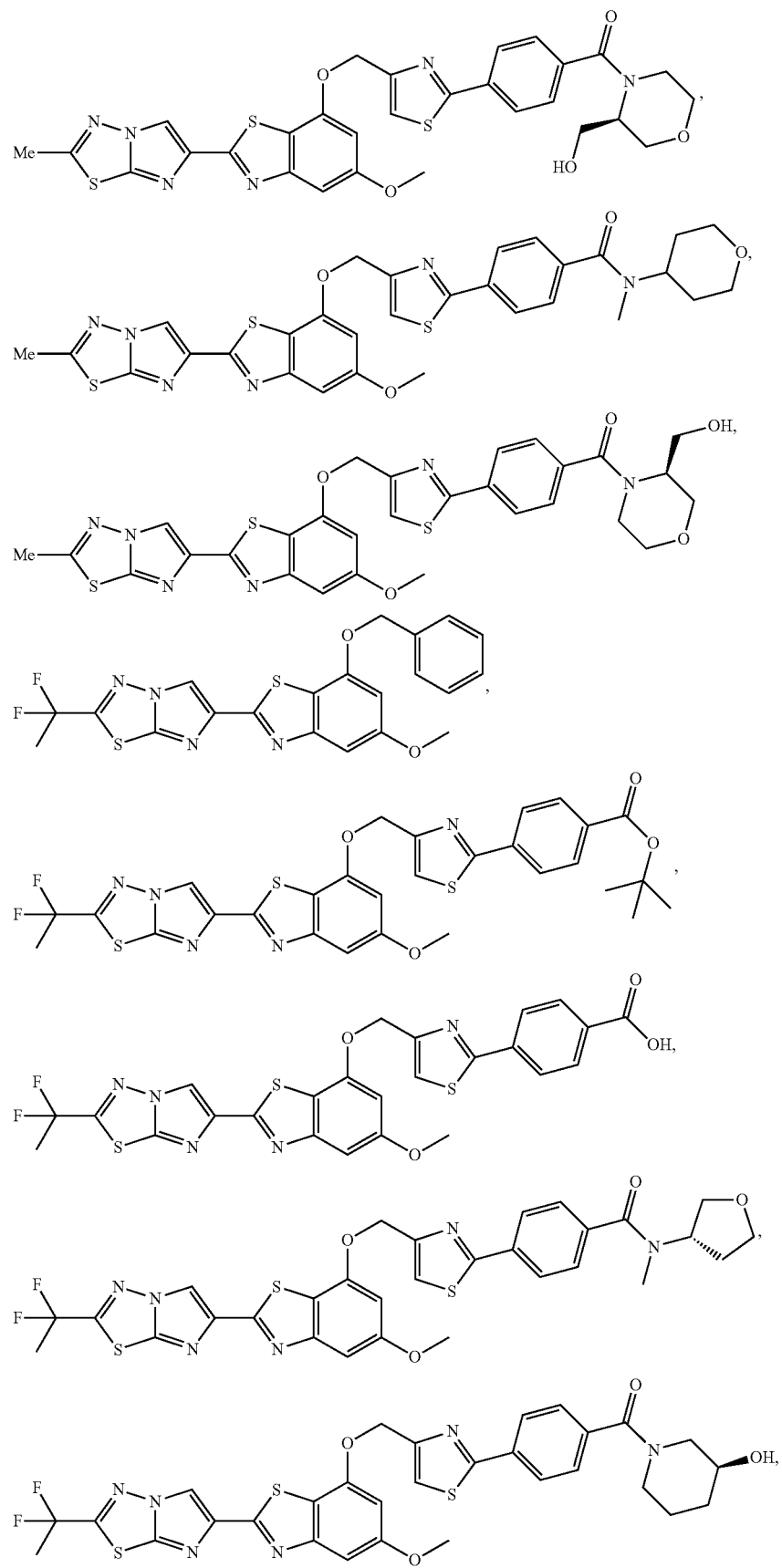

-continued
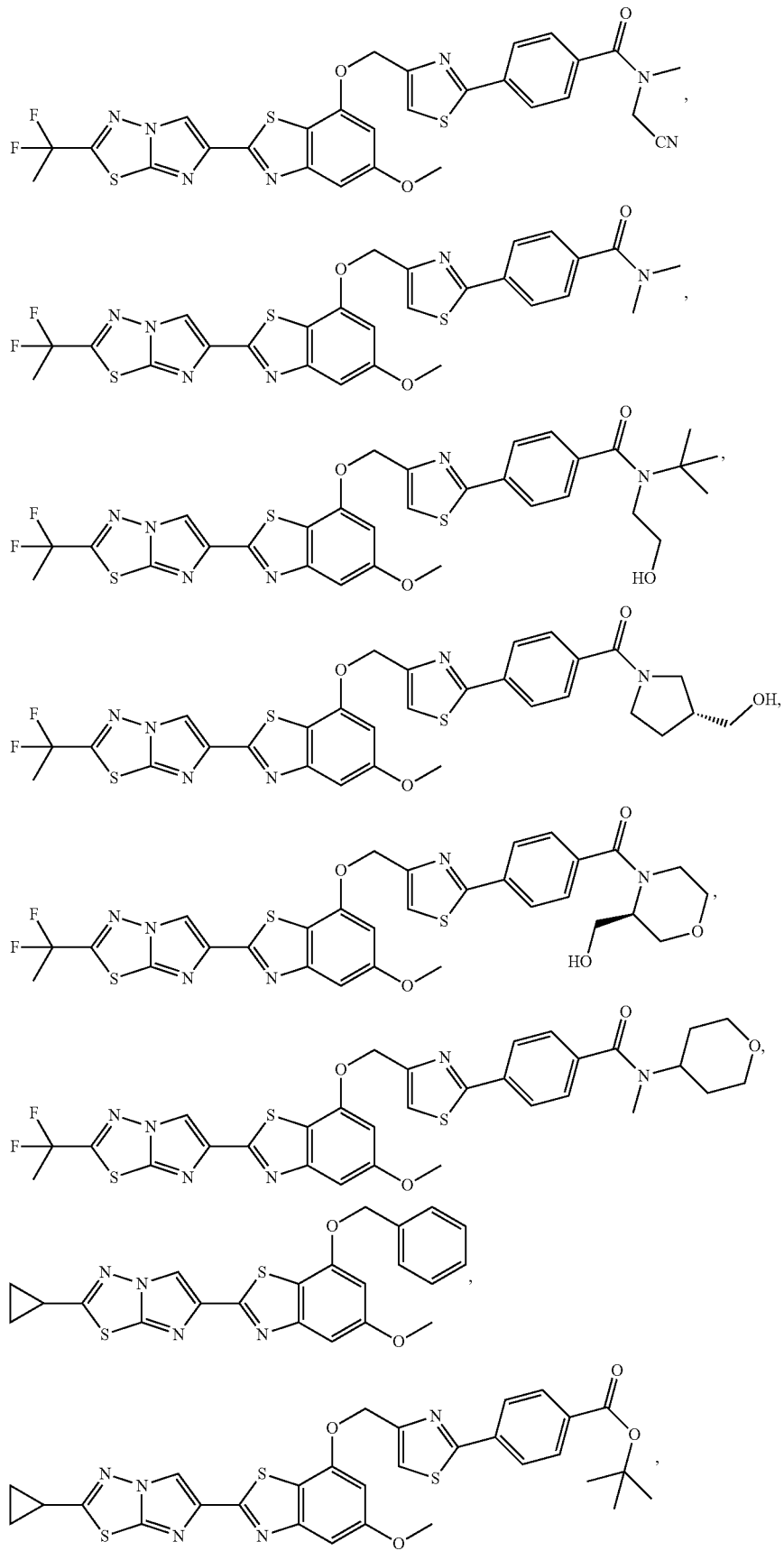

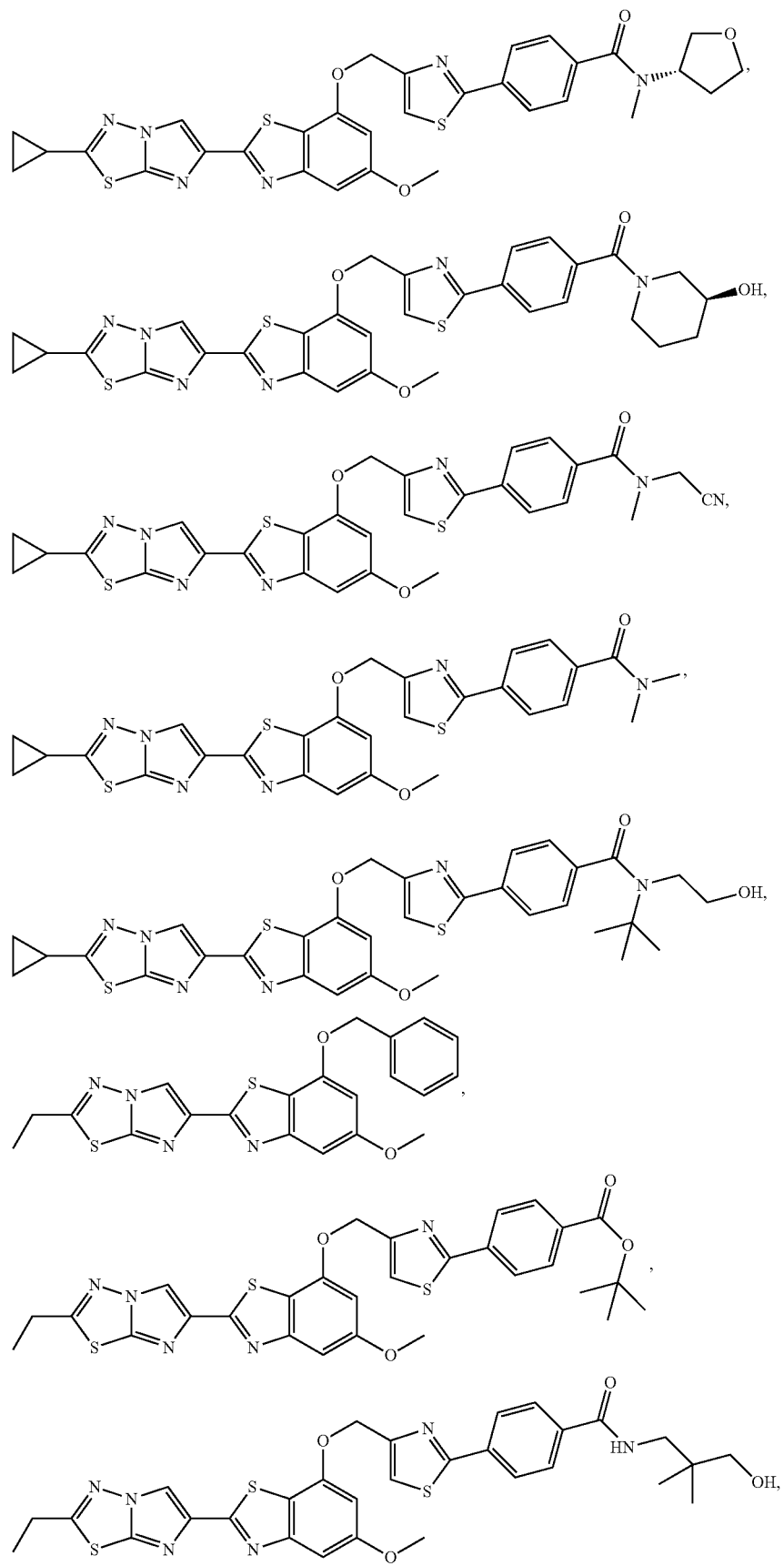

-continued
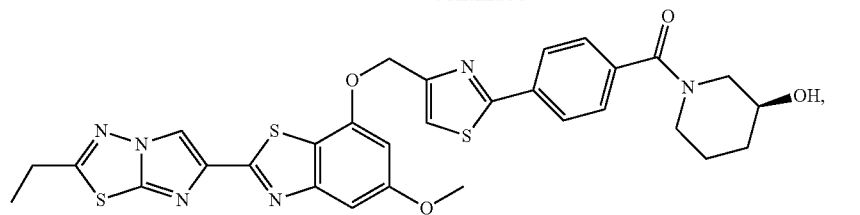
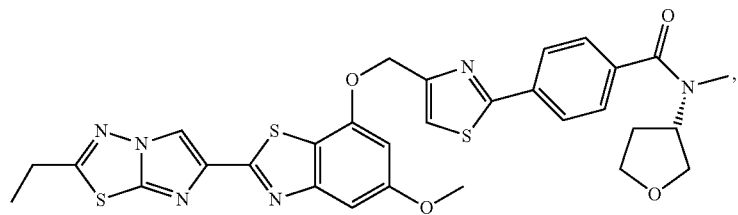
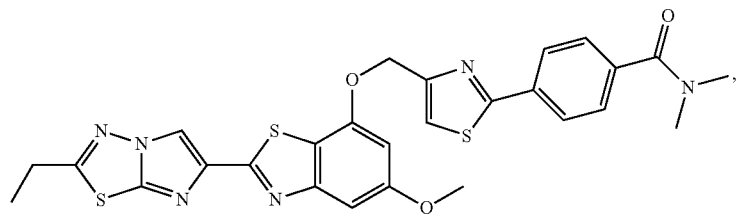
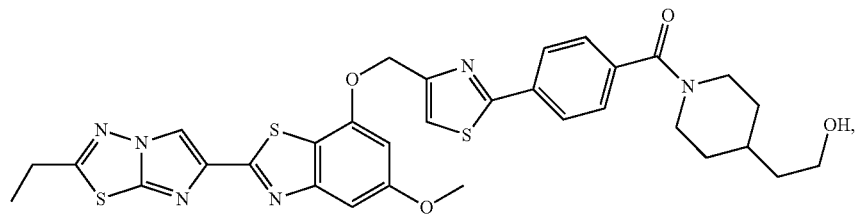
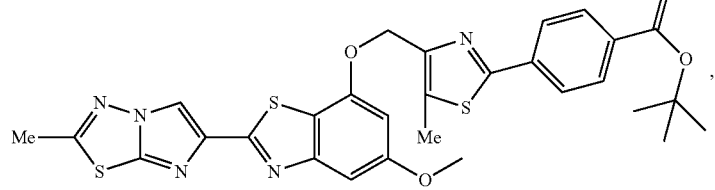
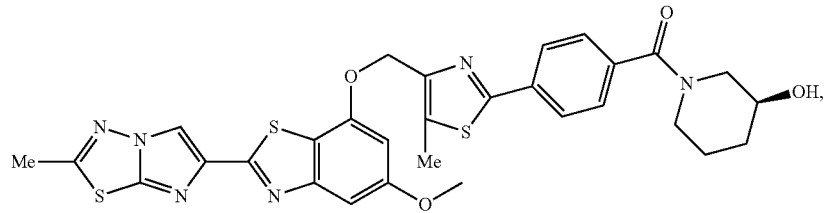
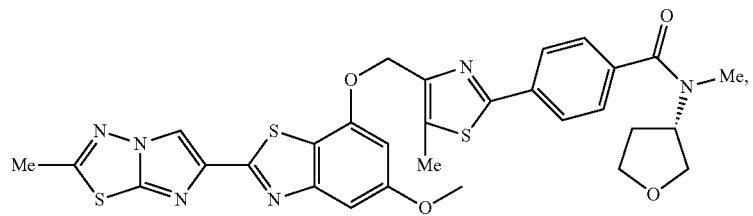
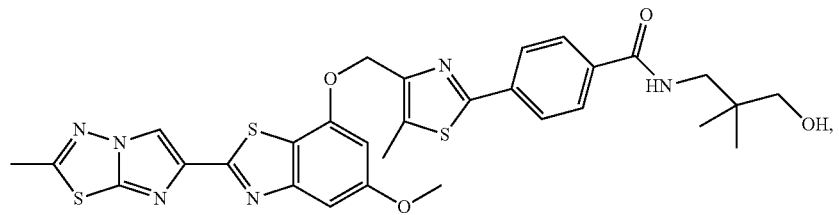
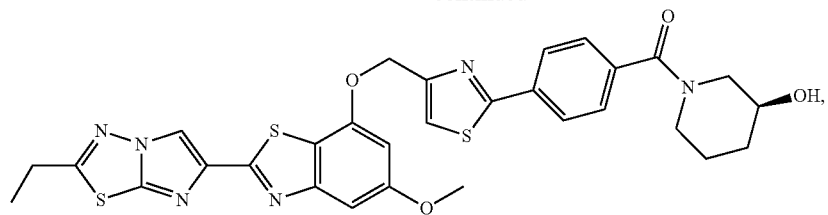
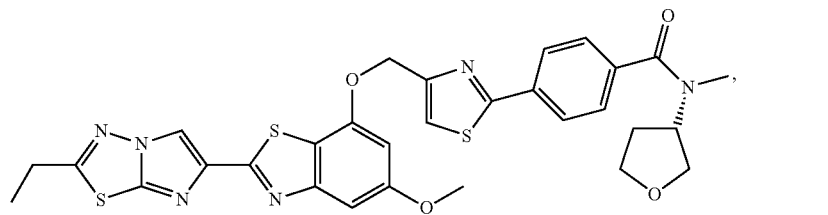
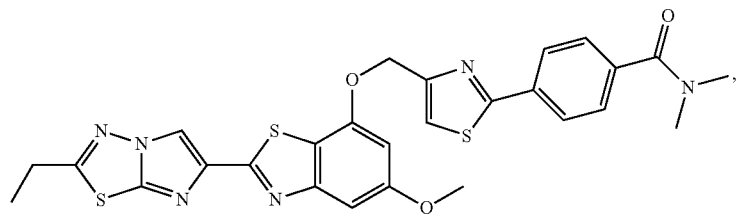
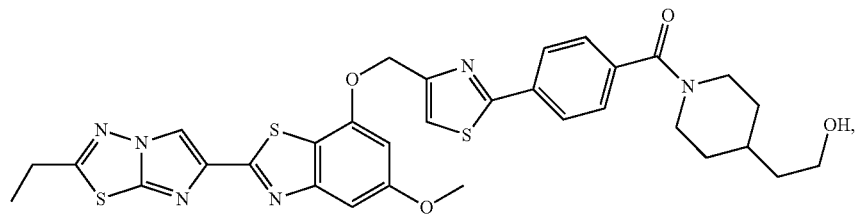
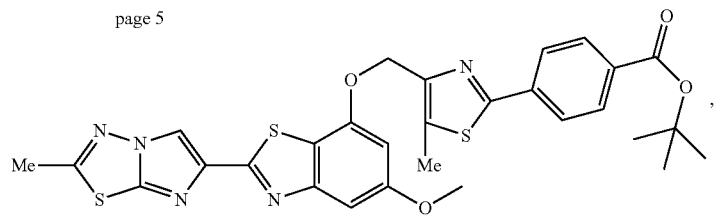
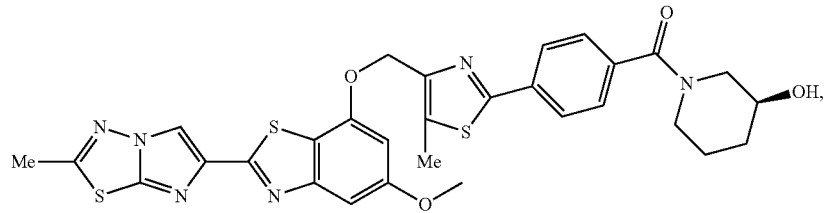
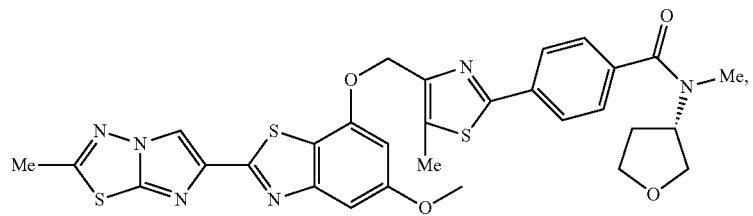
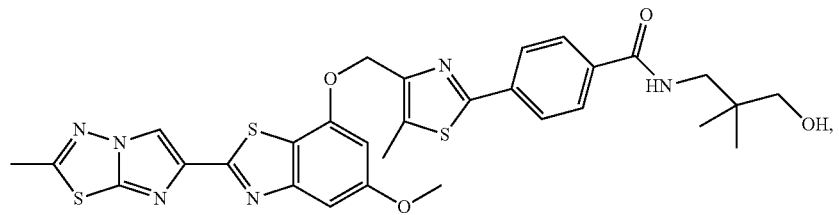

-continued
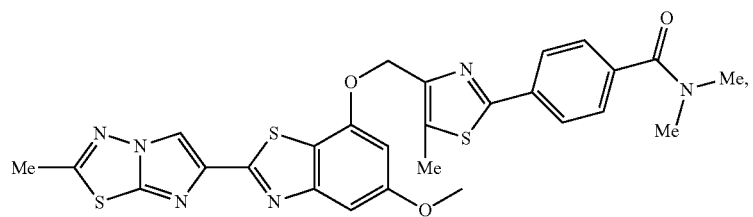
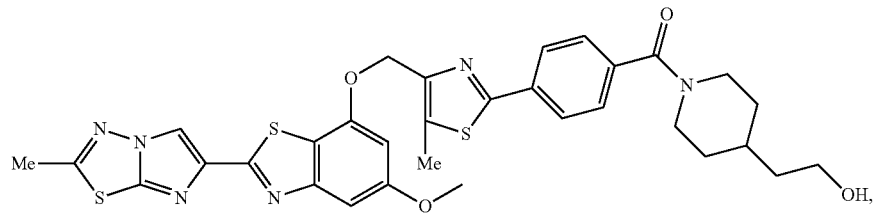
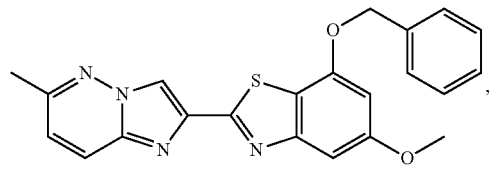
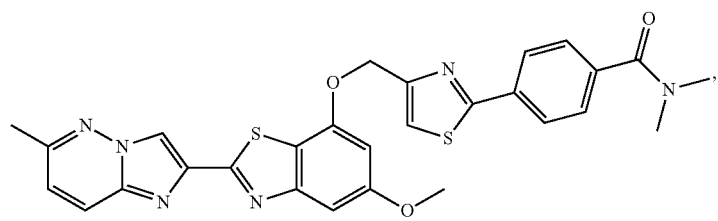
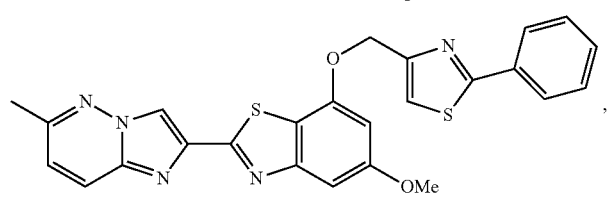
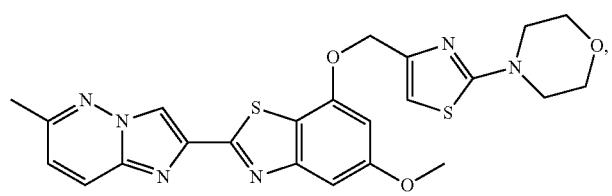
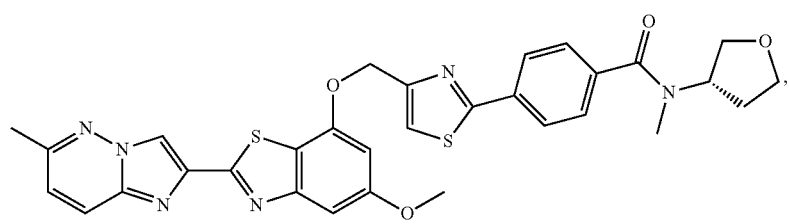
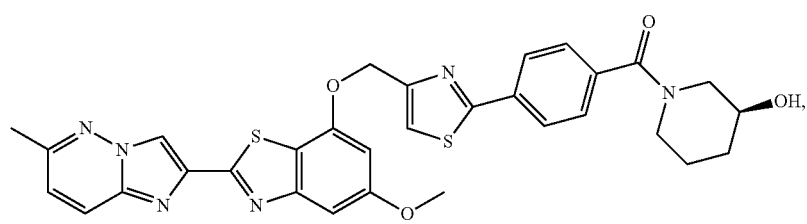

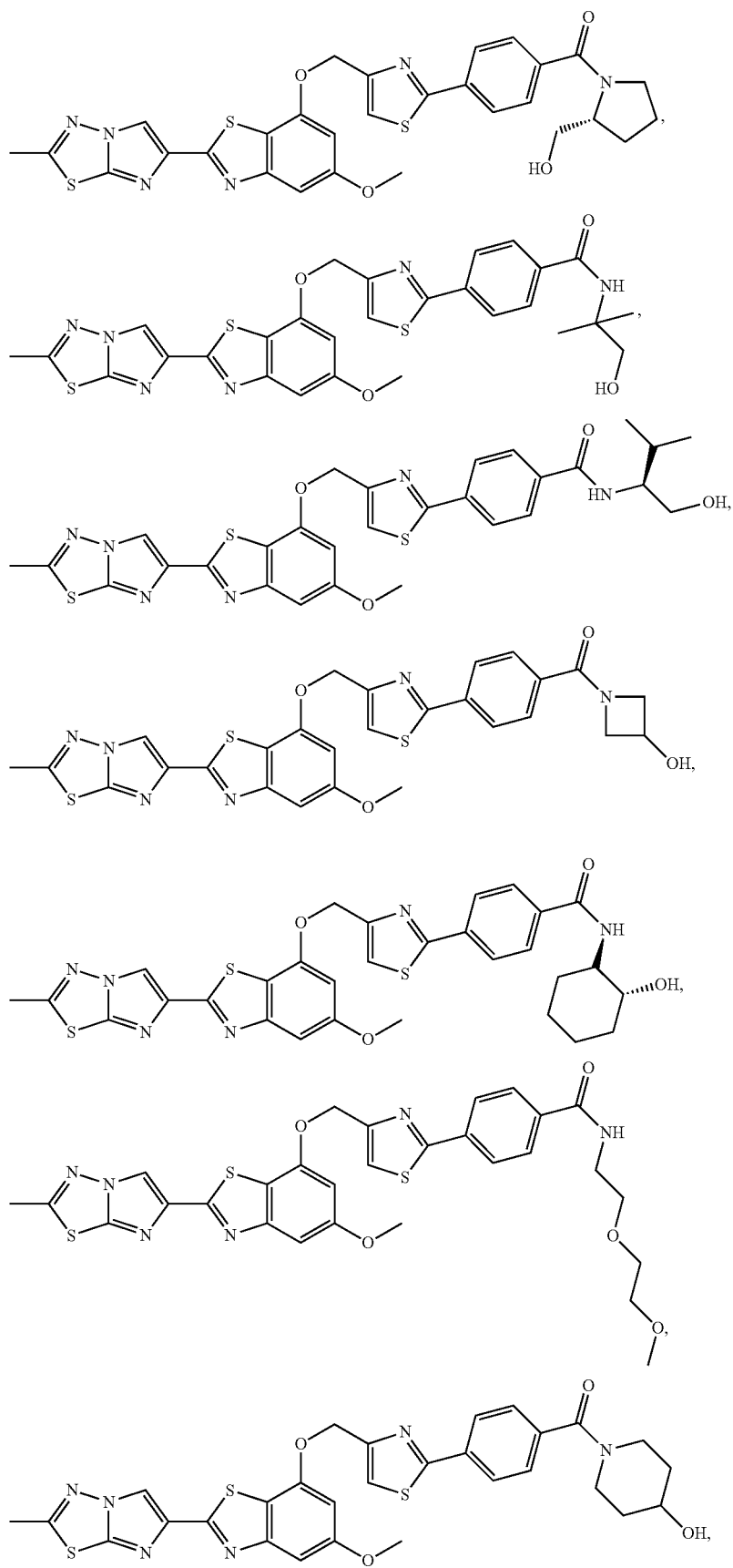

-continued
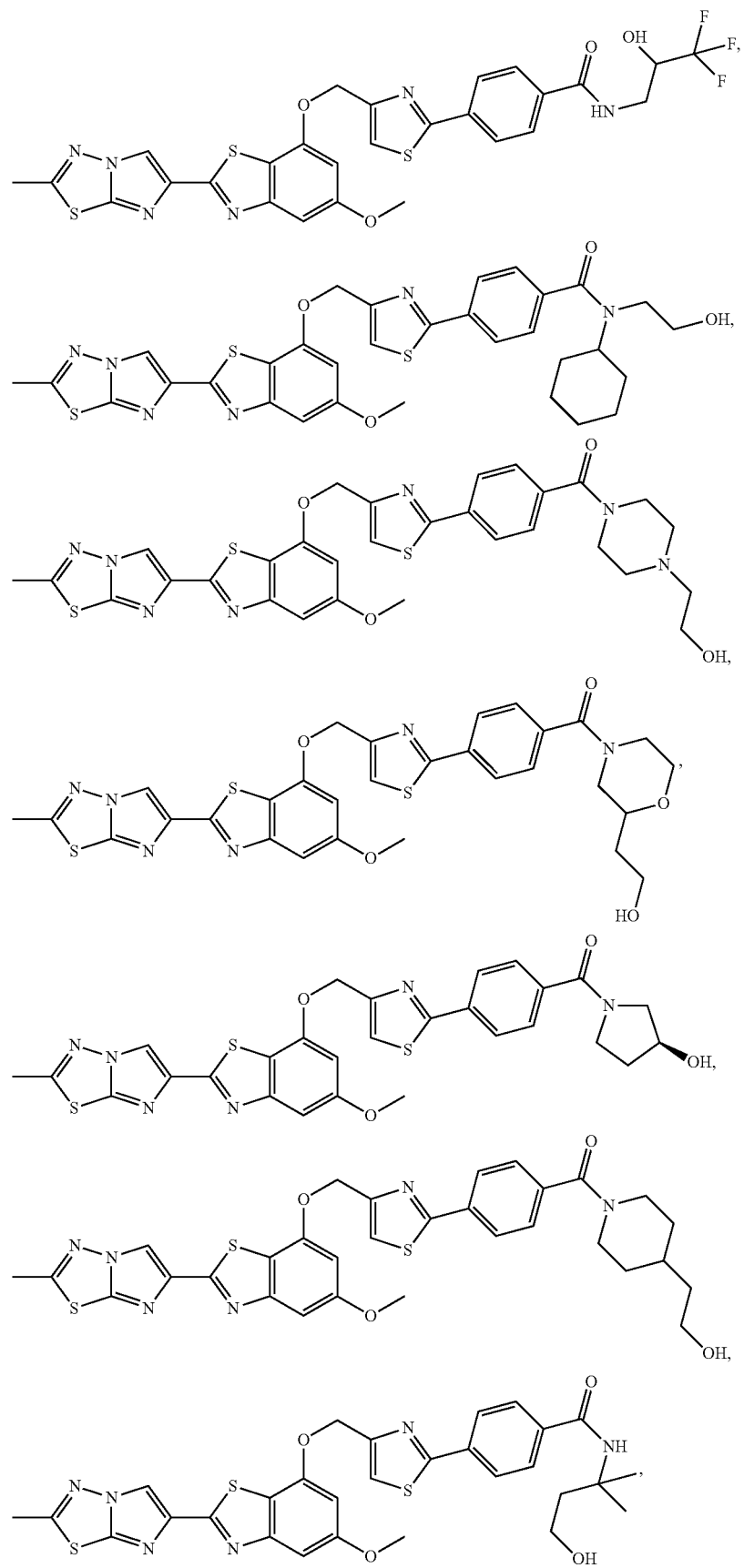

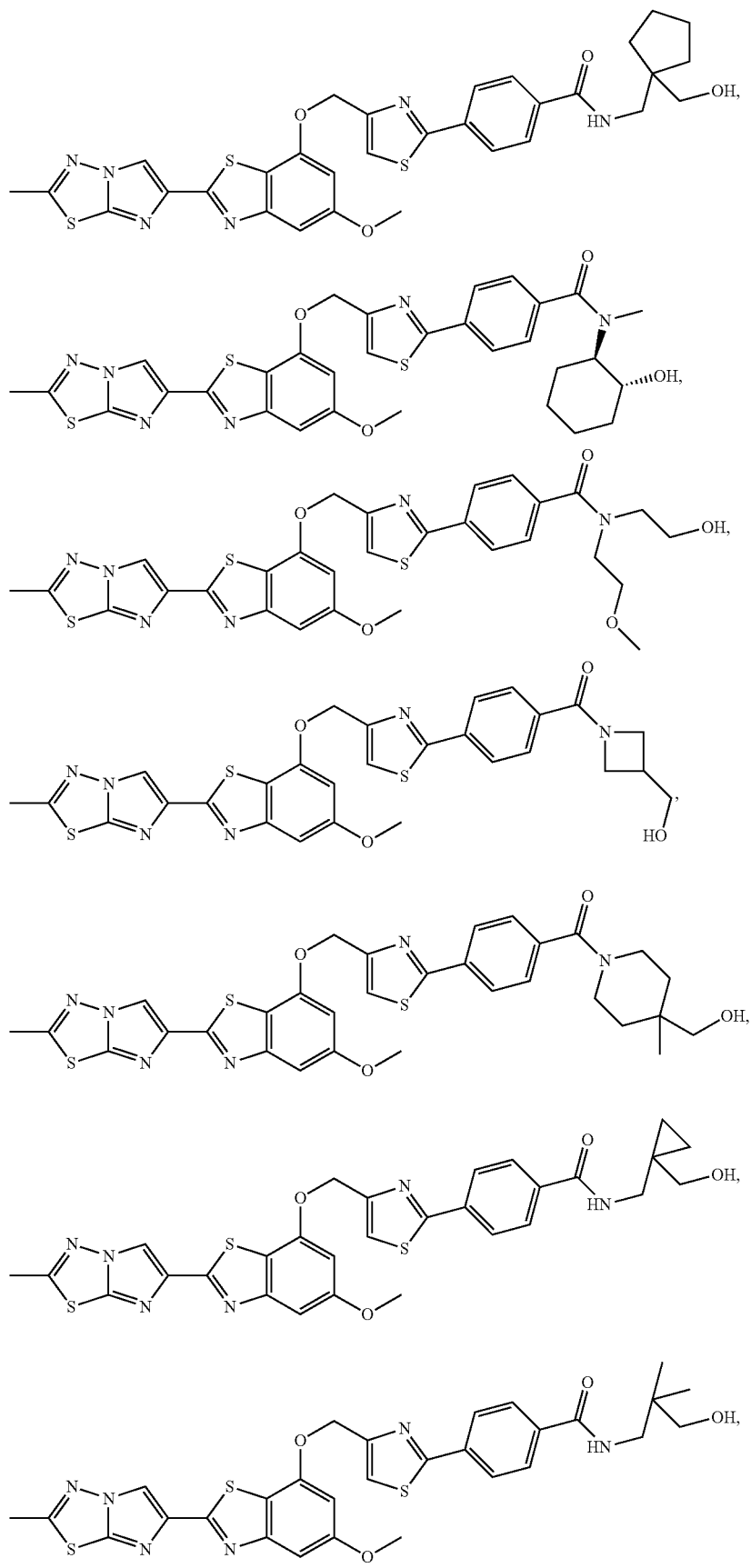

-continued
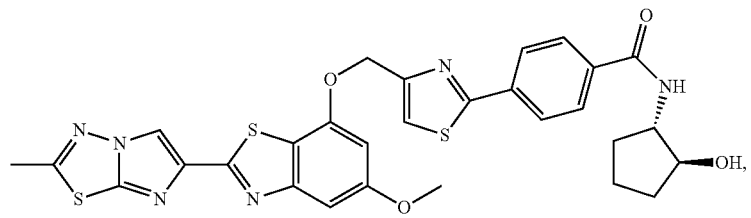
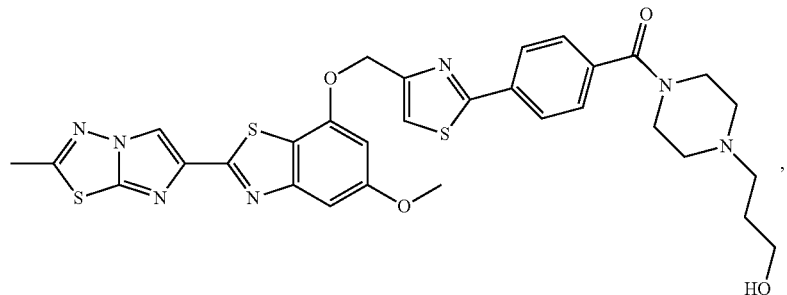
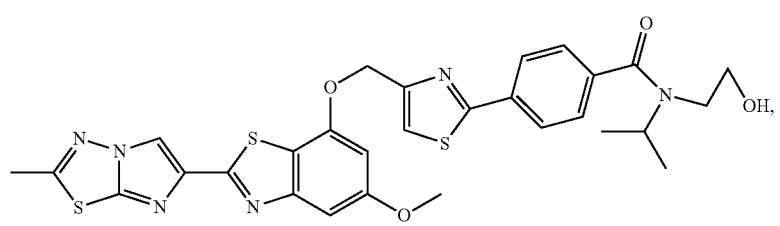
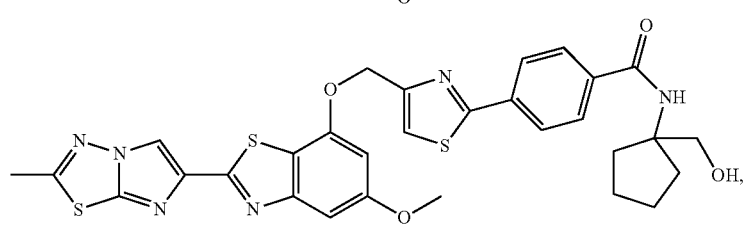
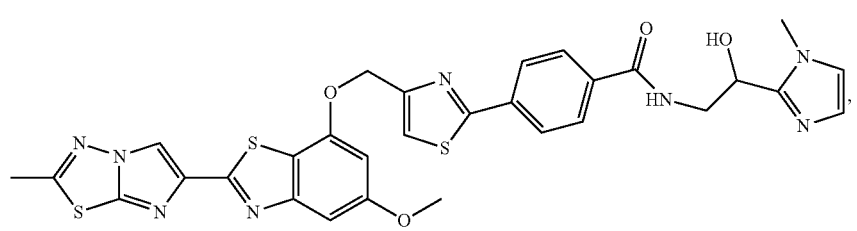
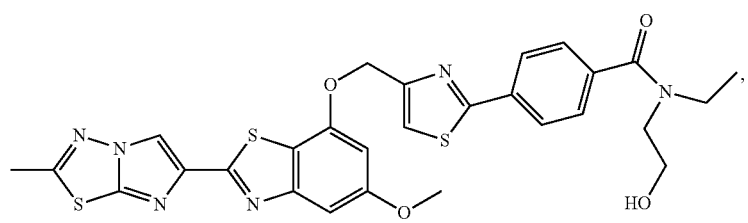
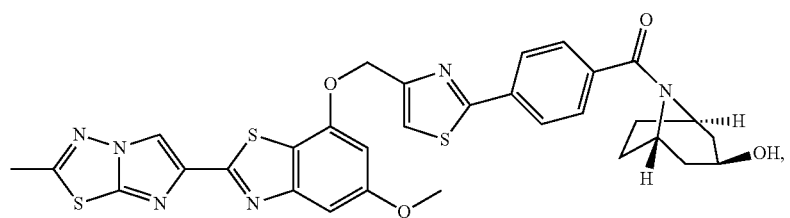

-continued

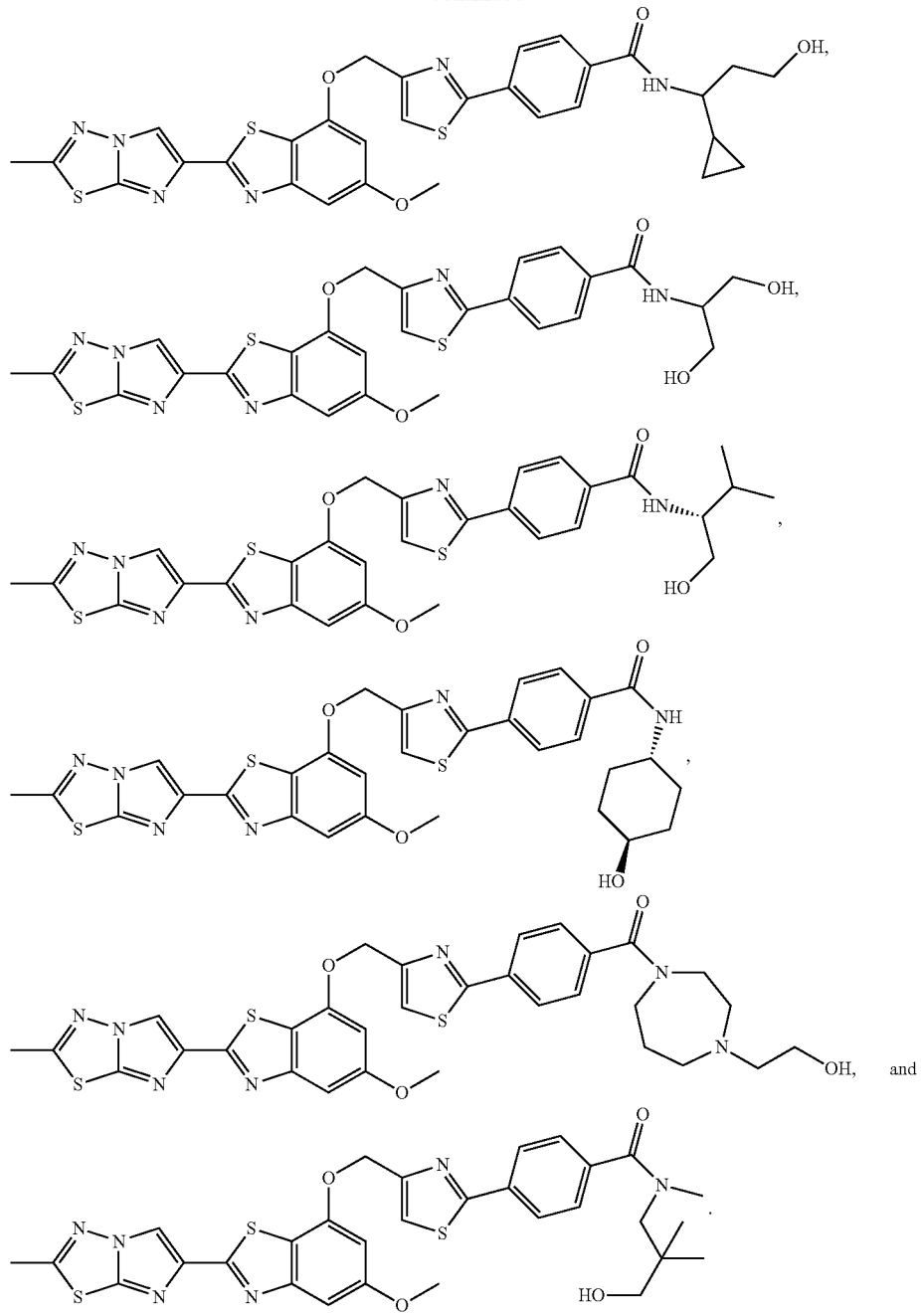

17. A pharmaceutical composition, which comprises a pharmaceutically acceptable carrier and a compound as defined in claim 1, or a stereoisomer, tautomer, or pharmaceutically acceptable salt thereof, alone or in combination with another therapeutic agent.

18. A method of treating a thromboembolic disorder or the primary or secondary prophylaxis of a thromboembolic disorder comprising administering a therapeutically effective amount of a compound as defined in claim 1, or a stereoisomer, tautomer, or pharmaceutically acceptable salt thereof, to a subject in need thereof, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

19. A method of inhibiting or preventing platelet aggregation comprising administering a therapeutically effective amount of a compound as defined in claim 1, or a stereoisomer, tautomer, or pharmaceutically acceptable salt thereof, to a subject in need thereof.

20. A method of treating a thromboembolic disorder or the primary or secondary prophylaxis of a thromboembolic disorder comprising administering the pharmaceutical composition as defined in claim 17, wherein the thromboembolic disorder is selected from the group consisting of arterial cardiovascular thromboembolic disorders, venous cardiovascular thromboembolic disorders, cerebrovascular thromboembolic disorders, and thromboembolic disorders in the chambers of the heart or in the peripheral circulation.

21. A method of inhibiting or preventing platelet aggregation comprising administering the pharmaceutical composition as defined in claim 17.

* * * * *